(12) United States Patent
Miller

(10) Patent No.: US 7,504,231 B2
(45) Date of Patent: *Mar. 17, 2009

(54) METHOD OF ALLEVIATING CHRONIC PAIN VIA PERIPHERAL INHIBITION OF NEUROTRANSMITTER SYNTHESIS

(75) Inventor: Kenneth E. Miller, Sapulpa, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 743 days.

This patent is subject to a terminal disclaimer.

(21) Appl. No.: 10/660,093

(22) Filed: Sep. 11, 2003

(65) Prior Publication Data

US 2004/0126368 A1 Jul. 1, 2004

Related U.S. Application Data

(63) Continuation-in-part of application No. 10/245,098, filed on Sep. 13, 2002.

(60) Provisional application No. 60/411,311, filed on Sep. 13, 2002, provisional application No. 60/318,861, filed on Sep. 13, 2001.

(51) Int. Cl.
*A61K 38/43* (2006.01)
*A61K 31/195* (2006.01)

(52) U.S. Cl. .................. 435/7.71; 424/94.1; 514/557; 514/564; 514/570

(58) Field of Classification Search .............. 424/94.1; 435/7.71; 514/557, 564, 570
See application file for complete search history.

(56) References Cited

U.S. PATENT DOCUMENTS

| 5,158,976 | A | * | 10/1992 | Rosenberg | .................. 514/561 |
| 6,013,672 | A | | 1/2000 | Ye et al. | |
| 6,291,523 | B1 | * | 9/2001 | Fujimoto et al. | ............ 514/533 |
| 7,288,246 | B2 | * | 10/2007 | Miller | ....................... 424/94.1 |

* cited by examiner

*Primary Examiner*—Jon P Weber
*Assistant Examiner*—Kailash C Srivastava
(74) *Attorney, Agent, or Firm*—Dunlap Codding, P.C.

(57) ABSTRACT

A composition having sustained pain-relieving properties such that the composition may be administered to a subject to alleviate chronic pain. The composition includes an effective amount of at least one inhibitor of neurotransmitter synthesis. A method for alleviating chronic pain in a subject for an extended period of time is also disclosed, in which the compound is administered to a subject suffering from chronic pain at a site of inflammation such that the administration of the compound results in a reduction in at least one of thermal and mechanical pain responses at the site of inflammation for a period of at least two days without any resulting acute pain behavior. The composition may further include an effective amount of at least one compound having analgesic effects such that the composition also alleviates acute pain.

20 Claims, 30 Drawing Sheets
(2 of 30 Drawing Sheet(s) Filed in Color)

DON Dose response - Pressure

FIGURE 8B

FIGURE 12
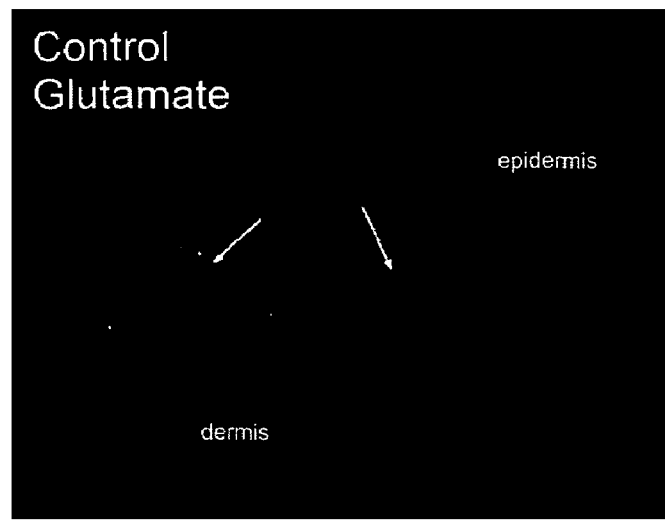
A
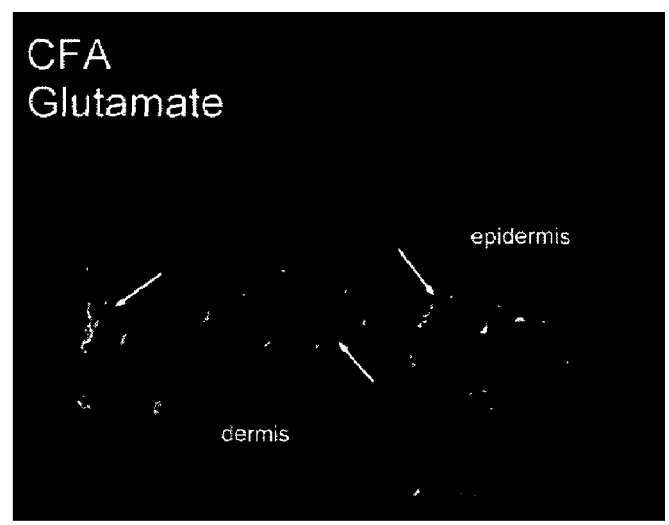
B
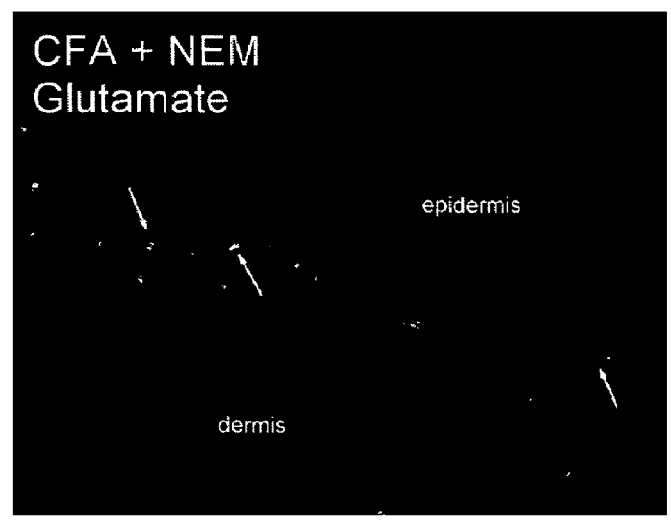
C

Figure 17
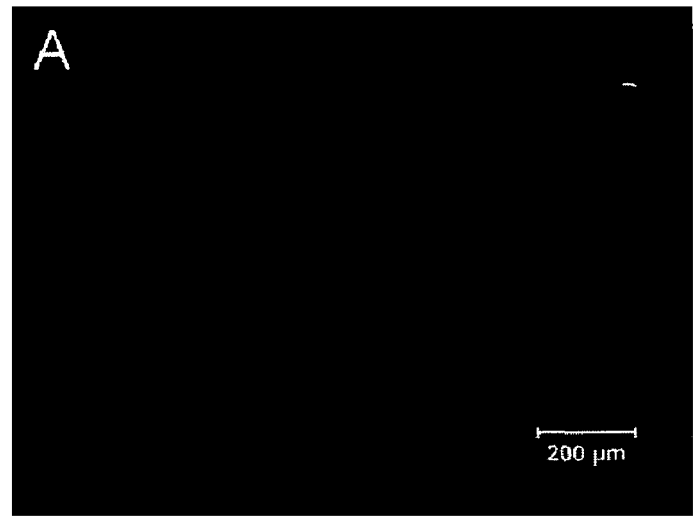
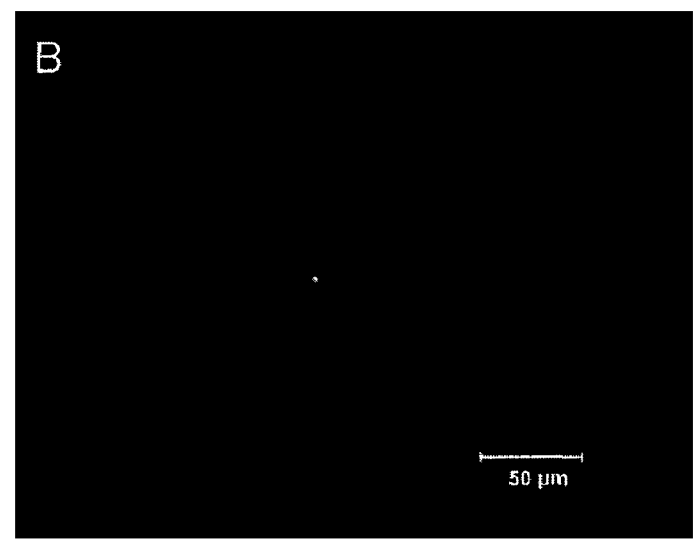
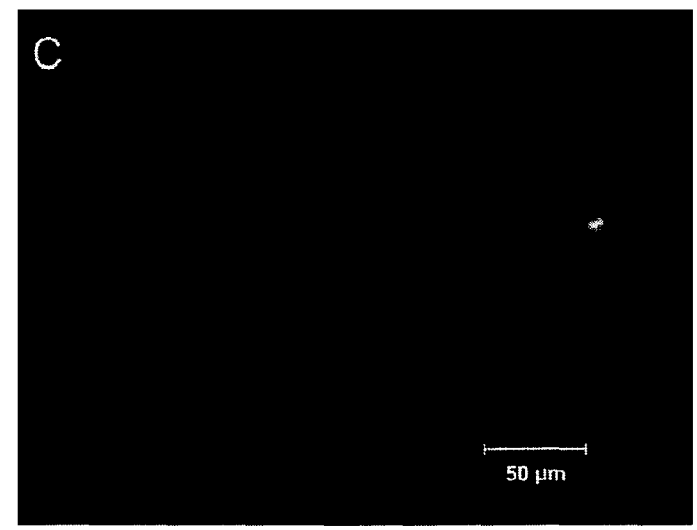

Figure 22
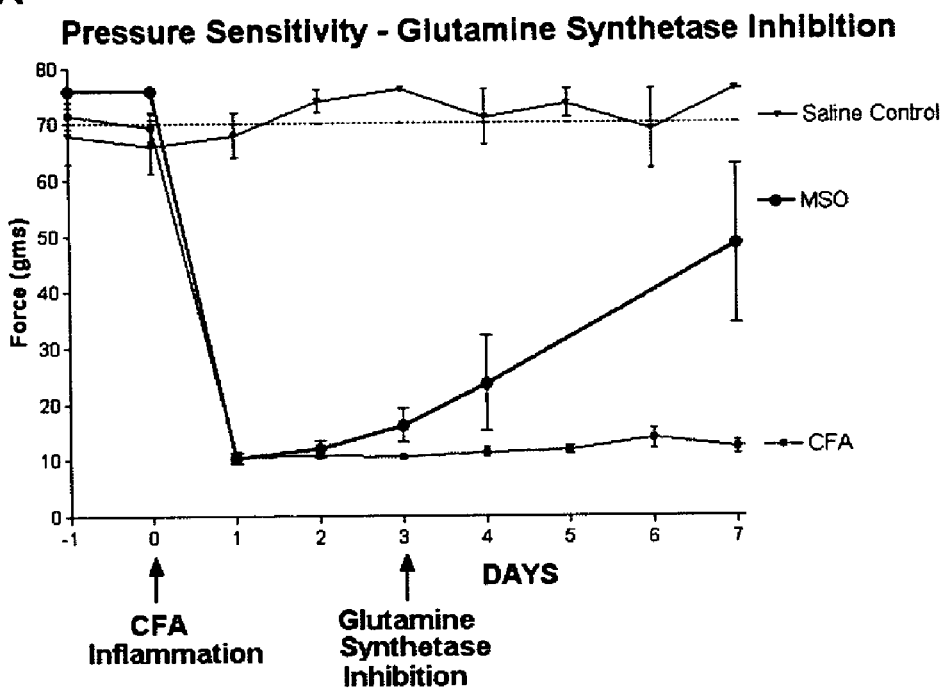
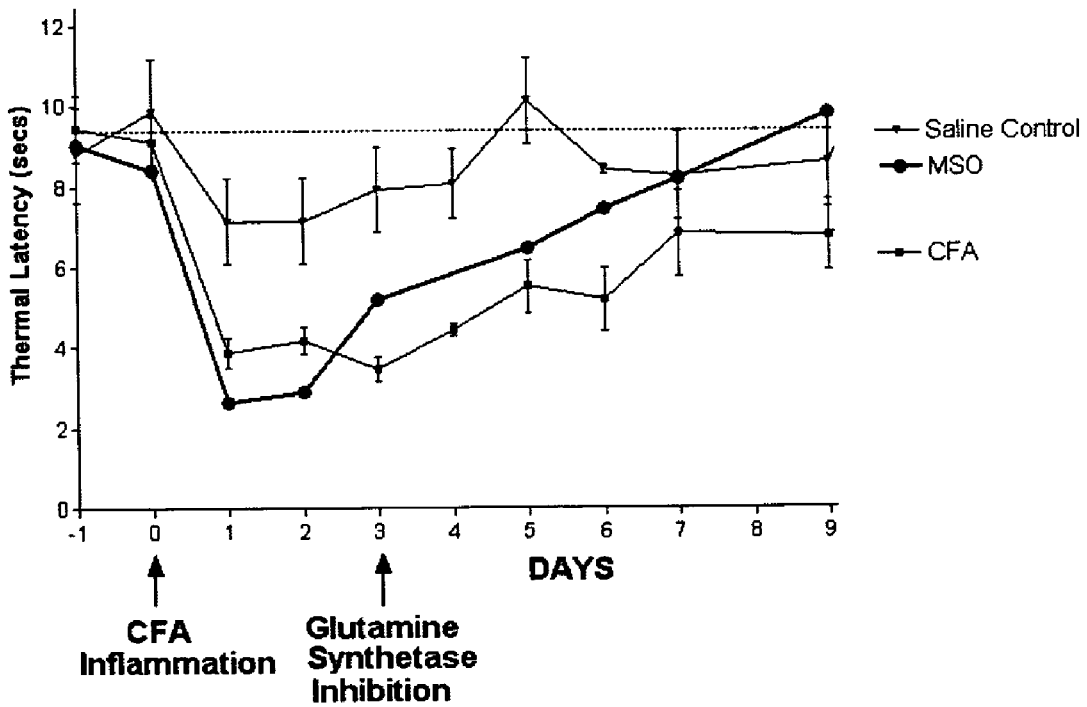

METHOD OF ALLEVIATING CHRONIC PAIN VIA PERIPHERAL INHIBITION OF NEUROTRANSMITTER SYNTHESIS

CROSS-REFERENCE TO RELATED APPLICATIONS

The present application claims benefit under 35 U.S.C. 119(e) of provisional application U.S. Ser. No. 60/411,311, filed Sep. 13, 2002, the contents of which are hereby expressly incorporated herein by reference.

This application is also a continuation-in-part of U.S. Ser. No. 10/245,098, filed Sep. 13, 2002, which claims the benefit under 35 U.S.C. 119(e) of provisional application U.S. Ser. No. 60/318,861, filed Sep. 13, 2001; the contents of each of which are hereby expressly incorporated herein by reference.

FEDERALLY SPONSORED RESEARCH OR DEVELOPMENT

The government owns certain rights in the present invention pursuant to a grant from the National Institutes of Health, #R101AR47410-01A1.

BACKGROUND OF THE INVENTION

1. Field of the Invention

The present invention generally relates to methods of alleviating pain, and more particularly, but not by way of limitation, to a method of alleviating chronic pain by regulation of neurotransmitter synthesis.

2. Brief Description of the Related Art

Chronic inflammatory pain is a debilitating condition causing suffering, loss of work and loss of revenue. Several methods of relieving pain from chronic inflammatory conditions such as rheumatoid arthritis, muscle damage, and osteoarthritis are known in the art. However, the prior art methods of relieving pain have several unpleasant or serious side effects and require multiple daily administrations to be effective. For example, narcotics can be used for refractory chronic pain, but administration of narcotics has many side effects, including respiratory depression as well as the possibility of abuse. Additionally, another current method for relief of peripheral pain is topical application of capsaicin cream. This method may be effective for several days but produces severe acute pain in many patients. Further, some pain conditions such as myofascial pain and neuropathies due to nerve injury or disease currently do not have any effective therapies for alleviating pain associated therewith.

Therefore, there exists a need in the art for improved methods of alleviating chronic pain, including pain associated with conditions such as rheumatoid arthritis, muscle damage, osteoarthritis, myofascial pain and neuropathies, which overcome the disadvantages and defects of the prior art methods. It is to such methods of alleviating chronic pain for an extended period of time and with no side effects that the present invention is directed.

SUMMARY OF THE INVENTION

The present invention is related to a method of alleviating chronic pain in a subject for an extended period of time, as well as to a composition having analgesic effects that provides alleviation of chronic pain in a subject for an extended period of time. Briefly, the method of alleviating chronic pain of the present invention includes administration of an effective amount of at least one inhibitor of neurotransmitter synthesis into an inflammatory field. Such inhibitor of neurotransmitter synthesis may be a glutamine synthetase inhibitor, a glutamine cycle inhibitor, a glutamate dehydrogenase inhibitor, a pyruvate carboxylase inhibitor, a glial cell tricarboxylic acid cycle inhibitor, or combinations thereof.

Pain is a major complication in arthritis and other disorders, and it is difficult to treat effectively for long periods of time. Persistent stimulation of sensory nerves in the area of inflammation is one of the contributors to chronic pain. One stimulator of sensory nerve fibers is glutamate produced by the sensory nerve fibers themselves. Glutamate is a neurotransmitter utilized in signaling by the sensory neurons, and glutamate causes sensitization of surrounding sensory nerves, thereby producing the feeling of pain. The present invention discloses that during experimental arthritis in rats, the sensory nerve cells increase production of glutaminase (GT), the neuronal enzyme that produces glutamate from glutamine. Elevated amounts of glutaminase are shipped to the sensory nerve endings in the skin and joints, thereby causing increased amounts of glutamate to be produced (see FIG. 1). The skin and joints from control rats have little to no detectable glutamate or glutaminase, so this enzyme and neurotransmitter have not been considered previously as possible therapeutic targets for pain relief via peripheral inhibition.

The method of the present invention includes local administration of an effective amount of at least one inhibitor of neurotransmitter synthesis, such as a glutaminase inhibitor, to a subject suffering from chronic pain at a site of inflammation, and the administration of the inhibitor of neurotransmitter synthesis results in a reduction in nociceptive responses, such as thermal and mechanical pain responses, at the site of inflammation for a period of at least two days without any resulting acute pain behavior.

In the experiments described herein, rats were injected in the hindpaw with Complete Freund's adjuvant (heat killed Mycobacterium) to create an experimental arthritis. Rats with this type of chronic inflammation have increased sensitivity to pressure and temperature. After several days of inflammation, some rats were injected with a glutaminase inhibitor or an inhibitor of neurotransmitter synthesis, such as but not limited to, 6-diazo-5-oxo-L-norleucine (DON), N-ethylmaleimide (NEM), dicoumarol (DC), bromothymol blue (BB), Palmitoyl Coenzyme A (P-CoA), methionine sulfoximine (MSO) and fluoroacetate (FA). Following application of the glutaminase inhibitor or inhibitor of neurotransmitter synthesis, the animal's sensitivities to pressure and temperature were brought to more normal values for many days, and these results were seen after only a single injection of the glutaminase inhibitor or inhibitor of neurotransmitter synthesis.

The present invention also includes a method of alleviating both acute and chronic pain in a subject for an extended period of time. The method includes administration of a combination therapy of an effective amount of at least one compound having analgesic effects that provides substantially immediate relief of acute pain in combination with an effective amount of at least one inhibitor of neurotransmitter synthesis to a subject suffering from acute and chronic pain at a site of inflammation. Such combination therapy will provide relief of both acute and chronic pain and results in a substantially immediate reduction of nociceptive responses at the site of inflammation that last for a period of at least two days without any resulting acute behavior.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8B is a graphic representation representing the DON dose response for pain relief from pressure stimulation. The area under the curve for each dose was determined from Day 3 to Day 5. No differences in the amount of pain relief were determined for the doses tested (0.1-10 $\mu$Mole/25 $\mu$l).

FIG. 12 are photomicrographs illustrating glutamate immunoreactivity in tissue sections from the hindpaw skin of a control rat (FIG. 12A), a rat after CFA inflammation (FIG. 12B), and a rat after CFA inflammation and following glutaminase inhibition with NEM (FIG. 12C). In FIG. 12A, very little glutamate immunoreactivity is detected in sensory nerves (arrows) in normal skin. In FIG. 12B, after CFA inflammation, sensory nerve fibers contain elevated amounts of glutamate (arrows). in FIG. 12C, following CFA inflammation and glutaminase inhibition with NEM or DON, glutamate levels in sensory nerve fibers (arrows) are reduced to near normal levels. Similar results in all three conditions occur for glutaminase immunoreactivity in sensory nerves.

FIGS. 14A-C illustrate that ZC levels are modified during chronic inflammation. ZC-immunoreactivity (IR) was examined in the rat $L_4$DRG during inflammation at an early and later time point (2, 6 days). ZC-IR in DRG neurons of control rats (A) shows a moderate staining of the cytoplasm of all neurons. Following inflammation for 48 hrs, ZC-IR is elevated in the cytoplasm and now appears in the nuclei of many neurons (arrows). ZC-IR remains elevated at 6 days of inflammation and occurs mainly in the cytoplasm although some nuclei (arrows) contain light ZC-IR.

FIG. 17 are photomicrographs illustrating representative immunohistochemical controls. (A) Rabbit anti-glutamine absorption control in sciatic nerve. Compare with an adjacent section stained for glutamine (see FIG. 19A). (B) Rabbit anti-pyruvate carboxylase absorption control in DRG with rabbit anti-pyruvate carboxylase. Compare with an adjacent sectiono stained for pyruvate carboxylase (see FIG. 18C). (C) Omission of primary antiserum and subsequent processing with horse anti-mouse IgG and FITC-Avidin. No specific staining is observed in these controls.

around large axons. GS immunoreactivity was prevalent in the Schwann cell bodies (long arrows) and the cytoplasmic outer rim (short arrows) of the Schwann cells. The myelin sheath (asterisks) appeared non-immunoreactive. Magnification bars: (A) 50 µm, (B) 15 µm.

Figure 21:
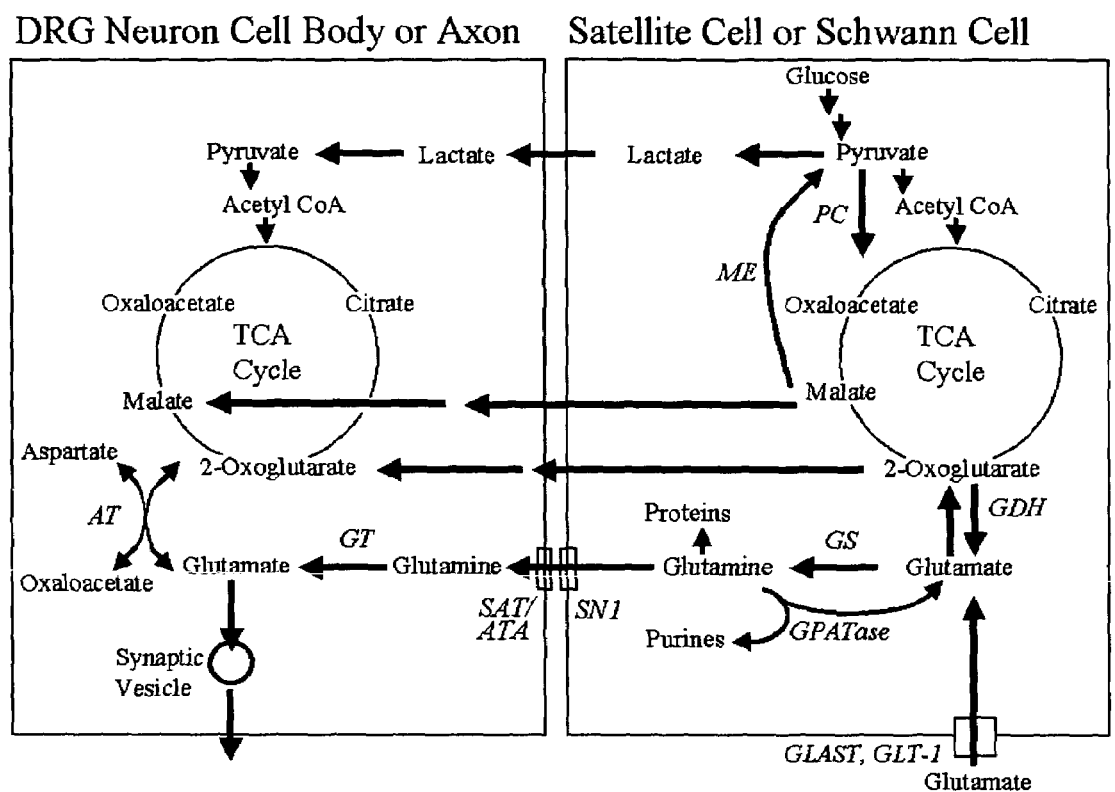

FIG. 21 is a diagrammatic represenation illustrating that glial cell metabolism is intricately related to neuronal metabolism. This diagram illustrates that glutamine, glutamine synthetase, glutamate dehydrogenase, and pyruvate carboxylase are located in the peripheral nervous system in satellite cells of the DRG and Schwann cells of the peripheral nerve. These enzymes could have major roles in supporting peripheral neuronal metabolism and neurotransmission. Glial cells take up glutamate from the extracellular milieu via transporters (GLAST, GLT-1) and GS converts it to glutamine. Glutamine can be shuttled out of glial cells by the SN1 glutamine transporter and taken up by neurons via the SAT/ATA glutamine transporters for use by glutaminase (GT) in the glutamine cycle. In addition, glutamine is an important branch point substrate for purine synthesis via GPATase. Glutamate dehydrogenase is a bidirectional enzyme that can either add glutamate for GS in the glutamine cycle or convert glutamate to 2-oxoglutarate for the TCA cycle. 2-Oxoglutarate and other TCA intermediates such as malate can be shuttled from glia for use in neurons. Malate also can be converted to pyruvate via malic enzyme (ME). Pyruvate can be converted to lactate and used in neuronal metabolism. Pyruvate carboxylase is an anaplerotic enzyme that refills the glial TCA cycle with carbon as TCA intermediates are used for other purposes.

FIG. 22 are graphic representations of the effects of inhibition of glutamine synthetase on thermal and mechanical pain. The hindpaw responses of rats to pressure sensitivity (FIG. 22A) and thermal sensitvity (FIG. 22B) were determined for a control rat, a rat after CFA inflammation, and a rat after CFA inflammation and following glutamine synthetase inhibition with methionine sulfoximine (MSO).

Figure 23:
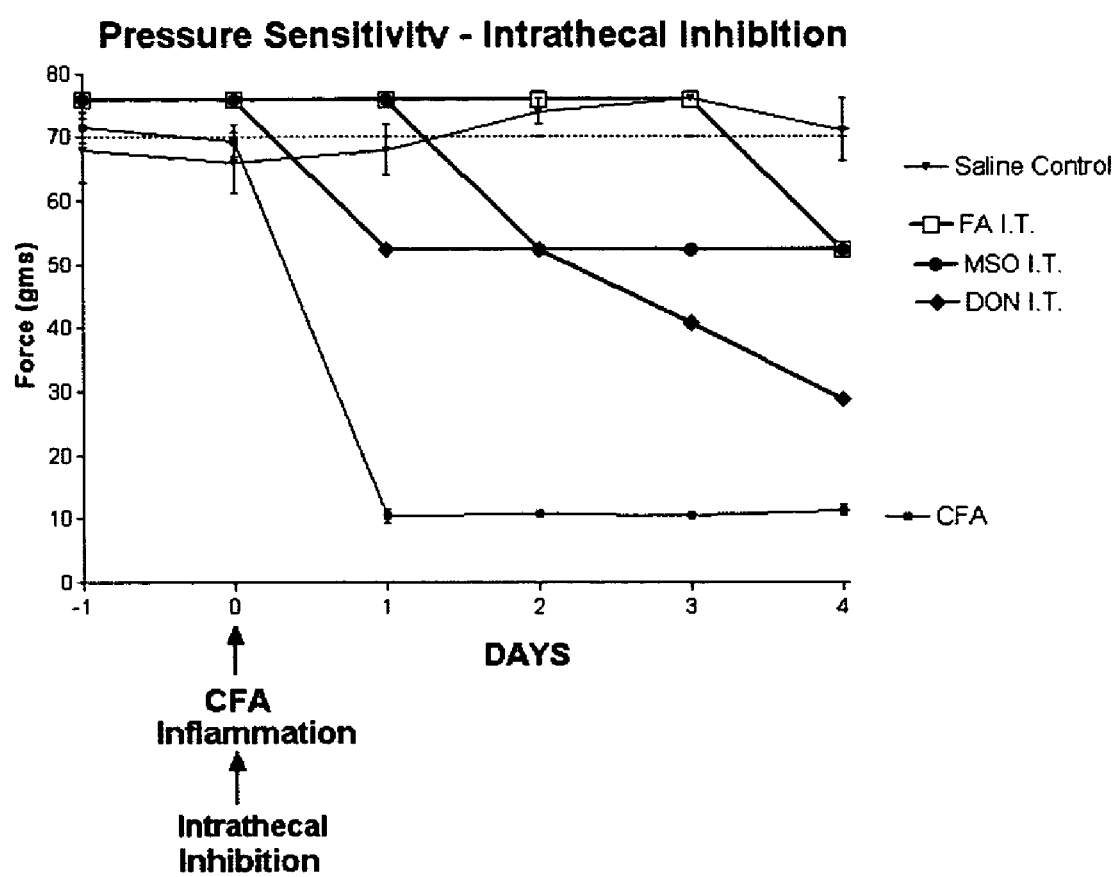

FIG. 23 is a graphic representation illsutrating the effects of intrathecal injection of MSO, DON or fluoroacetate (FA) on pressure sensitivity in the hindpaw of rats following CFA inflammation.

Figure 24:
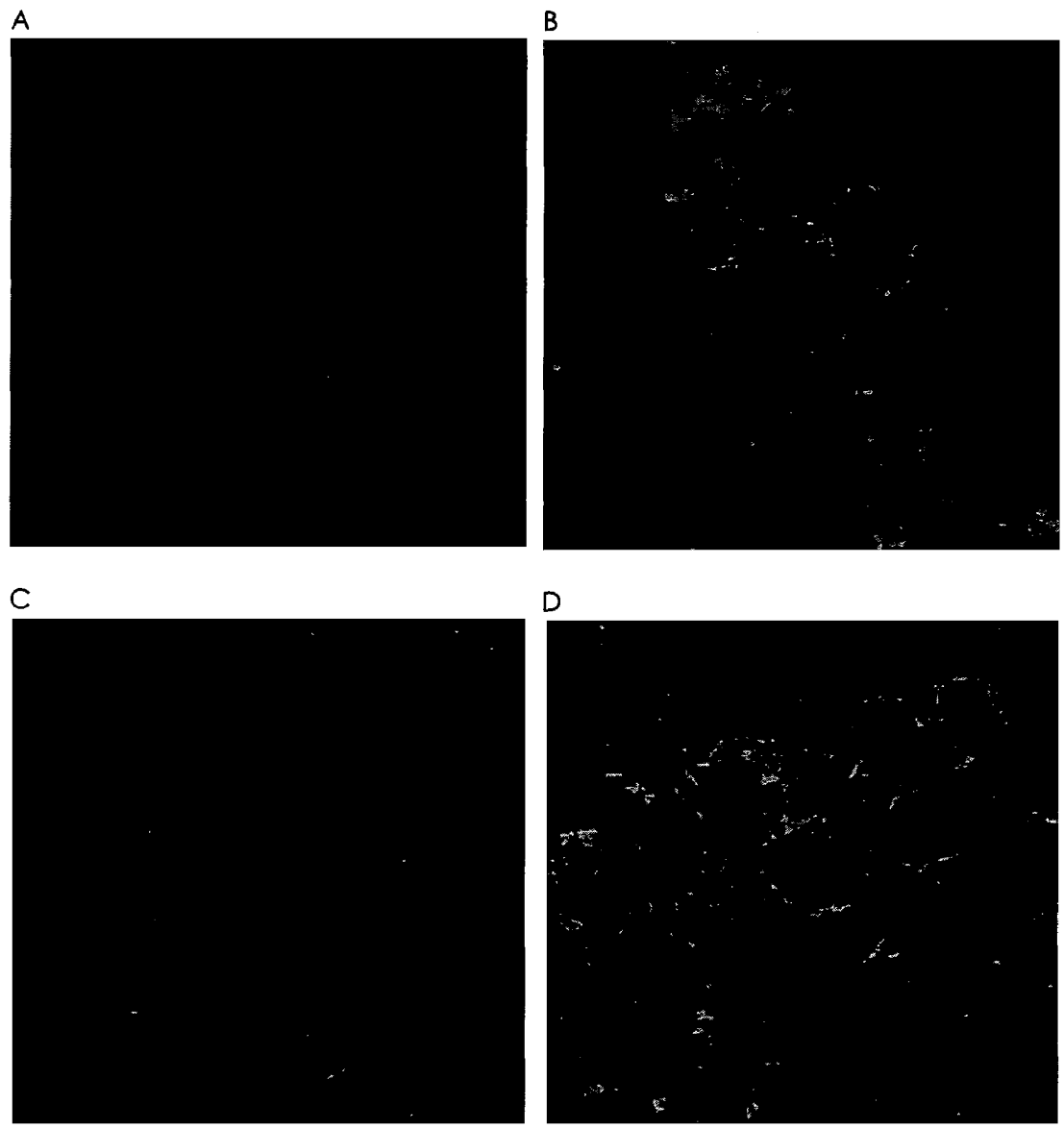

FIG. 24 are photomicrographs illustrating that satellite (glial) cells in the dorsal root ganglia (DRG) increase 'glutamine cycle' enzymes and products during chronic inflammation. Inflammation was induced with intraplantar CFA in the right hindpaw. In normal DRG's, glutamine synthetase (A; GS) and glutamine (C; the product of GS) immunoreactivity is located in satellite cells surrounding DRG neuronal cell bodies. After 3 days of inflammation, increased immunoreactivity for GS and glutamine is observed in most satellite cells.

DETAILED DESCRIPTION OF THE INVENTION

Before explaining at least one embodiment of the invention in detail, it is to be understood that the invention is not limited in its application to the details of construction and the arrangement of the components or steps or methodologies set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The method of the present invention includes administration of an effective amount of at least one inhibitor of neurotransmitter synthesis to a subject suffering from chronic pain at a site of inflammation. In one embodiment, the inhibitor of neurotransmitter synthesis is a glutaminase inhibitor. The terms "glutaminase inhibitors" or "GT inhibitors" as used herein will be understood to include inhibitors that affect the activity of the glutaminase enzyme, such as inhibitors that may affect binding of glutamine, glutamate or various cofactors to the enzyme. That is, a GT inhibitor may block binding of the substrate glutamine to glutaminase, inhibit release of the product glutamate from glutaminase, or block cofactor binding and therefore slow the catalytic rate of the enzyme. Examples of such GT inhibitors which may be utilized in the method of the present invention include nonspecific inhibitors such as amidotransferase inhibitors and long chain fatty acids. Specific Examples of specific inhibitors of glutaminase activity which may be utilized in the method of the present invention include 6-diazo-5-oxo-L-norleucine (DON), N-ethylmaleimide (NEM), p-chloromercuriphenylsulfonate (pCMPS), L-2-amino-4-oxo-5-chloropentoic acid, DON plus o-carbamoyl-L-serine, acivicin [(alphaS,5S)-alpha-amino-3-chloro-4,5-dihydro-5-isoxazoleacetic acid], azaserine, palmitoyl coenzyme A (palmitoyl CoA), stearoyl coenzyme A (stearoyl CoA), bromothymol blue, and combinations or derivatives thereof.

Figure 1:
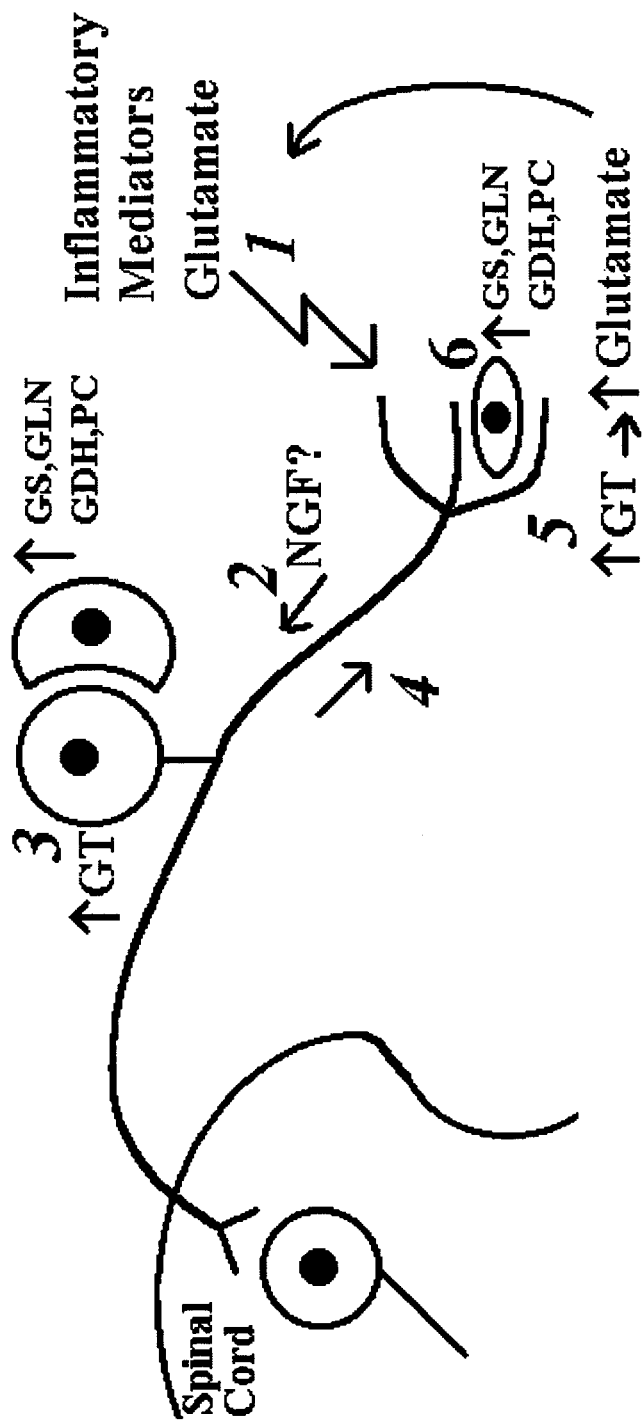
FIG. 1 is a diagrammatic representation of the effects of Glutamate and glutaminase on peripheral sensory nerve stimulation and exacerbation of pain responses. Inflammatory mediators in the skin and joints stimulate the release of glutamate and other agents that sensitize peripheral sensory nerve fibers (1). Initial activation of the glutamine cycle to increase glutamate production as a response to acute pain occurs in the glutamine cycle enzymes via flux control or signal transduction pathways. For long-term regulation, a retrograde signal (2), possibly nerve growth factor (NGF), causes the DRG cell body (3) to increase production of glutaminase (GT). Chronic pain conditions cause a long-term alteration in glutamate metabolism in neuronal cell bodies in sensory ganglia (3). DRG satellite cells (3) also are activated and increase production of glutamine synthetase (GS), glutamate dehydrogenase (GDH), pyruvate carboxylase (PC), and glutamine (GLN). Increased amounts of GT and glutamate are transported peripherally (4) producing elevated levels in peripheral primary afferent nerve terminals (5). Elevated levels of glutamate are released causing peripheral terminals to remain sensitized and exacerbates pain responses (1). Blockade of glutaminase with glutaminase metabolic inhibitors stops glutamate production and release and decreases pain. In addition, elevated glutamate levels cause local cells, eg., Schwann cells, to increase GS, GLN, GDH, and PC production (6). Interruption of the glutamine cycle at the DRG or peripheral nerve terminals represents a novel approach for controlling peripheral afferent sensitization and the pain that ensues.
Figure 2:
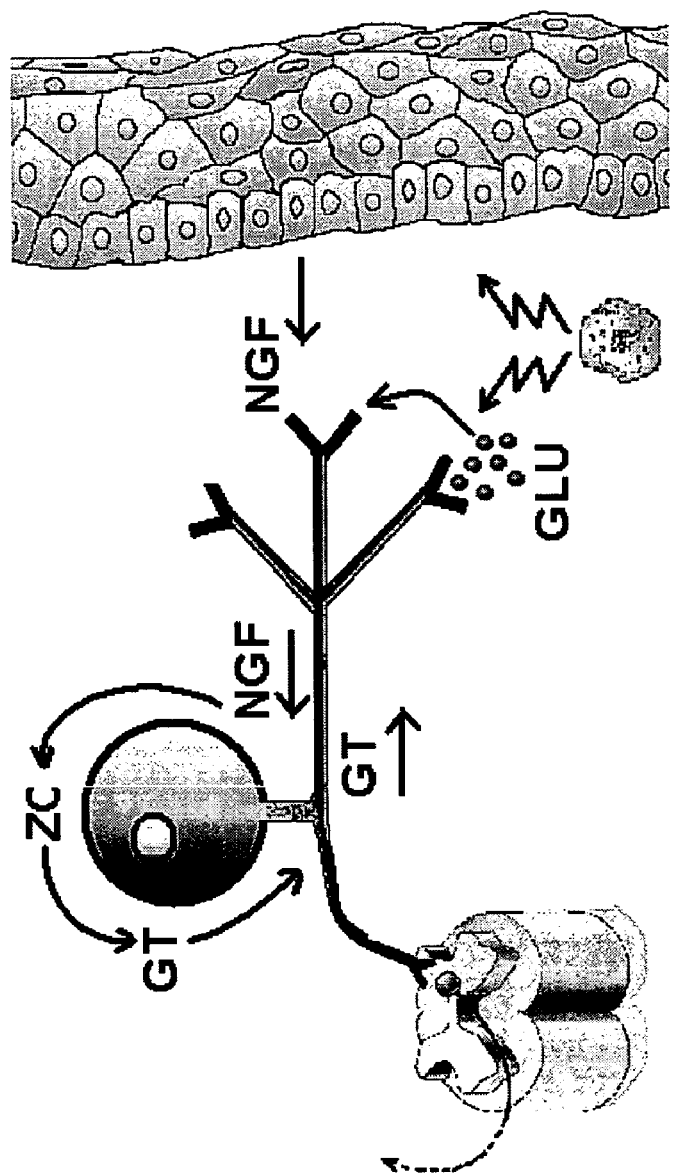
FIG. 2 is a model regarding glutamate production in primary sensory neurons during chronic inflammation. Inflammatory mediators (lightning bolts) activate and sensitize peripheral afferent terminals. This leads to the release of glutamate (GLU) and other substances from peripheral terminals causing further sensitization (arrow). Inflammation stimulates keratinocytes to increase production of nerve growth factor (NGF). NGF is taken up and retrogradely transported to the neuronal cell body where it stimulates increased production of glutaminase (GT). Increased production of GT occurs from stabilization of GT mRNA via zeta-crystallin: quinone oxidoreductase (ZC). Increased amounts of GT are shipped to the periphery causing elevated glutamate production and release, further primary afferent sensitization, and exacerbation of nociceptive responses.

The terms "glutaminase inhibitors" or "GT inhibitors" will also be understood to include inhibitors of glutaminase production. Inhibitors of glutaminase production include, but are not limited to, inhibitors of transcription of the gene encoding glutaminase as well as inhibitors of regulatory proteins involved in transcription of the glutaminase gene. Inhibitors of glutaminase production also include, but are not limited to, inhibitors of translation of the glutaminase mRNA and inhibitors of stabilization of the glutaminase mRNA as well as compounds which increase degradation of the glutaminase mRNA. For example, as shown in FIG. 2, nerve growth factor (NGF) is produced by keratinocytes in response to inflammation and is taken up and retrogradely transported to the neuronal cell body where it stimulates increased production of GT. In addition, increased production of GT also occurs from stabilization of GT mRNA via zeta-crystallin:quinone oxidoreductase (ZC) (FIG. 2). Therefore, a compound capable of neutralizing or inhibiting ZC or NGF also falls within the scope of the terms "glutaminase inhibitor" or "GT inhibitor". One specific example of a compound functioning in this manner is dicoumarol (DC), which is shown herein to inhibit ZC activity and thus inhibit GT production, thereby relieving pain. Therefore, the terms "glutaminase inhibitor", "inhibitor of glutaminase enzyme activity" and "inhibitor of glutaminase synthesis" can all be used interchangeably herein.

The term "an inhibitor of neurotransmitter synthesis" as used herein will also include compounds that inhibit, either directly or indirectly, the synthesis of a substrate that is converted to a neurotransmitter. For example, glutaminase converts glutamine to the neurotransmitter glutamate, and therefore inhibitors of enzymes which are directly or indirectly involved in synthesis of glutamine, such as but not limited to pyruvate carboxylase, glutamate dehydrogenase, glutamine synthetase, and various known enzymes of the tricarboxylic acid (TCA) cycle, also fall within the scope of the term "inhibitor of neurotransmitter synthesis", as used in accordance with the present invention. Examples of pyruvate carboxylase inhibitors that may be used in accordance with the present invention include, but are not limited to, phenyl acetic acid (PAA), phenylacetyl Coenzyme-A, phenylacetyl Co-A ester, oxamate, and combinations and derivatives thereof. Examples of glutamine synthetase inhibitors that may be used in accordance with the present invention include, but are not limited to, methionine-S-sulfoximine (MSO), phosphinothricin (PPT), 4-N-hydroxy-L-2,4-diaminobutyric acid (NH-DABA), Delta-hydroxylysine, and combinations and derivatives thereof. Examples of glutamate dehydrogenase inhibitors that may be used in accordance with the present invention include, but are not limited to, bromofuroate, Palmitoyl-Coenzyme-A (Palmitoyl-Co-A), vanadium compounds (including, but not limited to, orthovanadate, vanadyl sulphate, vanadyl acetylacetonate, and combinations thereof), glutarate, 2-oxoglutarate (α-ketoglutarate), estrogen, estrogen analogues, pyridine-2,6-dicarboxylic acid, and derivatives thereof as well as combinations thereof, such as, but not limited to, 2-oxoglutarate and vanadyl sulphate. Examples of glial cell TCA cycle inhibitors that may be used in accordance with the present invention include, but are not limited to, fluoroacetate, fluorocitrate, and combinations and derivatives thereof. Further, the term "inhibitor of neurotransmitter synthesis" will also include two or more of the inhibitors listed above from two or more different classes, for example, but not by way of limitation, the combination of a glutamine synthetase inhibitor and a glial cell TCA cycle inhibitor.

The method of alleviating chronic pain of the present invention results in pain relief (both thermal and mechanical) for several days by way of peripheral glutaminase inhibition without any resulting acute pain behavior, as observed by the prior art methods, such as application of capsaicin cream. While the initial experiments described herein have utilized injection of an inhibitor of neurotransmitter synthesis, the inhibitor of neurotransmitter synthesis should also be amenable to topical or oral application. For example, an oral inhibitor of neurotransmitter synthesis given as a prodrug or with limited to substantially no penetration into the central nervous system would also be effective in producing widespread pain relief. Therefore, it is to be understood that the method of alleviating chronic pain of the present invention is not limited to injection of an inhibitor of neurotransmitter synthesis but also includes other methods of application of such inhibitor(s), such as, but not limited to, oral, topical, transdermal, parenteral, subcutaneous, intranasal, intramuscular and intravenous routes, including both local and systemic applications. In addition, the formulations containing at least one inhibitor of neurotransmitter synthesis described herein may be designed to provide delayed or controlled release using formulation techniques which are well known in the art. Using such methods of delayed or controlled release would provide an even longer period of pain relief.

The term "subject" as used herein will be understood to include a mammal, that is, a member of the Mammalia class of higher vertebrates. The term "mammal" as used herein includes, but is not limited to, a human.

The term "method of alleviating pain" as used herein will be understood to include a reduction, substantial elimination or substantial amelioration of the condition of pain, including nociceptive behavior in response to mechanical or thermal stimuli. The term "nociceptive responses" as used herein will be understood to refer to responses that occur in reaction to pain, such as mechanical or thermal stimuli.

The term "pain" as used herein will be understood to refer to all types of pain, including acute pain and chronic pain. The term "chronic pain" as used herein will be understood to include, but is not limited to, pain associated with rheumatoid arthritis or osteoarthritis, neuropathic pain, pain associated with muscle damage, myofascial pain, chronic lower back pain, pain resulting from burns, and the like.

The present invention also includes a method of alleviating both acute and chronic pain in a subject for an extended period of time. The method includes administration of a combination therapy of an effective amount of at least one compound having analgesic effects that provides substantially immediate relief of acute pain in combination with an effective amount of at least one inhibitor of neurotransmitter synthesis to a subject suffering from acute and chronic pain at a site of inflammation. Such combination therapy will provide relief of both acute and chronic pain and results in a substantially immediate reduction of nociceptive responses at the site of inflammation that last for a period of at least two days without any resulting acute behavior. Compounds having analgesic effects that may be utilized in such a method are known to those of ordinary skill in the art and include, but are not limited to, benzocaine, lidocaine, novocaine, and the like. In addition, compounds which function as glutamate inhibitors or inhibitors of glutamate binding to glutamate receptors on peripheral sensory nerves may also be utilized as the compound having analgesic effects in the above-described combination therapy. Other compounds having analgesic effects that may be utilized in the method of the present invention include aspirin, acetaminophen, paracetamol, indomethacin, cholinergic analgesics, adrenergic agents, nonsteroidal anti-inflammatory drugs, and other like compounds known in the art. Compounds having analgesic effects are widely known, and it is well within the skill of a person having ordinary skill in the art to determine an effective amount of the compound having analgesic effects that will result in a reduction of acute pain upon administration to a subject.

DETAILED DESCRIPTION OF FIGS. 1-16

Several animal models of tonic pain, e.g., subcutaneous and intra-articular injections of inflammatory agents such as complete Freund's adjuvant (CFA), are used to mimic human chronic pain. During the acute phase of inflammation, bradykinin, serotonin, prostaglandins, ATP, $H_+$ and glutamate activate and/or sensitize the afferent limb of primary sensory neurons by increasing spontaneous activity, lowering activation threshold, and increasing or prolonging firing to stimuli [Benton et al., 2000; Millan, 1999; Wood and Docherty, 1997; Zhou et al., 1996]. Sensory neurons respond chronically to inflammation by increasing tachykinin (substance P [SP]) and calcitonin generelated peptide (CGRP) expression and content in dorsal root ganglia (DRG) [Calza et al., 1998; Donaldson et al., 1992; Garrett et al., 1995; Hanesch et al., 1993; Hanesch et al., 1995; Noguchi et al., 1988; Smith et al., 1992] and enhanced immunoreactivity in the spinal dorsal horn [Marlier et al., 1991], skin and joints [Ahmed et al., 1995; Nahin and Byers, 1994]. These peptide containing neurons also are glutamatergic [Battaglia and Rustioni, 1988; DeBiasi and Rustioni, 1988; Miller et al., 1993; Miller et al., 2002], using glutaminase (GT) as the synthetic enzyme for neurotransmitter glutamate production. Despite data regarding functional, morphological, and neuropeptide alterations in sensory neurons, little is known about long-term regulation of glutamate production in tonic pain models.

Acutely, glutamate is released from central primary afferent terminals following noxious stimulation [Skilling et al., 1988; Sorkin et al., 1992; Yang et al., 1996]. Acute glutamate release in the spinal cord, along with SP and CGRP, is responsible for sensitization of spinal neurons leading to persistent or chronic changes [Dickenson, 1995; Pockett, 1995; Urban et al., 1994]. After the induction of knee joint inflammation in monkeys, glutamateimmunoreactive fibers in the spinal cord increase 30% at 4 hr. and nearly 40% at 8 hr. [Sluka et al., 1992]. At 24 hrs., extracellular levels of spinal glutamate in rats are 150% above controls [Yang et al., 1996] indicating a possible prolonged, activity-dependent recruitment of glutamate release from central primary afferents. These studies suggest that glutamate production and release in the spinal cord are modified in pain conditions.

Alteration in glutamate production at these acute and intermediate time points most likely represents modification in flux control and/or modifications of glutamine cycle enzymes, such as GT, via second messenger pathways [Fell, 1997; Kvamme et al., 1983]. Longer-term evaluations of glutamate metabolism have not been performed in tonic pain models as have been carried out for neuropeptides in DRG neurons. Based on previous glutamate studies and evaluations of neuropeptide production, it was hypothesized that inflammation would cause DRG neurons to increase glutaminase production. Therefore, glutaminase immunoreactivity and/or enzyme activity in the rat DRG, skin and joints was examined several days after the induction of chronic arthritis.

Rats developed inflammation in the right hindpaw with redness and edema similar to previous descriptions [Besson and Guilbaud, 1988]. Nociceptive responses to normally non-nociceptive pressures (allodynia) and decreased paw withdrawal latencies to thermal stimuli (hyperalgesia) were observed in rats with CFA induced inflammation (Table 1).

$532.6\pm1.7/\mu m^2$ for the left DRG from CFA rats, and $585.6\pm7.7/\mu m^2$ for the right DRG from CFA rats (FIG. 5A). The GT-IR intensities for the medium (600-1200 $\mu m^2$) DRG cell bodies were $469.3\pm4.9/\mu m^2$ for the control, $509.6\pm8.9/\mu m^2$ for the left DRG from CFA rats, and $556.9\pm7.7/\mu m^2$ for the right DRG from CFA rats (FIG. 5B). Finally, the GT-IR intensities for the large (>1200 $\mu m^2$) DRG cell bodies were $431.6\pm12.2/\mu m^2$ for the control, $448.5\pm10.7/\mu m^2$ for the left DRG from CFA rats, and $491.0\pm5.8/\mu m^2$ for the right DRG from CFA rats (FIG. 5C).

Figure 6:
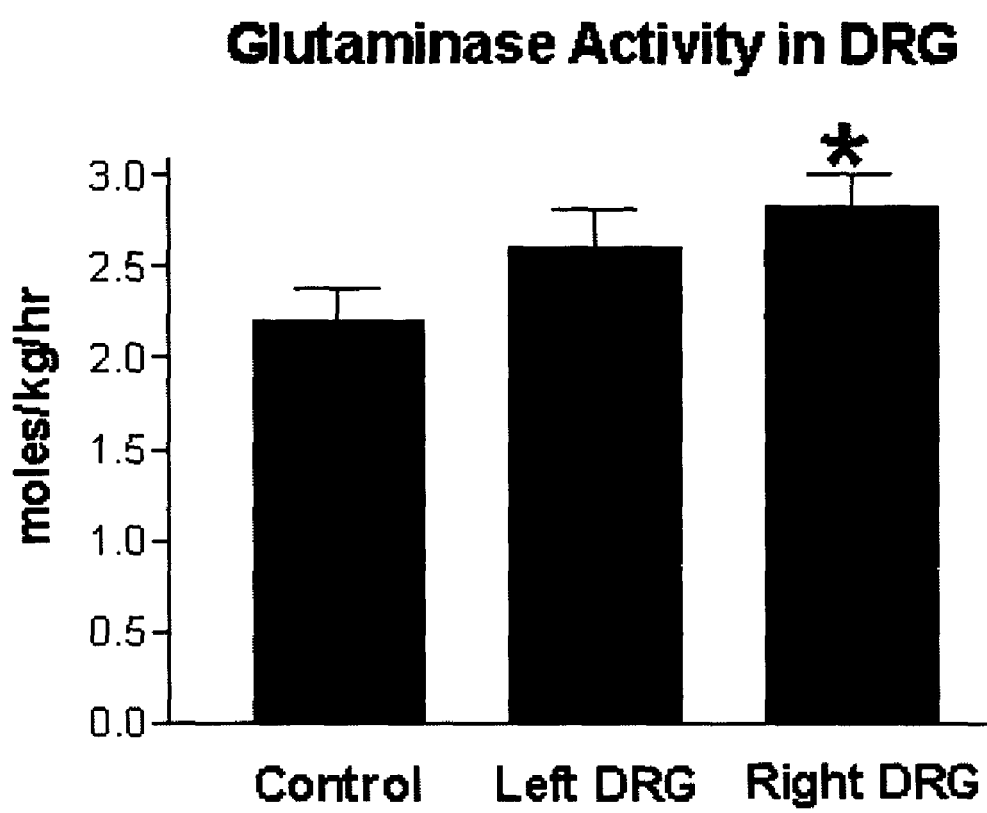
FIG. 6 is a graphic illustration of GT enzyme activity in the L4 DRG at 7 days following CFA inflammation in the right hindpaw. GT activity from the right DRG (2.83+0.30 moles/kg/hr) was elevated (*, $p<0.05$) over control values (2.20+0.18 moles/kg/hr). The left (contralateral) $L_4$DRG (2.61+0.20 moles/kg/hr) was not significantly different from controls or the right (ipsilateral) DRG.

Increased GT enzyme activity was observed in seven day CFA rats from both the left and right $L_4$ DRG's compared to control $L_4$ DRG's (FIG. 6). Control DRG's contained GT enzyme activity of 2.20+0.18 moles/kg/hr., whereas left and right DRG's from CFA rats had GT enzyme activities of 2.61+0.20 moles/kg/hr. and 2.83+0.30 moles/kg/hr., respectively.

Following inflammation, alterations in intensity and distribution of glutamate and GT nerve fibers were noticeable in the skin at 3, 7, and 10 days. Control tissue had weak to moderate immunostaining for glutamate and GT (see FIG. 12A). Compared to control tissue, glutamate and GT immunoreactivity was more intense (see FIG. 12B) in the dermal

TABLE I

Mechanical and Thermal Sensitivities

| | | | | | |
|---|---|---|---|---|---|
| Pressure sensitivity (gm) | Control | 66.6 ± 5.2 | 65.8 ± 4.7 | 64.1 ± 5.3 | 62.9 ± 6.7 |
| | CFA | 61.6 ± 4.4 | 5.2 ± 0.5** | 4.6 ± 0.1** | 6.5 ± 0.9 |
| Thermal sensitivity (sec) | Control | 9.5 ± 0.5 | 7.5 ± 0.6 | 8.5 ± 0.7 | 9.4 ± 0.7 |
| | CFA | 10.0 ± 0.7 | 3.2 ± 0.2** | 2.9 ± 0.8** | 4.1 ± 0.9* |

Pressure sensitivities determined with von Frey hairs are expressed as gm force. Pressure and thermal control values for each day were compared with CFA values with a Student's t test.
*p < 0.01,
**p < 0.0001

Figure 3:
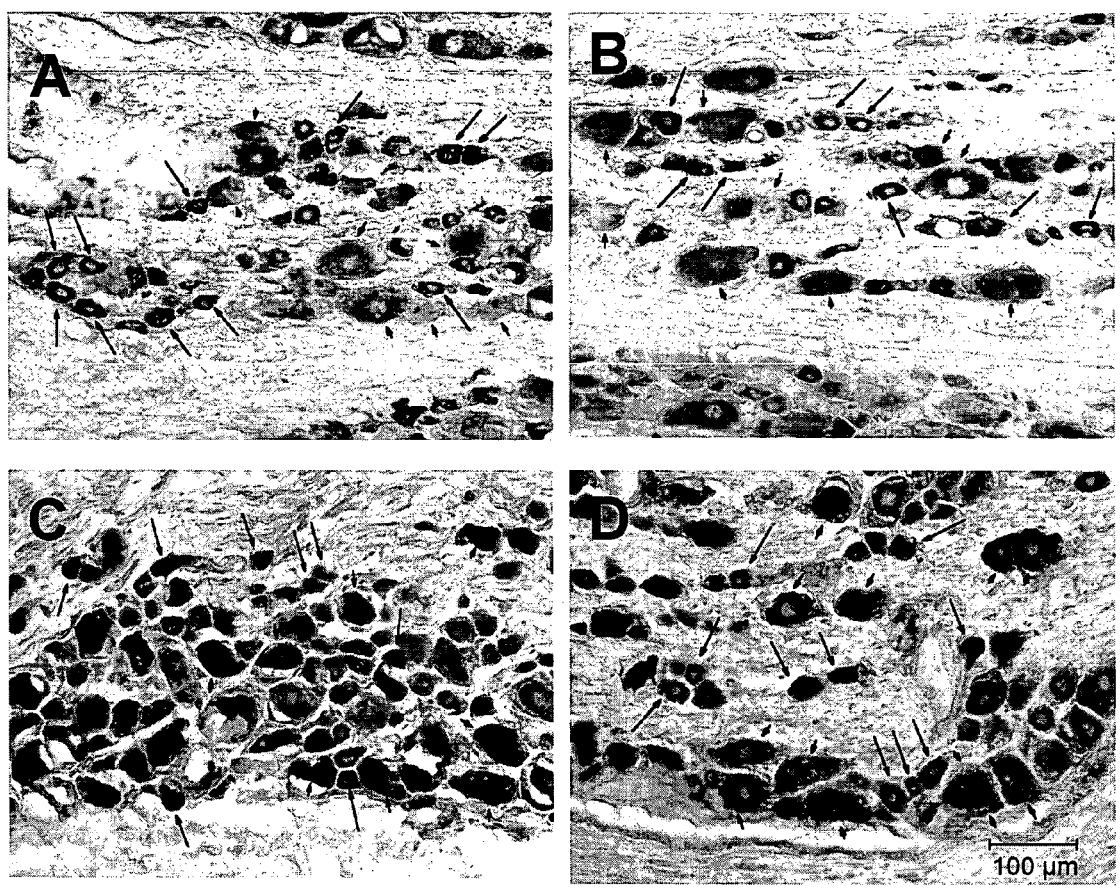
FIG. 3 are photomicrographs illustrating the effects of fixation onglutaminase (GT) immunoreactivity (IR) in the rat dorsal root ganglia (DRG). DRG sections were processed simultaneously with a mouse monoclonal GT antibody (A,C) or a rabbit polyclonal GT antiserum (B,D). Some DRG's (A,B) were fixed with 4% paraformaldehyde and others (C,D) were fixed with 70% picric acid and 0.2% paraformaldehyde. In paraformaldehyde fixed tissue, intense GT-IR was restricted to small sized DRG neurons (long arrows) with both GT antibodies (A,B). Large to medium sized neurons (short arrows) were lightly stained (A,B). In picric acid—paraformaldehyde fixed tissue, small (long arrows) and medium to large sized neurons (short arrows) contained intense GT-IR with both GT antibodies (C,D). For FIG. 4 and the data utilized to produce FIGS. 5 and 6, picric acid—paraformaldehyde fixed tissue was used with the rabbit polyclonal GT antiserum.

In normal rats, GT-IR in the DRG was evaluated with 2 fixatives and 2 antibodies. With a 4% PFA fixative, small (100-600 $\mu m^2$) neuronal cell bodies were labeled intensely with GT-IR (FIGS. 3A, 3B). With the 70% PA, 0.2% PFA fixative, the majority of DRG neuronal cell bodies were labeled with both GT antibodies (FIG. 3C, 3D). The PA-PFA fixative was used for the remainder of the experiments described herein.

Figure 4:
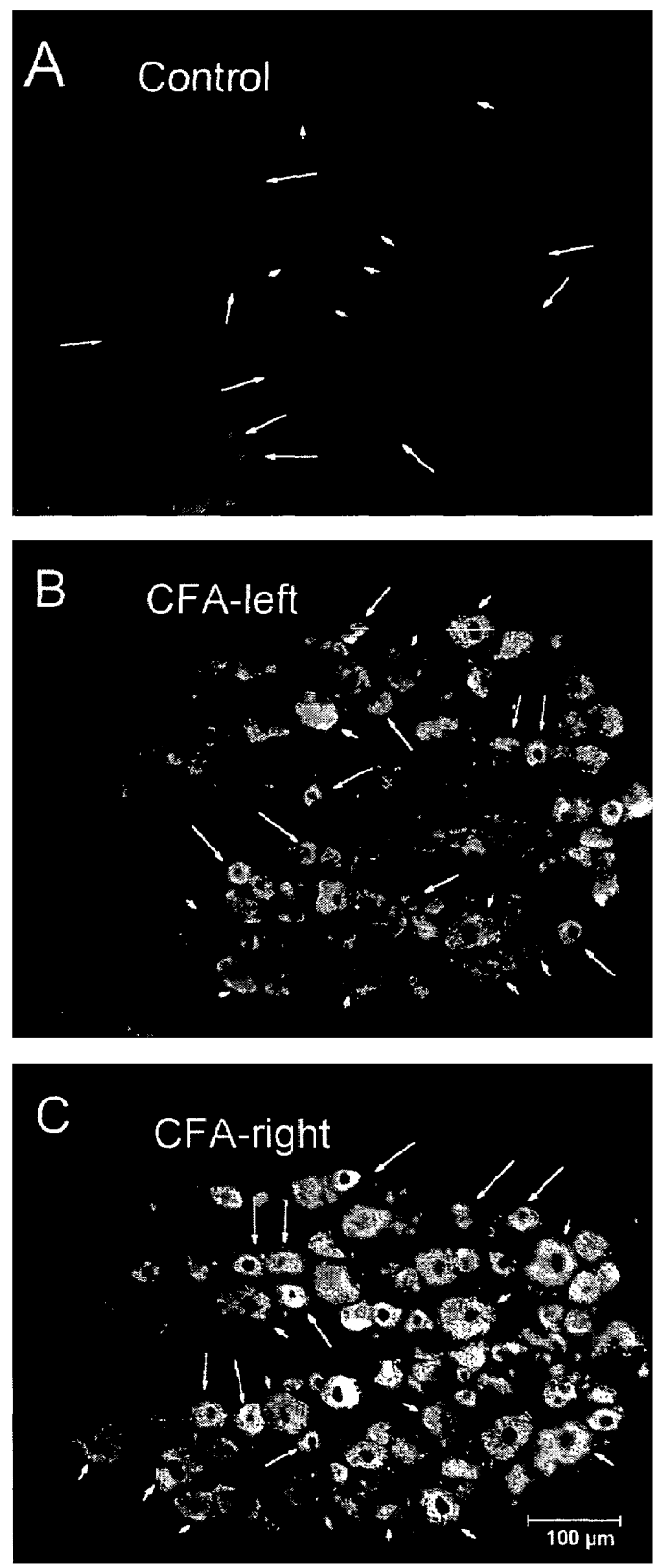
FIG. 4 are photomicrographs illustrating Glutaminase (GT) immunoreactivity (IR) in rat $L_4$ dorsal root ganglia (DRG) following 7 days of CFA inflammation in the right hindpaw. DRG sections were processed simultaneously with a rabbit polyclonal GT antiserum and photographed under identical conditions. (A) In control sections, GT-IR was light to moderate in all neuronal cell sizes, small (long arrows) and medium to large (short arrows). (B) Increased GT-IR intensity was observed in small (long arrows) and medium to large neurons (short arrows) in the left (contralateral) DRG following right hindpaw inflammation. This modest increase of GT-IR was observed in the left DRG at 3 & 10 days, also. (C) Elevated GT-IR in small (long arrows) and medium to large (short arrows) neurons occurred in the right (ipsilateral) DRG following CFA inflammation of right hindpaw. This pattern also was observed at 3 & 10 days following inflammation.

By 3 days following CFA inflammation, right DRG cell bodies from the CFA injected rats had a marked increase in GT-IR over the left DRG and control DRG cell bodies. At 7 days, CFA rats showed the same pattern of differences as the three day rats. The qualitative differences in the intensities, however, among the control, left and right DRG cell bodies were much greater (FIG. 4). Control DRG cell bodies had a light amount of GT-IR (FIG. 4A). The left DRG cell bodies from CFA rats (FIG. 4B) showed an increase in GT-IR compared to control DRG cell bodies, whereas the right DRG cell bodies contained the greatest amount of GT-IR (FIG. 4C). Similar to the three and seven day rats, the ten day CFA rats showed the same GT-IR intensity patterns among the control, left, and right DRG cell bodies.

Figure 5:
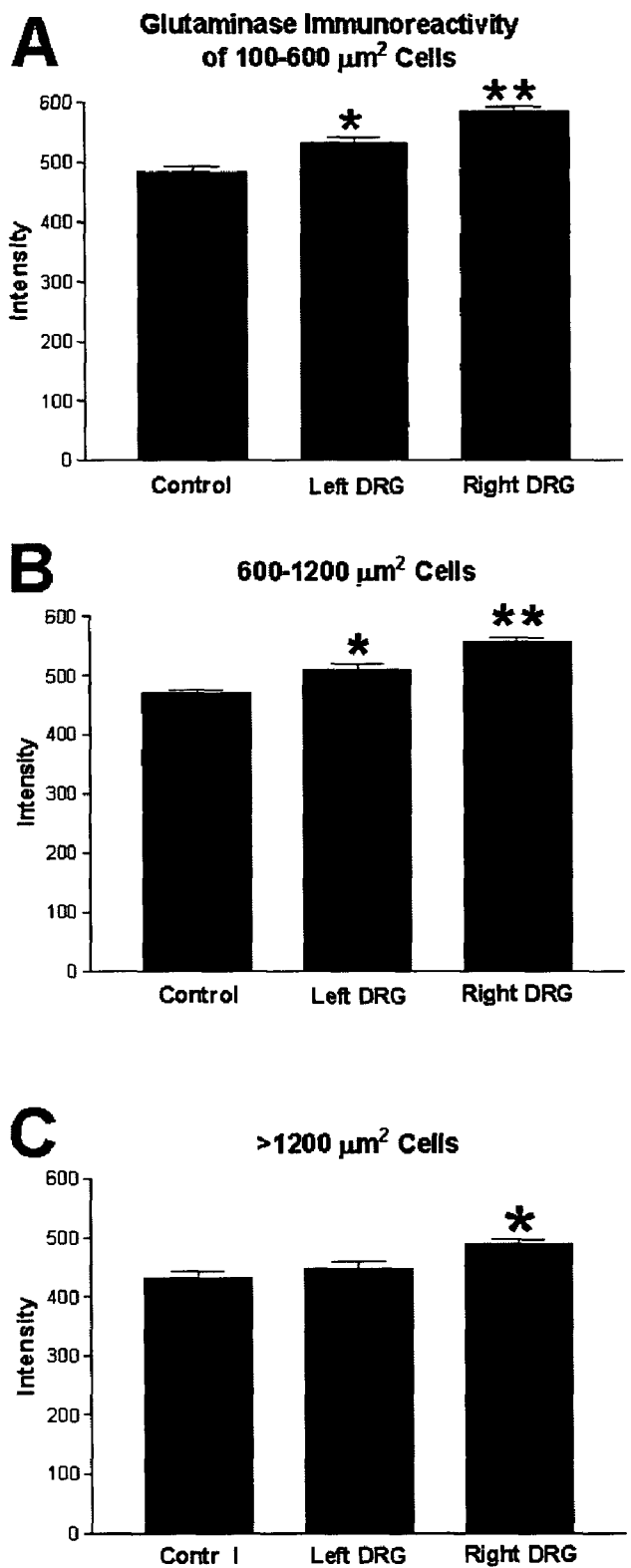
FIG. 5 is a graphic illustration of an image analysis of glutaminase (GT) immunoreactivity (IR) in $L_4$DRG neurons after 7 days of CFA inflammation in the right paw. Data are presented as intensity divided by the area of the cell. DRG neurons were categorized into three area size groups: (A) small—100-600 $\mu m_2$, (B) medium—600-1200 $\mu m_2$, (C) large—>1200 $\mu m_2$. (A) Small sized neurons in the left DRG contained a significantly greater immunoreactive signal (*, $p<0.05$) than controls. Neurons in the right DRG were more intensely stained than left DRG or controls (**, $p<0.01$). (B) Medium sized neurons in the left DRG contained a significantly greater immunoreactive signal (*, $p<0.05$) than controls. Neurons in the right DRG were more intensely stained than left DRG or controls (**, $p<0.01$). (C) In the right DRG, large sized neurons were more intensely stained than the left DRG or controls (*, $p<0.05$).

The seven day rat immunohistochemistry images were analyzed with the SCION image analysis program in order to quantify the GT-IR intensities of three different sizes of DRG cell bodies (FIG. 5). The small (100-600 $\mu m^2$) DRG cell bodies showed the greatest amount GT-IR/area and the largest differences in intensities among control, left, and right cell bodies of the three different DRG cell sizes. The small DRG cell bodies had intensities of $484.6\pm2.0/\mu m^2$ for controls, nerve plexus and papillae from rats with inflammation. In addition, many glutamate and GT immunoreactive fibers were found to leave the dermis to enter the epidermis in the inflamed paw.

Once it was determined that GT levels were elevated at the neuronal cell body and peripheral fibers and in response to chronic inflammation, several GT inhibitors were examined for their ability to alleviate nociceptive responses to thermal and mechanical stimuli. Several compounds inhibit GT enzyme activity (Shapiro et al., 1978, 1979; Kvamme et al., 1975, 1991; Kvamme & Torgner, 1975; Curthoys & Watford, 1995), including 6-diazo-5-oxo-L-norleucine (DON) and N-ethylmaleimide (NEM). DON irreversibly binds to the glutamine binding site of GT (Shapiro et al., 1979), whereas NEM partially inhibits GT via interaction with the glutamate binding site (Kvamme & Olsen, 1979; Kvamme & Lenda, 1982). Intraparenchymal or ICV injection of DON inhibits GT and causes a decrease in glutamate and GT for several days in rat brain until neurons synthesize new GT (Bradford et al., 1989; Kaneko et al., 1992; Conti & Minelli, 1994). Therefore, DON and NEM were administered peripherally during chronic inflammation to observe the effect of GT enzyme inhibition on nociceptive responses.

Figure 7A:
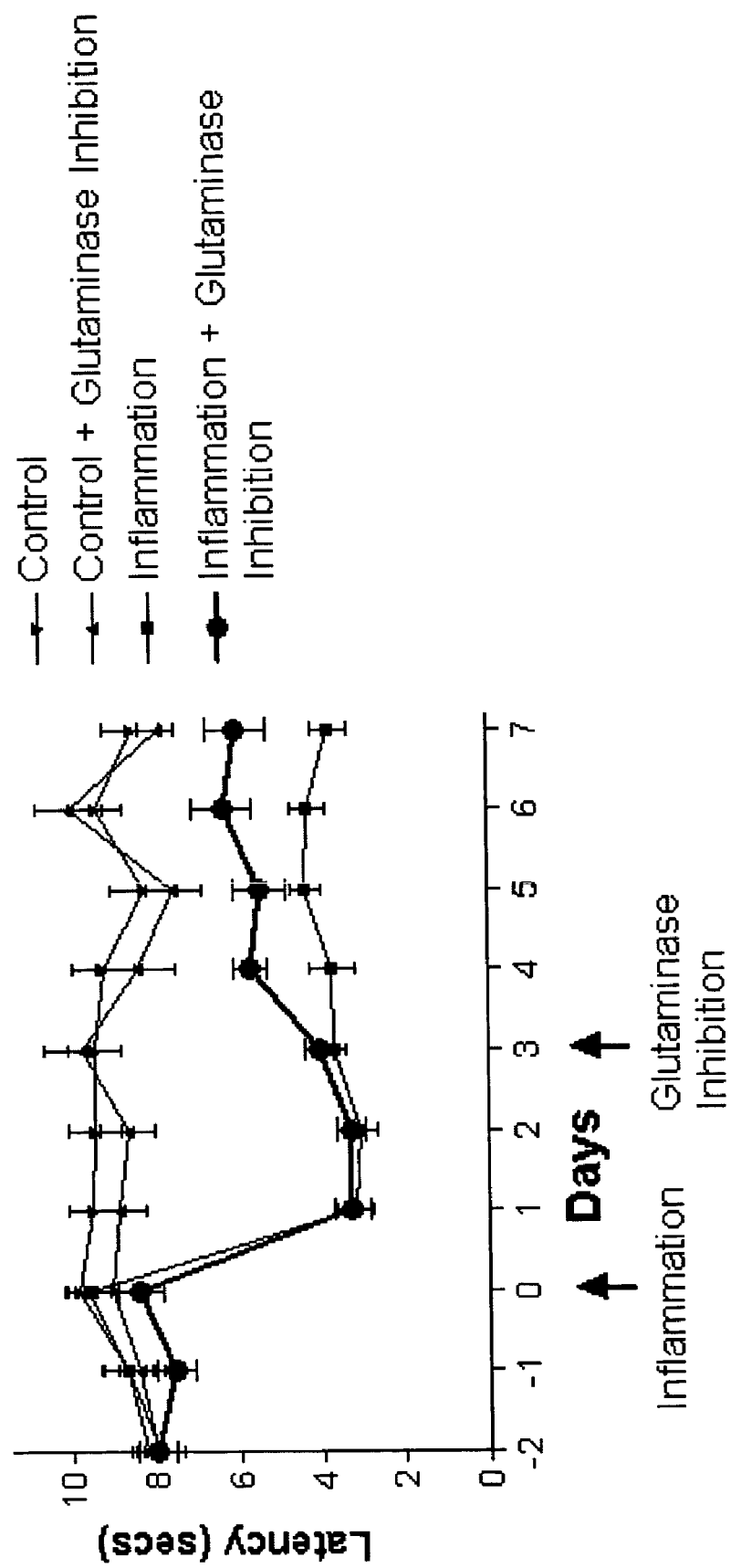
FIG. 7 is a graphic representation of the effects of inhibition of glutaminase on thermal and mechanical pain. The hindpaw responses to thermal stimulation (FIG. 7A) and pressure sensitivity (FIG. 7B) were determined for a control rat, a control rat following glutaminase inhibition with 6-diazo-5-oxo-L-norleucine (DON), a rat after CFA inflammation, and a rat after CFA inflammation and following glutaminase inhibition with DON.
Figure 7B:
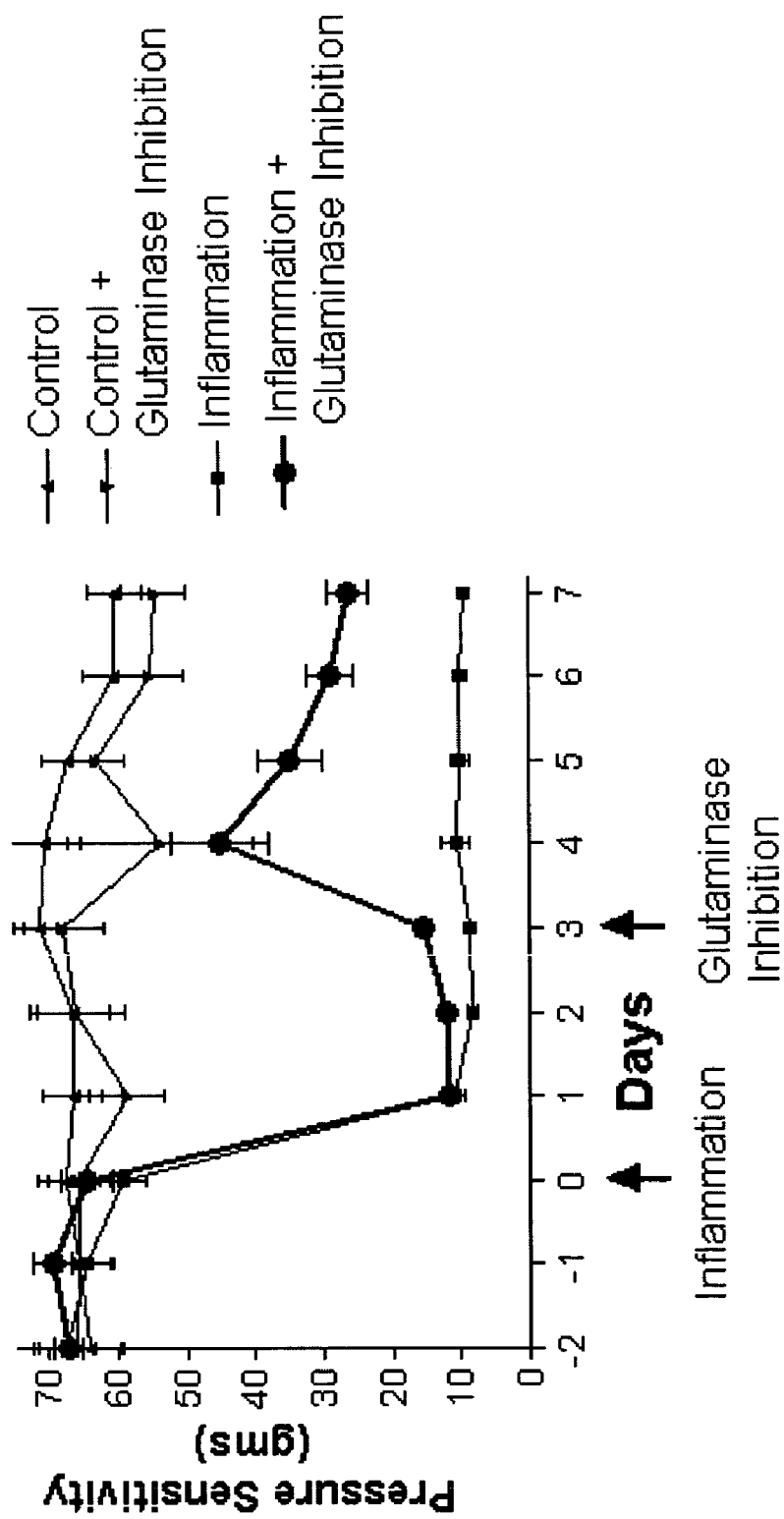

Following inflammation of the rat paw with complete Freund's adjuvant (CFA), DRG neurons increase glutaminase (GT) production for shipment to peripheral terminals causing elevated glutamate (GLU) levels in skin and joints. Increased glutamate release may be responsible for maintaining thermal hyperalgesia and/or mechanical allodynia. In the present invention, the effects of several GT inhibitors, including 6-diazo-5-oxo-Lnorleucine (DON) and N-ethylmaleimide (NEM), were examined following inflammation. In FIG. 7, CFA:saline or saline was injected (75-100 µl) into the right footpad of adult male Sprague Dawley rats. After 2-3 days, DON or saline was injected (25 µl) into the right paw.

The hindpaw responses of rats to thermal stimulation and pressure sensitivity were determined in control and CFA rats, as well as control and CFA rats treated with the glutaminase inhibitor DON (FIG. 7). Paw pressure withdrawal thresholds (PPWT) were evaluated with Von Frey hairs. In rats with CFA+saline, PPWT were reduced from 50-70 g (in control rats) to 5-12 g. For CFA+DON rats, PPWT were increased to 20-30 g starting from 6 hours through the duration of the experiment. For CFA+NEM rats, PPWT were increased to 20-25 g after 48 hours.

Figure 8A:
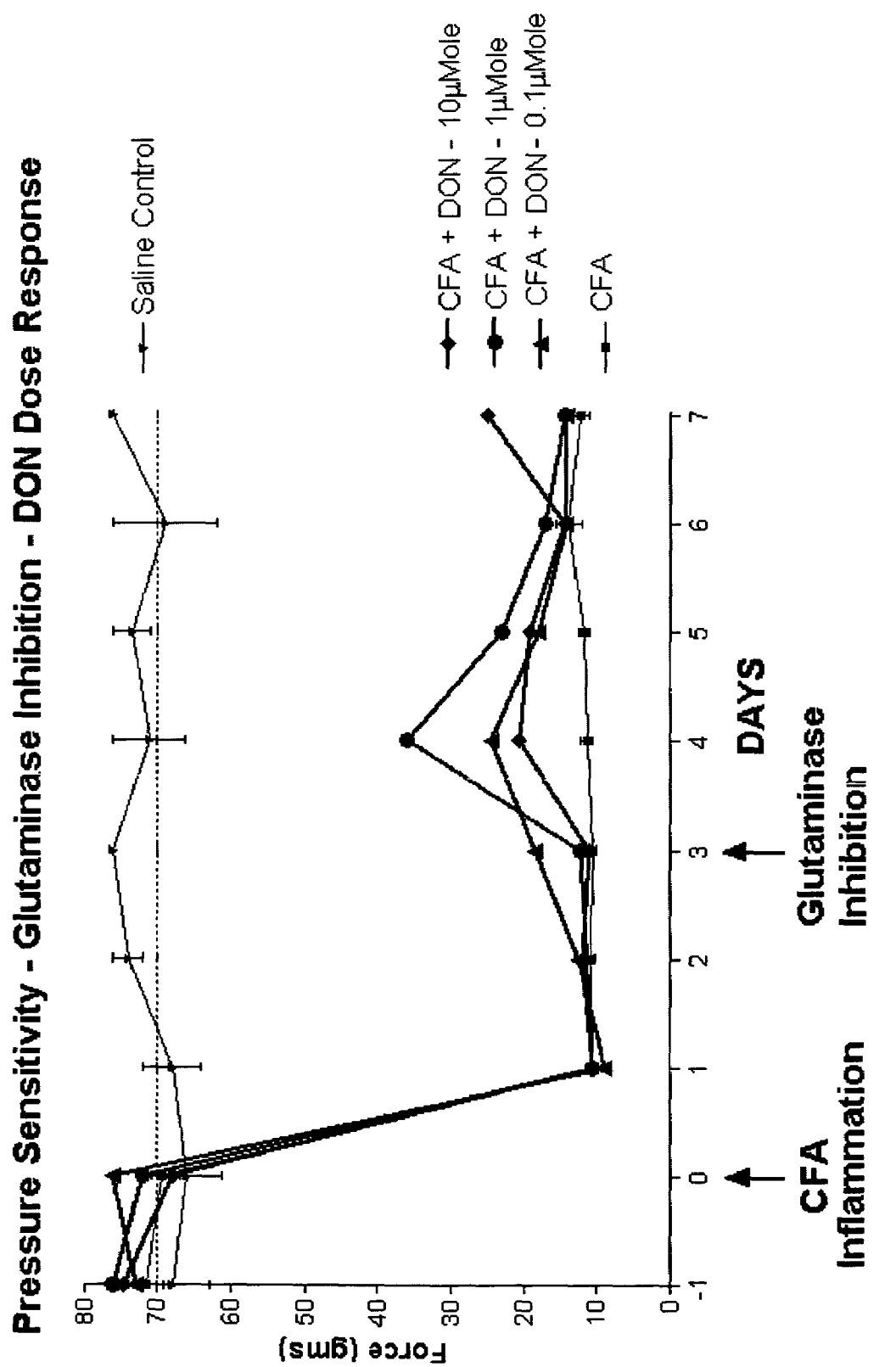
FIG. 8A is a graphic representation illustrating the efficacy of DON to provide long term pain relief from pressure (mechanical stimulation). After administration of DON at day three following CFA inflammation, pain relief occurred for several days with three different doses of DON (0.1-10 $\mu$Mole/25 $\mu$l).

In FIG. 8A, the efficacy of DON to provide long term pain relief to pressure (mechanical stimulation) was determined by using three different doses of DON (0.1-10 µMole/25 µl). After administration of DON at day three following CFA inflammation, pain relief occurred for several days with all three doses of DON.

Figure 8B:
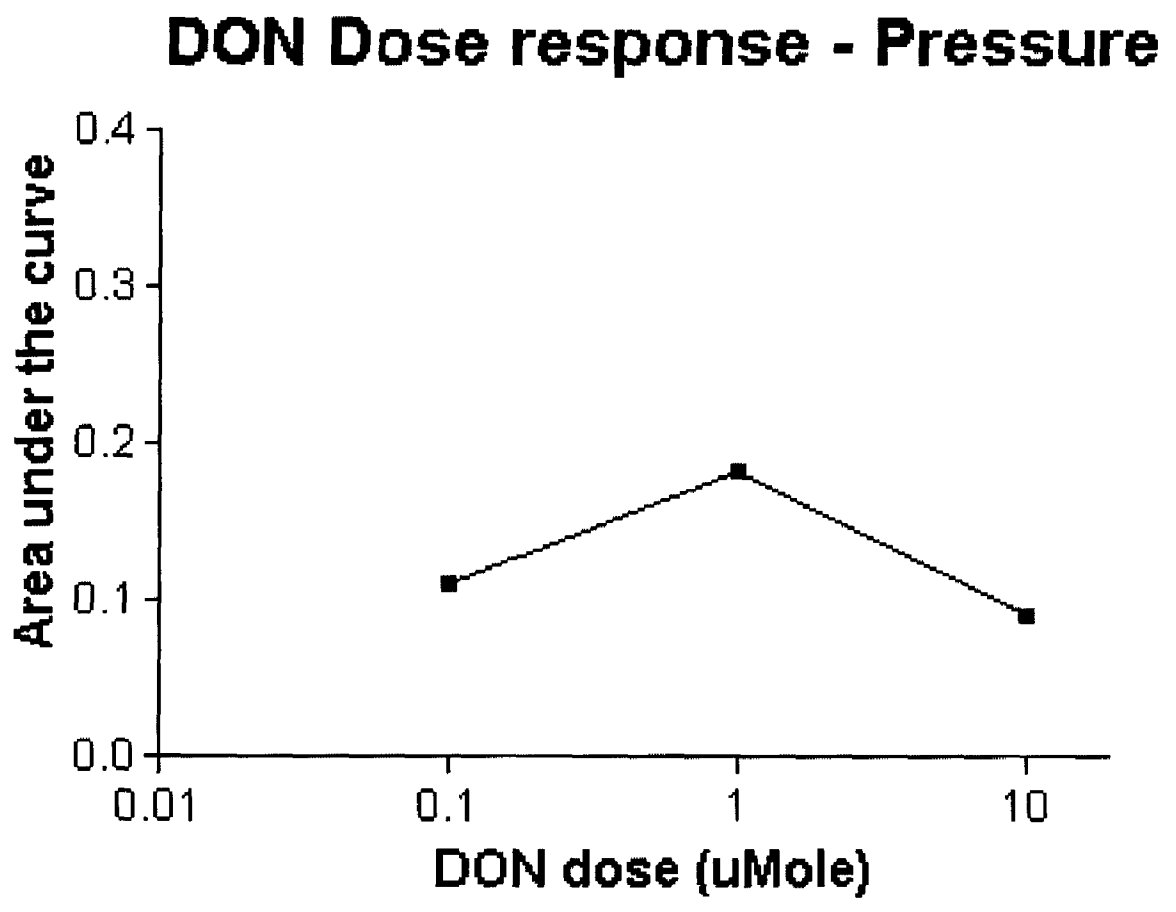

Based on the data in FIG. 8A, a dose response curve was constructed, as shown in FIG. 8B. The area under the curve for each dose was determined from Day 3 to Day 5. No differences in the amount of pain relief were determined for the doses tested (0.1-10 µMole/25 µl).

Figure 9A:
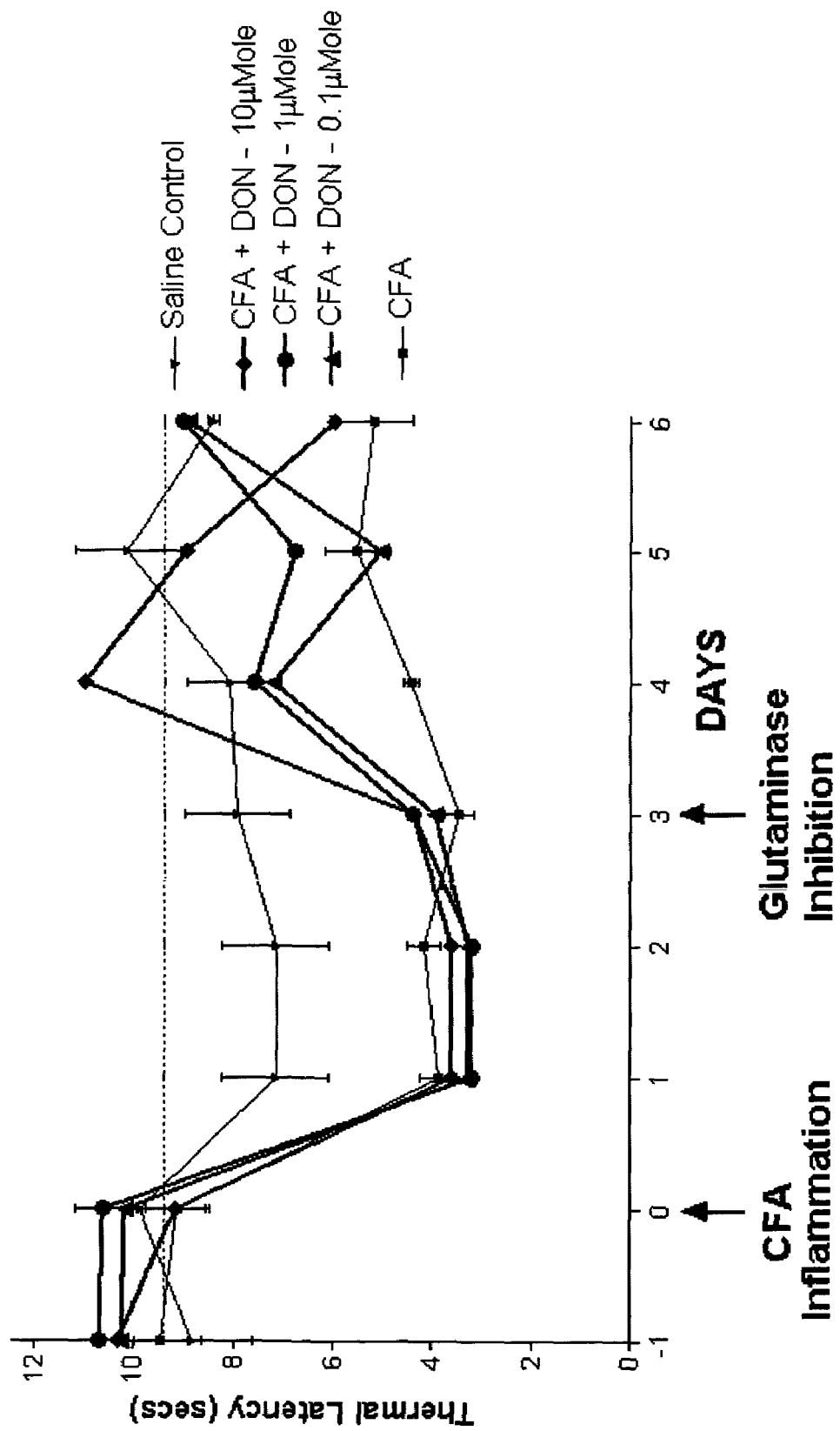
FIG. 9A is a graphic representation illustrating the efficacy of DON to provide long term pain relief to heat. After administration of DON at day three following CFA inflammation, pain relief occurred for several days with three different doses of DON (0.1-10 $\mu$Mole/25 $\mu$l).

In FIG. 9A, the efficacy of DON to provide long term pain relief to heat (thermal stimulation) was determined for the same three doses of DON (0.1-10 µMole/25 µl). After administration of DON at day 3 after CFA inflammation, pain relief occurred for several days with all three doses of DON. 10 µMole DON (♦ line) was most efficacious, bringing thermal responses back to normal for two days. The other two doses (0.1 and 1 µMole, ▲ and ● lines, respectively) provided pain relief to near normal levels for at least one day and then gave variable results for the next several days.

Figure 9B:
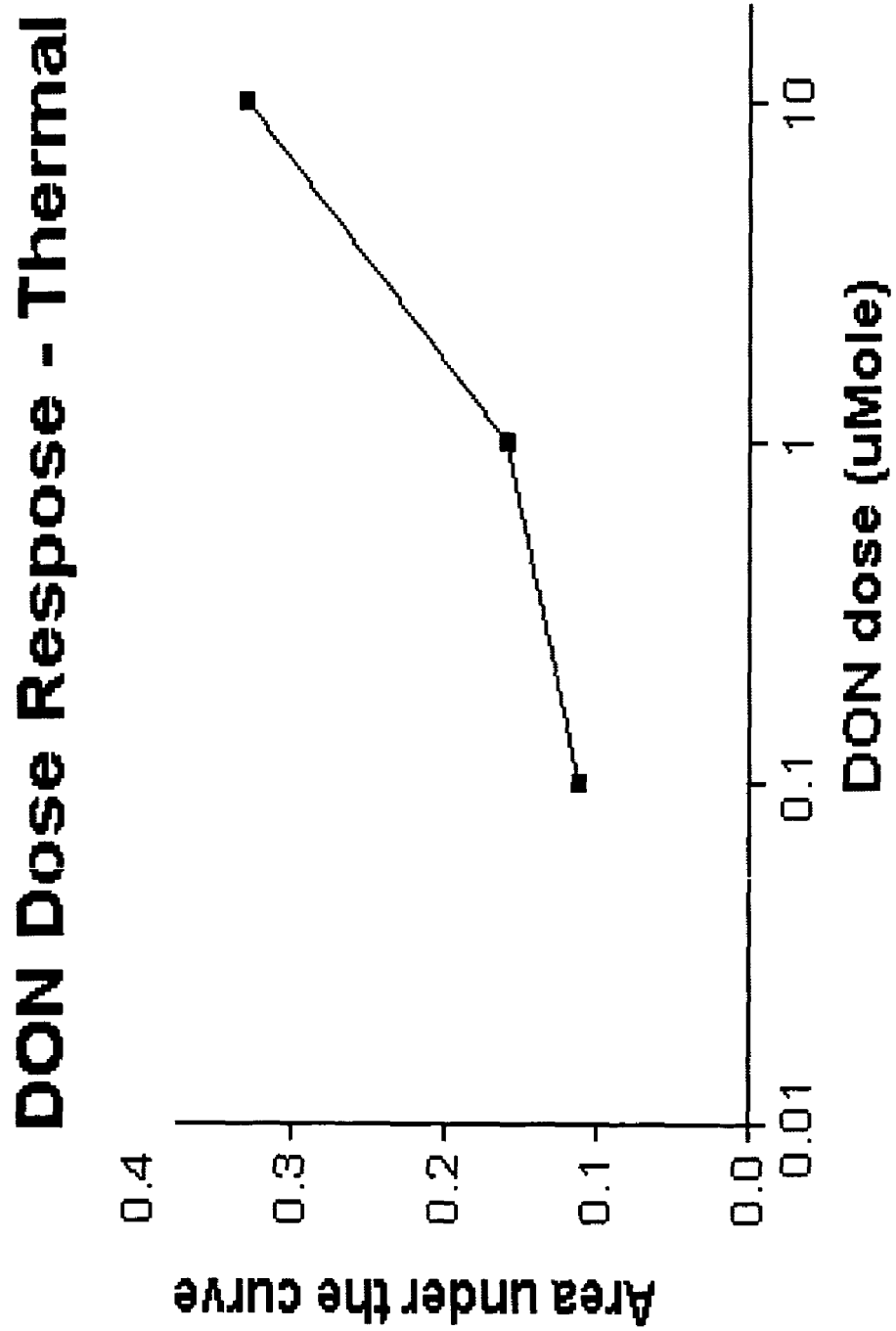
FIG. 9B is a graphic representation illustrating the DON dose response for pain relief from thermal stimulation. The area under the curve for each dose was determined from Day 3 to Day 5. Pain relief was most efficacious at the higher doses (1-10 $\mu$Mole/25 $\mu$l).

Based on the data in FIG. 9A, a dose response curve was constructed, as shown in FIG. 9B. The area under the curve for each dose was determined from Day 3 to Day 5. Pain relief was most efficacious at the higher doses (1-10 µMole/25 µl).

Figure 10A:
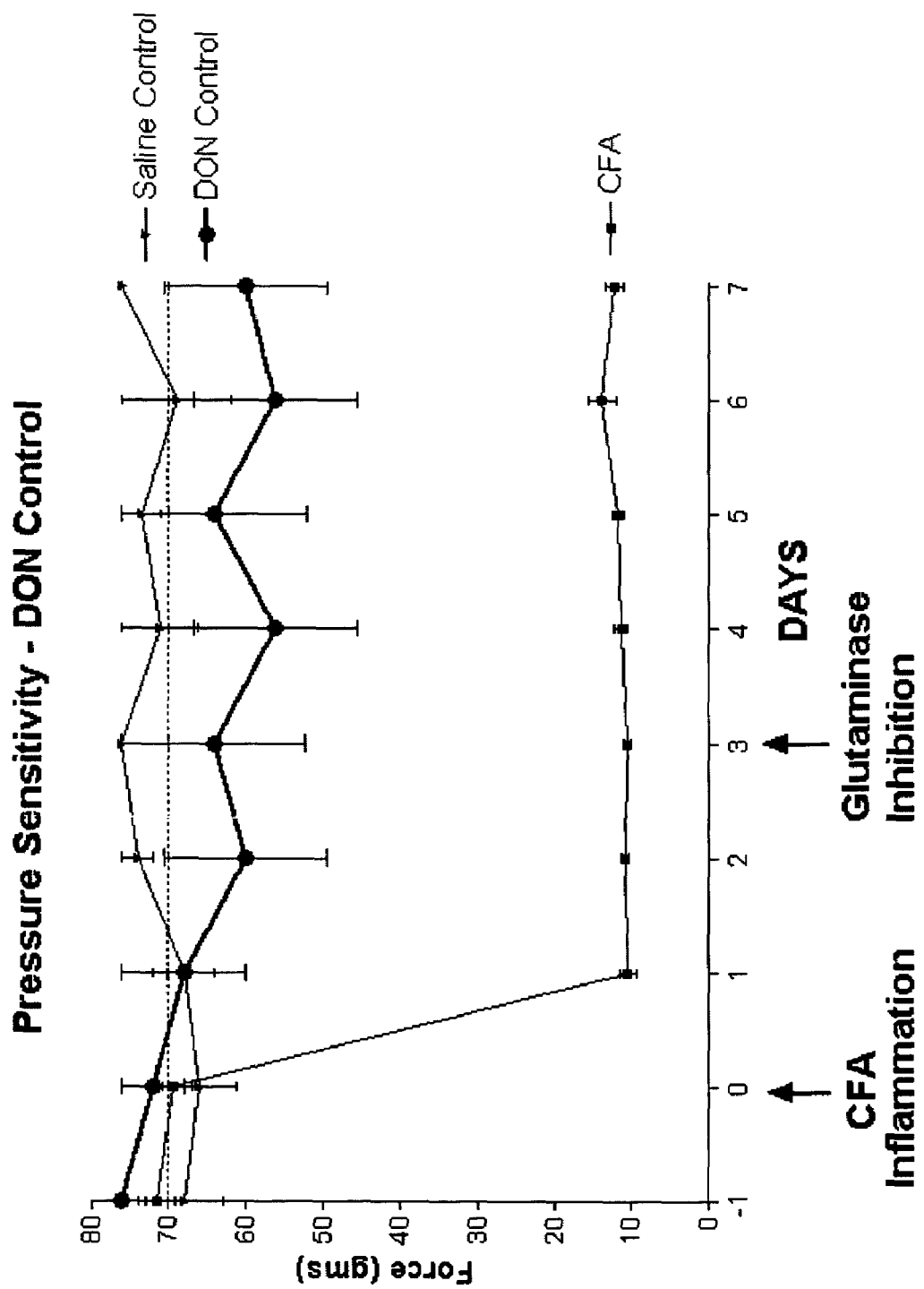
FIG. 10 are graphic representations illustrating that intraplantar injection of DON into the hindpaw of normal rats does not affect pressure or thermal senstivities. DON was injected (10 µMole/25 µl) on day three. Both the pressure (FIG. 10A) and thermal (FIG. 10B) sensitivities in DON-treated rats were the same as saline controls.
Figure 10B:
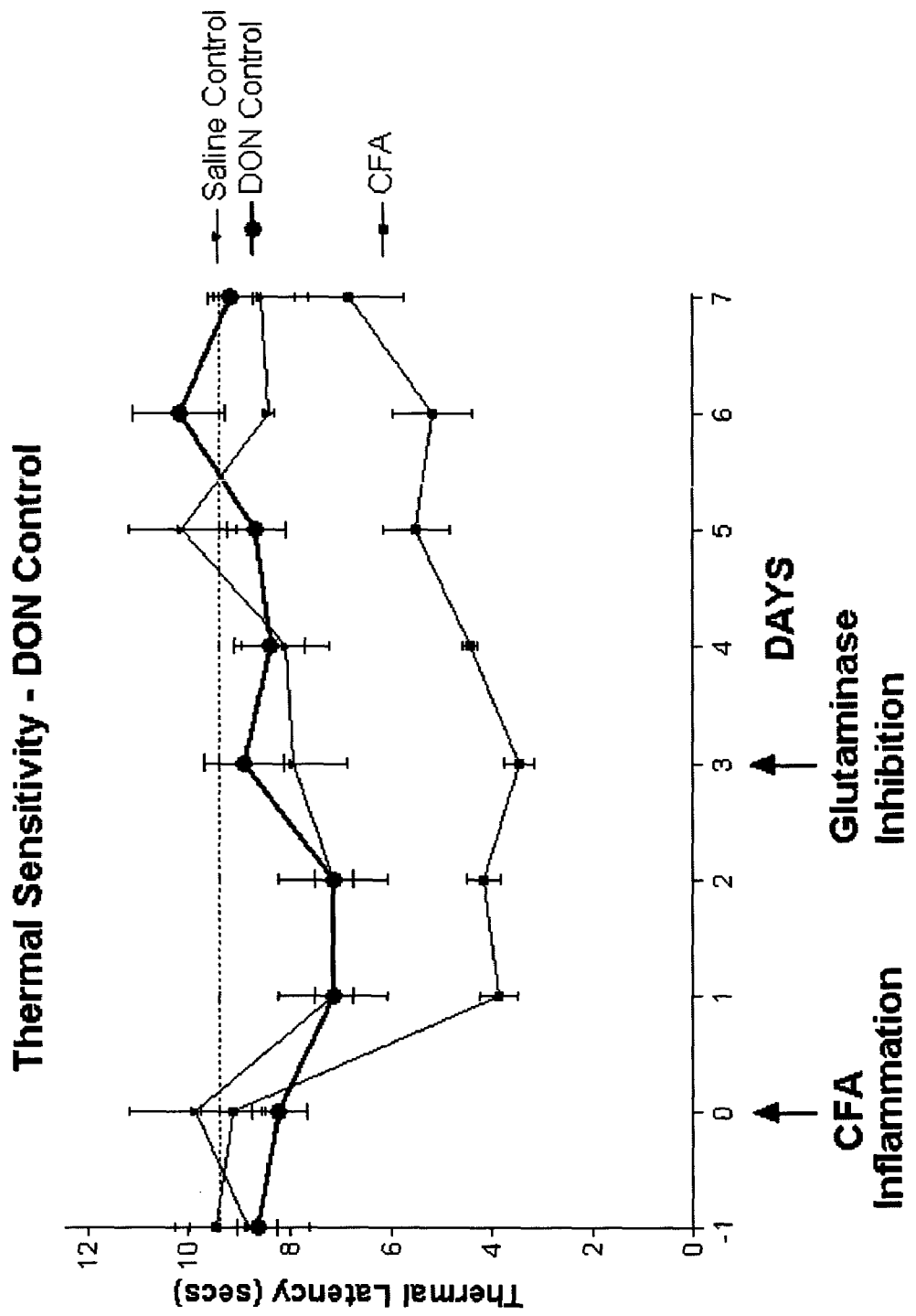

FIG. 10 illustrates DON controls. DON was injected (10 µMole/25 µl) on day 3, and such injection of DON does not affect thermal or pressure sensitivities. Both the pressure (FIG. 10A) and thermal (FIG. 10B) sensitivities in DON treated rats were the same as saline controls.

Figure 11A:
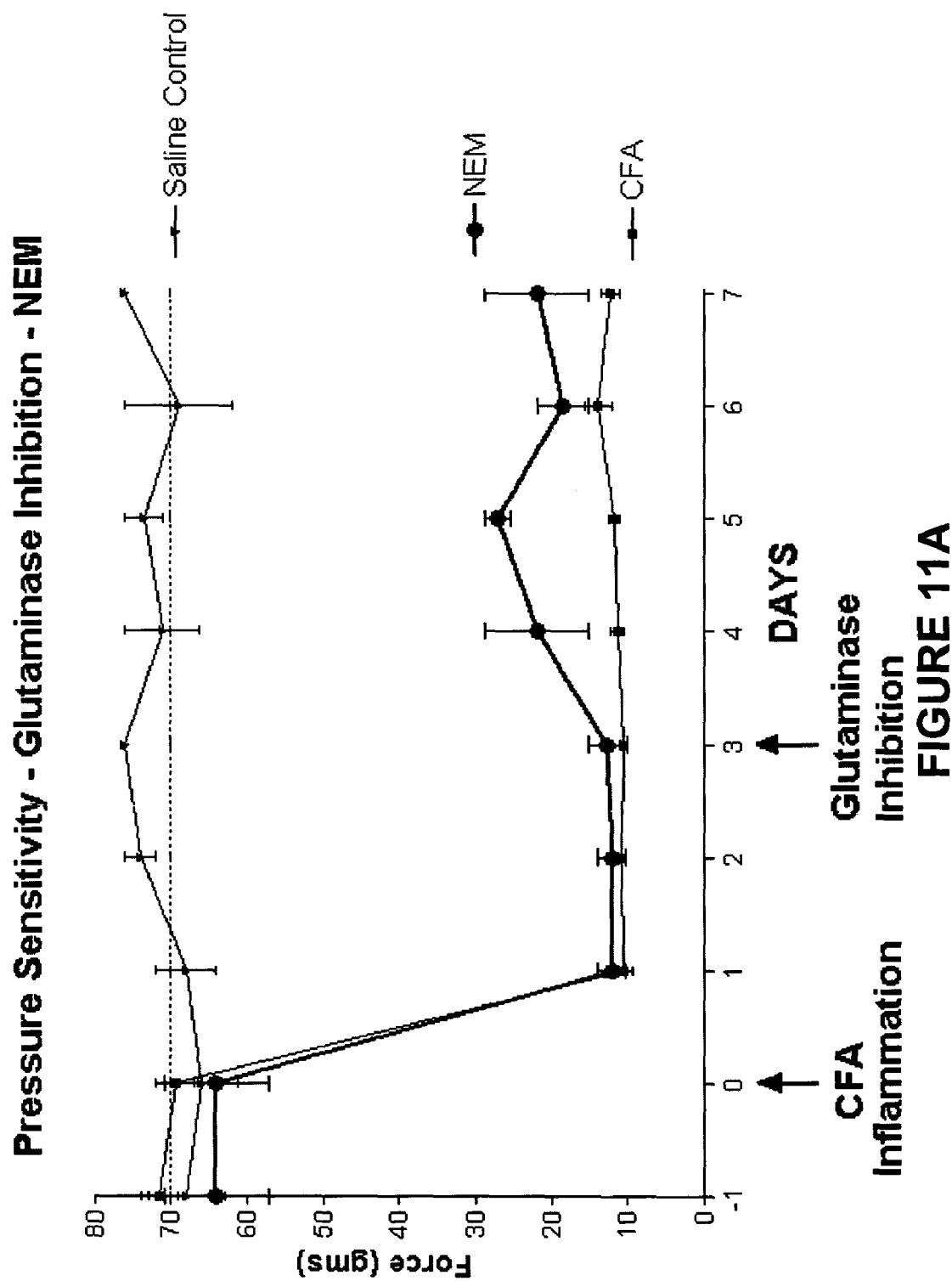
FIG. 11A is a graphic representation demonstrating the efficacy of N-ethylmaleimide (NEM) to provide long term pain relief to pressure (mechanical stimulation). After administration of NEM (10 mM/25 µl) at day three following CFA inflammation, pain relief occurred for several days.
Figure 11B:
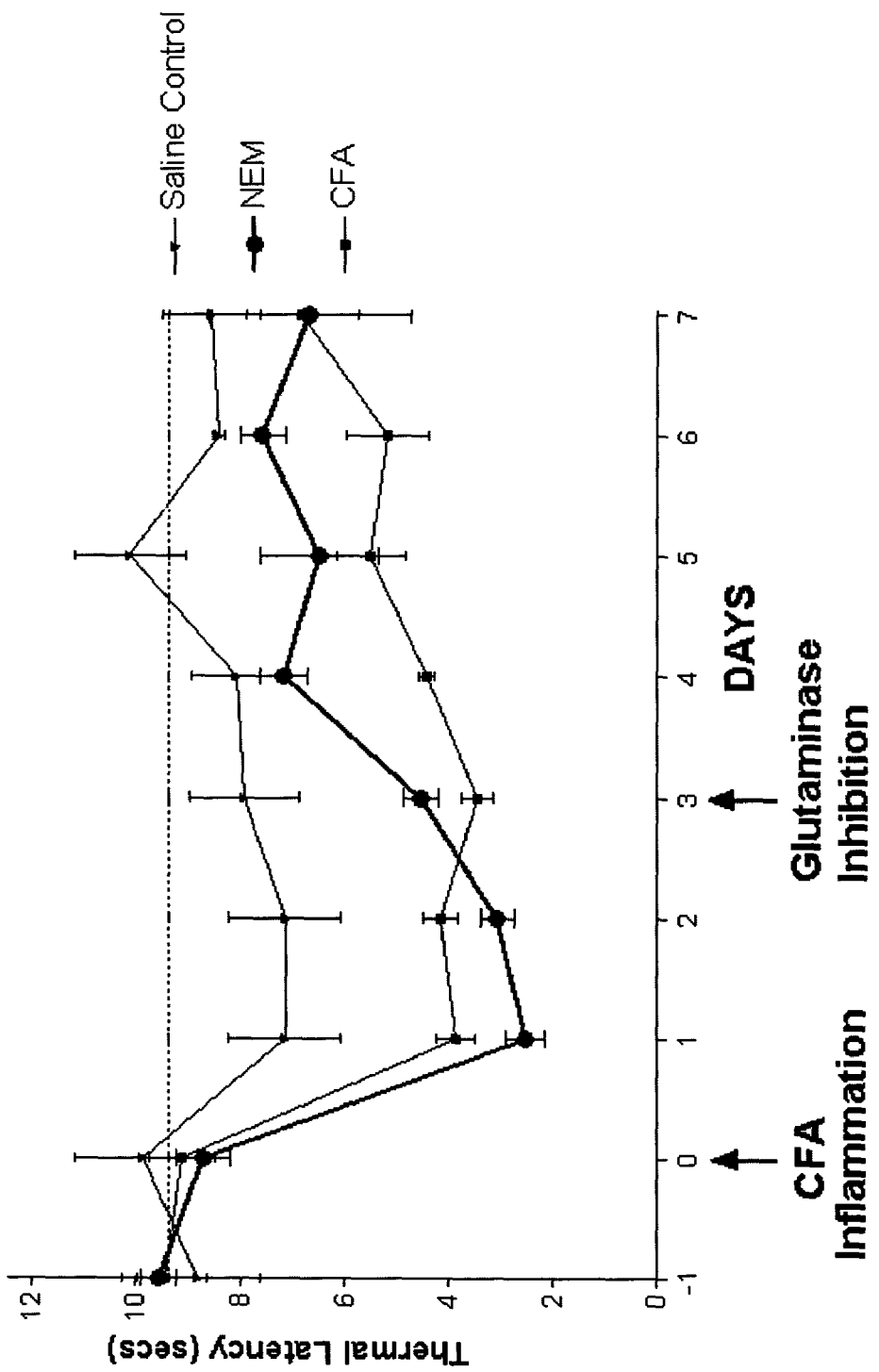
FIG. 11B is a graphic representation illustrating the efficacy of NEM to provide long term pain relief from heat. After administration of NEM (10 mM/25 µl) at day three following CFA inflammation, pain relief occurred to near normal levels at days 4 and 6.

A second GT inhibitor, N-ethylmaleimide (NEM), was also evaluated to determine its effects on GT enzyme inhibition and nociceptive response in the chronic inflammation model described above. NEM is a GT inhibitor that binds to the glutamate site of the enzyme. FIG. 11 illustrates that NEM is effective in providing long term pain relief to pressure (mechanical stimulation, as shown in FIG. 11A) and heat (thermal stimulation, as shown in FIG. 11B). After administration of NEM (10 mM/25 µl) at day three following CFA inflammation, pain relief occurred for several days in response to mechanical stimulation (FIG. 11A), while pain relief occurred to near normal levels at days four and six for thermal stimulation (FIG. 11B).

The skin from the hindpaws were also processed for GLU and GT immunohistochemistry after 7 days (FIG. 12). Control rats had very little GLU or GT-immunoreactive (IR) fibers in the paw skin. Skin from CFA+saline rats contained many intense GLU-IR and GT-IR fibers. Skin from CFA+DON or CFA +NEM rats had moderate numbers of GLU-IR and GT-IR fibers.

Figure 13A:
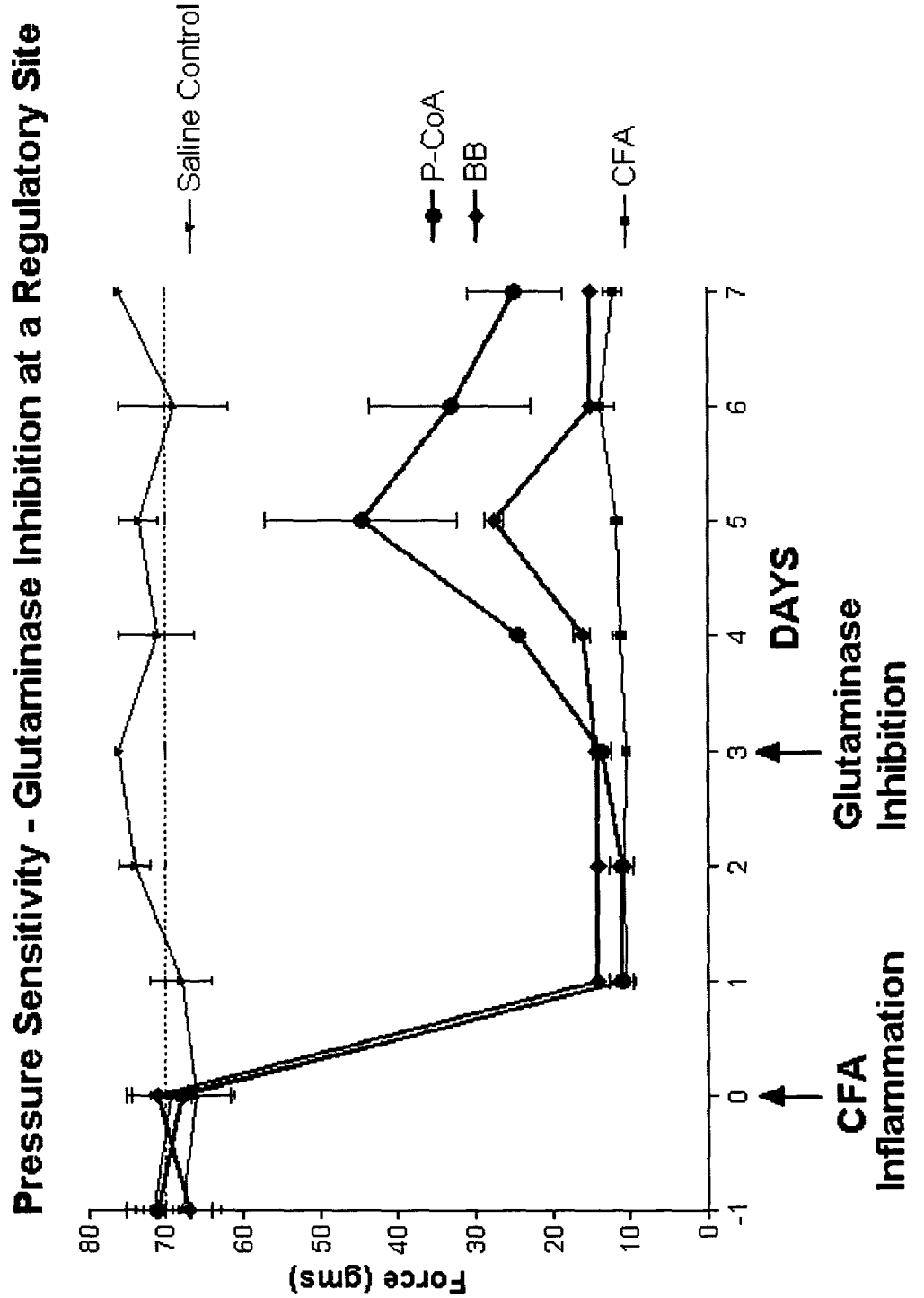
FIG. 13A is a graphic representation demonstrating the use of two inhibitors at regulatory sites on glutaminase and their efficacy to provide long term pain relief to pressure (mechanical stimulation). After administration of Palmitoyl Coenzyme A (P-CoA, 2 mM/25 µl) or bromothymol blue (BB, 200 µM/25 µl) at day three following CFA inflammation, pain relief occurred for several days.
Figure 13B:
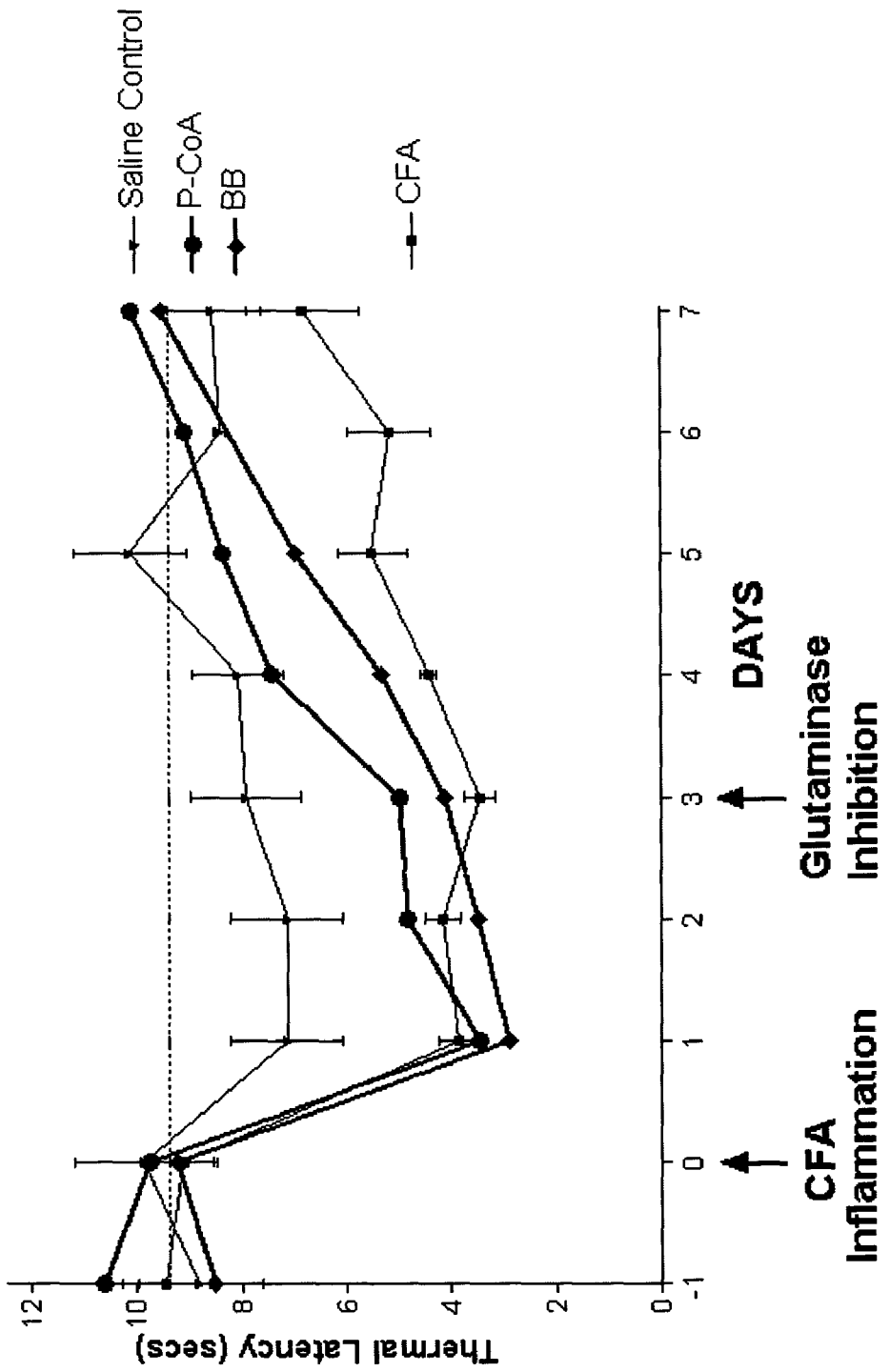
FIG. 13B is a graphic representation illustrating the efficacy of P-CoA and BB to give long term pain relief to heat. After administration of P-CoA (2 mM/25 µl) at day three following CFA inflammation, pain relief occurred to near normal levels from Days 4-7. After BB (200 µM/25 µl), pain relief occurred from Days 5-7 and at near normal levels from Days 6-7.

Two other GT inhibitors, BB and P-CoA, were also evaluated to determine their effects on GT enzyme inhibition and nociceptive responses in the chronic inflammation model described above. P-CoA and BB are inhibitors of GT at regulatory sites on the enzyme. P-CoA (2 mM/25 µl) or BB (200 µM/25 µl) was administered at day three following CFA inflammation, and both were shown to be effective in providing long term pain relief to pressure (mechanical stimulation, as shown in FIG. 13A) and heat (thermal stimulation, as shown in FIG. 13B). In FIG. 13A, P-CoA (● line) provided pain relief from Days 4-7, whereas BB (♦ line) gave pain relief on Day 5. In FIG. 13B, P-CoA provided pain relief to near normal levels from Days 4-7, while BB provided pain relief from Days 5-7 and at near normal levels from Days 6 and 7.

Figure 14:
FIG. 14 are photomicrographs illustrating that glutaminase production in many cells is regulated by zeta-crystallin: quinone oxidoreductase (ZC).

FIG. 14 illustrates that glutaminase production in many cells is regulated by zeta-crystallin:quinone oxidoreductase (ZC). In FIGS. 14A-C, ZC levels are modified during chronic inflammation. ZC-immunoreactivity (IR) was examined in the rat $L_4$DRG during inflammation at an early and later time point (2, 6 days). ZC-IR in DRG neurons of control rats (A) shows a moderate staining of the cytoplasm of all neurons. Following inflammation for 48 hrs., ZCIR is elevated in the cytoplasm and now appears in the nuclei of many neurons (arrows). ZC-IR remains elevated at 6 days of inflammation and occurs mainly in the cytoplasm, although some nuclei (arrows) contain light ZC-IR. The increase in ZC precedes elevated amounts of glutaminase in DRG neurons during inflammation. These results are consistent with ZC's role as a stabilizer of glutaminase mRNA during times of cellular stress. Increased production of ZC during inflammation appears important for stabilization of glutaminase mRNA and elevated glutaminase production.

Figure 15:
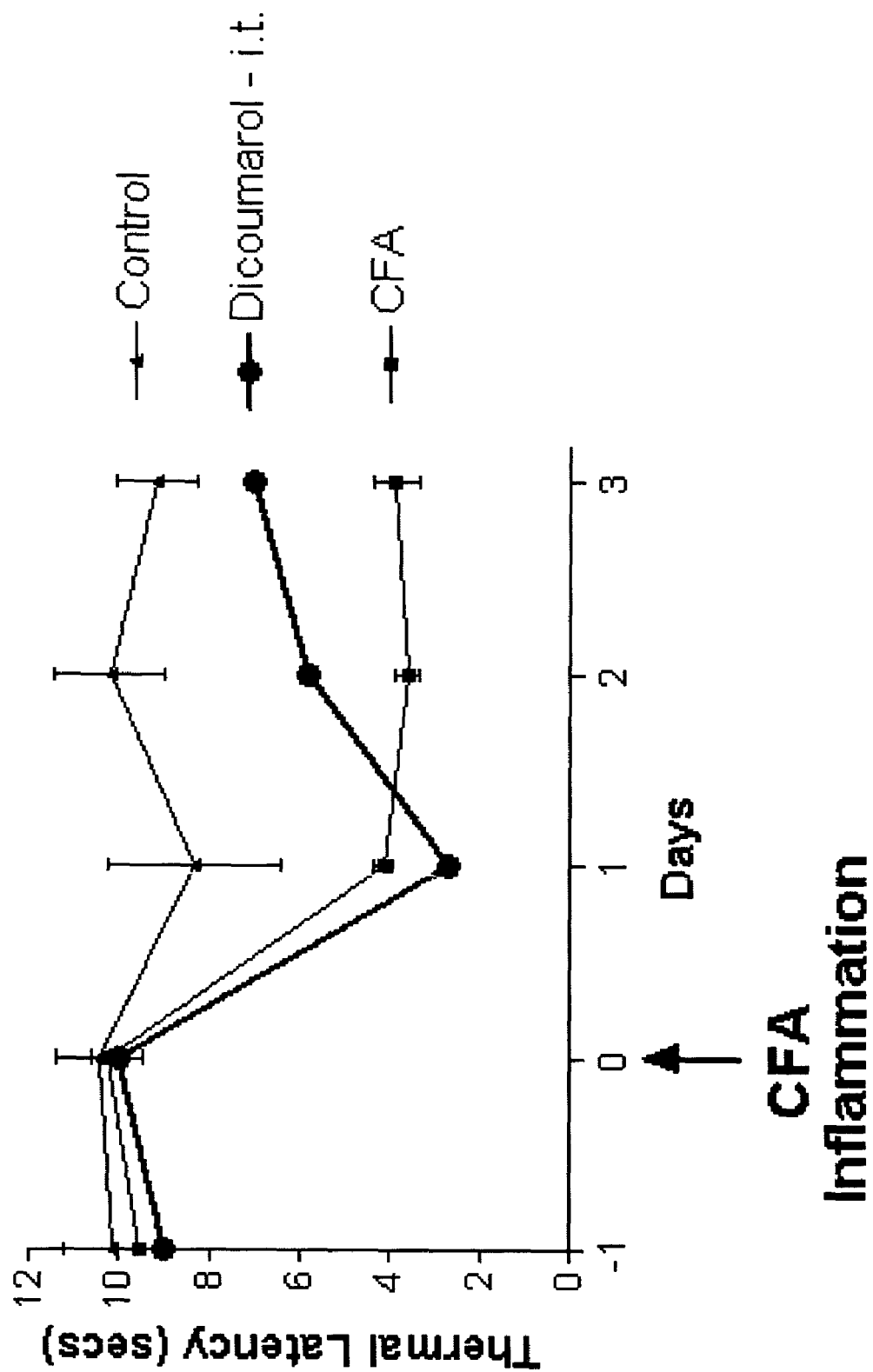
FIG. 15 is a graphic representation that illustrates that dicoumarol, a ZC inhibitor, disrupts increased glutaminase production during chronic inflammation and decreases the prolonged hyperalgesia of chronic inflammation. Inflammation was initiated with complete Freund's adjuvant (CFA) at Day 0, and dicoumarol (15 µl © 500 µM) or saline was administered intrathecally on days 0, 1 and 2. Thermal latencies and pressure responses (not shown) were recorded, and both the groups with inflammation (CFA) and inflammation plus dicoumarol (CFA+DC) experienced hyperalgesia and allodynia during acute inflammation (Day 1). As inflammation progressed, however, the responses of CFA+DC rats became less hyperalgesic and allodynic. At Day 3, the DRG's from the rats were collected and processed for glutaminase and ZC-IR, as shown in FIG. 16.
Figure 16:
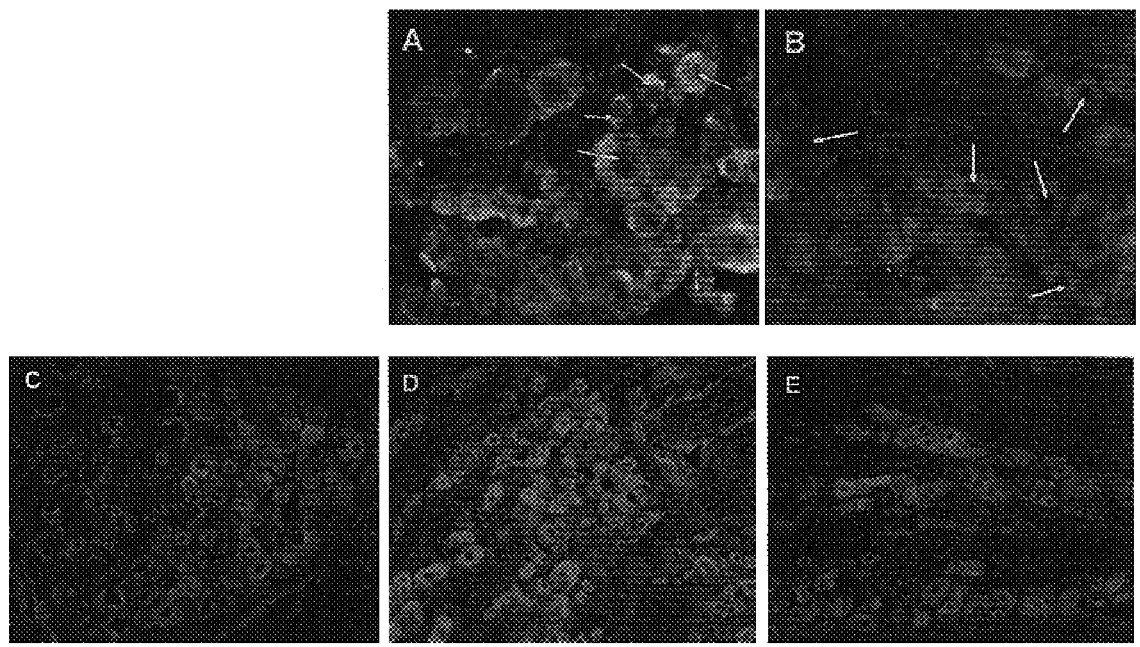
FIG. 16 are photomicrographs illustrating that dicoumarol inhibits ZC and glutaminase production. In the DRG, ZC-IR was elevated (A) in rats with inflammation, but the ZC-IR (B) from rats treated with DC during inflammation was similar to controls. ZC-IR was found in the cytoplasm and nuclei (arrows) from rats with inflammation, whereas in rats treated with DC during inflammation, the nuclei (arrows) were not stained and ZC-IR was found primarily in the cytoplasm. In the DRG, glutaminase-IR was observed at moderate levels from controls (C), elevated following inflammation (D), and similar to controls in rats treated with DC during inflammation (E).

In FIGS. 15 and 16, dicoumarol, a ZC inhibitor, is shown to disrupt increased glutaminase production during chronic inflammation and decrease the prolonged hyperalgesia of chronic inflammation. Since ZC stabilizes glutaminase mRNA, then inhibition of ZC should not allow neurons to increase glutaminase production during inflammation. Intrathecal (i.t.) cannulae were implanted to the L4 DRG, and rats recovered several days. Inflammation was initiated with complete Freund's adjuvant (CFA) at Day 0 and dicoumarol (15 µl @ 500 µM) or saline was administered i.t. on days 0, 1 and 2. Thermal latencies (FIG. 15) and pressure responses (not shown) were recorded. Both the groups with inflammation (CFA) and inflammation plus dicoumarol (CFA+DC) experienced hyperalgesia and allodynia during acute inflammation (Day 1). As inflammation progressed, however, the responses of CFA+DC rats became less hyperalgesic and allodynic. At Day 3, the DRG's from the rats were collected and processed for glutaminase and ZC-IR (FIG. 16). In the DRG, ZCIR was elevated (FIG. 16A) in rats with inflammation, but the ZC-IR (FIG. 16B) from rats treated with DC during inflammation was similar to controls. ZC-IR was found in the cytoplasm and nuclei (arrows) from rats with inflammation, whereas in rats treated with DC during inflammation, the nuclei (arrows) were not stained and ZC-IR was found primarily in the cytoplasm.

In the DRG, glutaminase-IR was observed at moderate levels from controls (FIG. 16C), elevated following inflammation (FIG. 16D), and similar to controls in rats treated with DC during inflammation (FIG. 16E). These data give further support to ZC's role in altering the expression of glutaminase during inflammation and that increased glutaminase is important for maintaining increased sensitivities during inflammation. In addition, it indicates that disruption of glutaminase synthesis during inflammation is potential target for providing pain relief.

Chronic Alterations in the DRG neuronal cell body. The DRG contains high levels of GT enzyme activity [Duce and Keen, 1983; Graham and Aprison, 1969; McDougal et al., 1981], but localization of GT to specific neuronal cell types has been controversial to those of ordinary skill in the art. Incubation of rat DRG's in [$^3$H]glutamine (converted to [$^3$H] glutamate via GT) labels neurons of all cell sizes [Duce and Keen, 1983]. Small sized neurons are stained exclusively with rabbit polyclonal GT antisera in PFA fixed tissue [Battaglia and Rustioni, 1988; Cangro et al., 1984, 1985], whereas most DRG neurons are stained using a mouse monoclonal GT antibody in PA-PFA fixed tissue [Miller et al, 1992, 2002]. Therefore, GT immunostaining was compared with the 2 different fixatives and antibodies. In side by side comparisons, the same pattern of GT immunostaining occurred for both GT antibodies depending on the fixative used. With PFA fixative, small sized DRG neurons were GT immunoreactive, but with PA-PFA fixative, the majority of the DRG neurons had GT-IR. This pattern is more consistent with glutamate immunohistochemistry where most DRG neurons are immunoreactive [Battagli and Rustioni, 1988; Stoyanova et al., 1998; Wanaka et al., 1987]. These results indicate that GT is sensitive to aldehyde fixation for detection with immunohistochemistry. The results from previous studies of glutaminase immunostaining [Battaglia and Rustioni, 1988; Cangro et al., 1984, 1985], therefore, may have caused glutaminase to be overlooked or underestimated as a target for pharmacological intervention for pain.

The increases in GT in the DRG after inflammation with complete Freund's adjuvant described herein further illustrate how primary sensory neurons are altered during chronic inflammation. If inflammation continues past the acute stage, the primary sensory neuron is induced into an altered phenotype making it more responsive to stimuli or sensitization. In animal tonic pain models, sensory neurons respond chronically by modifying neuropeptide, receptor, and ion channel production [Calzà et al., 1998; Donaldson et al., 1992; Garrett et al., 1995; Gould et al., 1998; Hanesch et al., 1993, 1995; Millan, 1999; Mulder et al., 1997, 1999; Nahin and Byers, 1994; Noguchi et al., 1988; Seybold et al., 1995; Smith et al., 1992; Tate et al., 1998; Zhang et al., 1998]. Increased IR for glutamate, the product of GT enzyme activity, has been observed in nerve fibers in the spinal cord of the monkey and rat after induction of experimental arthritis [Sluka et al., 1992, 1993]. This increase, presumably from primary sensory nerve fibers in the spinal cord, occurred at 4-12 hrs., but returned to normal levels by 24 hrs. [Sluka et al., 1993]. In the monkey medial articular nerve, the number of glutamate-immunoreactive, unmyelinated and thinly myelinated axons increased after inflammation by 2 hrs., peaked between 4-6 hrs., and returned to baseline by 8 hrs. [Westlund et al., 1992]. These acute alterations in glutamate-IR in axons and terminals cannot be attributed to alterations in the DRG neuronal cell body, but are likely to be caused by flux control mechanisms or alteration of glutamine cycle enzymes via signal transduction pathways [Curthoys and Watford, 1995; Fell, 1997]. For example, increased synaptic activity causes an elevation of phosphate by hydrolysis of ATP and an increase of calcium from entry into the nerve terminal. GT is activated by inorganic phosphate, i.e., phosphate-activated glutaminase (PAG), and phosphate activation is sensitized by calcium [Erecinska et al., 1990; Kvamme et al., 1979; Kvamme, 1998]. Thus increased electrical activity in sensory neurons at the acute stages of inflammation could cause GT activity in axons and terminals to be augmented to produce elevated amounts of glutamate [Erecinska et al., 1990; Kvamme et al., 1979, 1983, 1998].

In neurons exposed to chronic inflammation, long term regulation of glutamate levels is unlikely to be controlled in such a manner. Since DRG neuronal cell bodies have an altered phenotype that maintains or exacerbates inflammatory sensitization [Donnerer et al., 1992; Hanesch et al., 1993; Nahin and Byers, 1994; Ahmed et al., 1995; Garrett et al., 1995] and since most DRG neurons are glutamatergic [Miller et al., 1993, 2002a], it was necessary to determine if long-term alterations occur in glutamate metabolism of primary sensory neurons in chronic inflammation. Indeed, it has been shown herein that long-term elevated GT levels occur in DRG neurons during chronic inflammation. In the present invention, the largest long term increase of GT IR occurred in small and medium sized DRG neuronal cell bodies. Neurons of these sizes commonly are considered to include nociceptive neurons that give rise to unmyelinated C and lightly myelinated A-delta fibers [Cameron et al., 1986; Garry et al., 1989; Harper and Lawson, 1985; Willis and Coggeshall, 1991]. Elevated amounts of GT are likely to lead to increased production of glutamate in nociceptive, primary afferent nerve terminals in the spinal cord. SP and CGRP are found along with glutamate in primary afferent terminals [Merighi et al., 1991], and the co-release of glutamate and these neuropeptides generate hypersensitivity of spinal neurons [Besson et al., 1999]. Therefore, an increase in the amount of GT during chronic inflammation may lead to increased production and release of glutamate along with substance P and CGRP. Increased production and release of these substances could sustain spinal hypersensitivity maintaining a state of chronic pain.

Chronic alterations in peripheral nerve fibers. Increased production of GT in the DRG cell bodies could affect the peripheral process, also. Glutamate release occurs from peripheral processes [Bledsoe et al., 1980; Jackson et al., 1993; Lawand et al., 2000; Weinreich and Hammerschlag, 1975], and peripheral nerve terminals in skin contain glutamate receptors [Carlton et al., 1995, 1998; Carlton and Coggeshall, 1999; Coggeshall and Carlton, 1998]. Peripheral administrations of glutamate receptor agonists sensitize peripheral afferents and produce nociceptive reflexes/hyperalgesia [Ault and Hildebrand, 1993a,b; Carlton et al., 1998; Davidson et al., 1997; Jackson et al., 1995; Lawand et al., 1997; Sang et al., 1998; Wang et al., 1997; Zhou et al., 1996]. Following inflammation, the number of glutamate receptor immunoreactive axons in peripheral sensory nerve increases [Carlton and Coggeshall, 1999]. It is likely, therefore, that the increased GT in DRG cell bodies causes alterations in glutamate metabolism in the peripheral nerve fibers of the primary sensory neuron. In previous studies from our laboratory and in the present invention, the sensory nerve fibers in the skin of CFA inflamed rats have elevated levels of GT and glutamate with a time course similar to the DRG [Miller et al., 1999; Miller et al., 2002]. Increased glutamate production and release from peripheral processes could activate terminals with glutamate receptors leading to further sensitization of primary afferents. The release of glutamate could affect not only the nerve terminal where it was released, but also surrounding axon terminals and local cells [Carlton et al., 1995, 1998; Carlton and Coggeshall, 1999; Coggeshall and Carlton, 1998; Genever et al., 1999]. A cycle, therefore, of increased glutamate production and release, elevated numbers of axons with glutamate receptors, and maintenance of sensitization of peripheral nerve terminals would further exacerbate the process of chronic pain from the periphery.

As stated above, long-term changes due to inflammation, as demonstrated in the present invention, include an increase in glutaminase in the rat DRG cell body. This increase in glutaminase will lead to elevated production and release of glutamate at both the peripheral and central processes of primary afferents. An increase in glutamate metabolism in primary sensory neurons may be partly responsible for heightened nociceptive sensitivity in tonic pain models. Prevention of increased glutaminase production or inhibition of glutaminase enzyme activity, therefore, may reduce or block some nociceptive responses in inflammatory models.

Prevention of increased glutaminase production. Several neurotrophic factors, particularly NGF, have a significant role in altering the phenotype of sensory neurons during chronic inflammation [Woolf, 1996; Raja, 1995; Reinert et al., 1998; Koltzenburg, 1999]. NGF levels increase in inflamed tissue and NGF neutralization with TrkA-IgG into the inflamed field prevents hyperalgesia [Koltzenberg et al., 1999; Nicholas et al., 1999]. NGF causes an increase in mRNA for growth-associated protein 43 and preprotachykinin A [SP] in DRG neurons, and anti-NGF prevents these increases [Malcangio et al., 1997; Reinert et al., 1998]. These DRG neurons also are glutamatergic, but the influence of NGF on glutamate metabolism in chronic inflammation has not been investigated. NGF influences GT expression in DRG neurons in utero and in oculo [McDougal et al., 1981; Miller et al., 1999], and preliminary data indicate that NGF influences GT expression in the DRG and peripheral primary afferents similar to inflammation [Miller et al., 2001]. Therefore, it is believed that by inhibiting NGF's role on modifying glutamate metabolism in DRG neurons during chronic inflammation, GT expression and therefore glutamate levels can be reduced, thereby reducing nociceptive responses.

Once NGF or other signals reach the DRG neuronal cell body, long term regulation of GT activity can be altered. The long-term regulation of GT activity is controlled by the amount of GT produced and has been best studied in the kidney [Curthoys and Watford, 1995]. During chronic acidosis, GT activity increases within 24 hours and remains elevated for weeks after reaching a plateau at 7 days [Curthoys and Lowry, 1973]. This occurs by an increase in the amount of GT and not activation of the preexisting enzyme [Curthoys et al., 1976; Curthoys and Watford, 1995]. The rate of GT transcription is unaffected by these conditions, but the level of total and translatable GT mRNA is increased by stabilization of GT mRNA [Tong et al., 1987; Curthoys and Watford, 1995; Curthoys and Gstraunthaler, 2001]. Stabilization occurs by the binding of a cytosolic protein to an eight-base AU sequence repeat within the 3'-nontranslated region of the GT mRNA [Hansen et al., 1996; Laterza et al., 1997; Laterza and Curthoys, 2000; Porter et al., 2002]. This stabilizing protein is zeta-crystallin:quinone oxidoreductase [ZC; Tang and Curthoys, 2001; Curthoys and Gstraunthaler, 2001]. Since nervous system GT is similar or identical to kidney GT [Curthoys and Watford, 1995; Holcomb et al., 2000], it is possible that a similar mechanism exists in primary sensory neurons. Therefore, it is important to determine the role ZC has in increased GT production in DRG neurons during chronic inflammation. Several studies have shown altered levels of ZC in diseased neurons, tumor cells, and other tissues undergoing cellular stress [Wang et al., 2000; Siegel and Ross, 2000; Schelonka et al., 2000; Wilson et al., 2001]. In the present report, ZC levels increase in the DRG neuronal cell bodies during the early stages of inflammation, preceding increases in glutaminase. Inhibition of ZC, therefore, was carried out to determine if glutaminase levels and pain behaviors could be modified.

ZC is inhibited by several classes of compounds [al-Hamidi et al., 1997; Rabbani and Duhaiman, 1998; Winski et al., 2001; Bazzi et al., 2002]. Dicoumarol [DC] is a potent, competitive inhibitor of ZC, binding to the pyridine nucleotide site [Hollander and Ernster, 1975; Hosada et al., 1974, Jaiswal, 2000] and has been used as the traditional inhibitor of ZC in many studies [Cross et al., 1999; Winski et al., 2001]. Therefore, DC was administered to DRG neuronal cell bodies during chronic inflammation to disrupt ZC's regulation of GT production. The administration of DC caused a decrease in ZC and GT levels, as well as reducing nociceptive responses such as thermal hyperalgesia and mechanical allodynia.

Inhibition of glutaminase activity. Cutaneous primary afferents are classified into three general categories and proportions: 1. small diameter, unmyelinated, slow conducting C fibers [70%]; 2. medium diameter, lightly myelinated, intermediate conducting Adelta fibers [10%]; 3. large diameter, myelinated, fast conducting Ab fibers [20%] [Millan, 1999]. Under normal conditions, nociceptors are categorized into Adelta fibers that evoke a rapid, acute pain sensation and C fibers that produce a later, 'dull' pain [Campbell, 1987]. In acute inflammation there is a release of substances that sensitize normal peripheral primary afferents and recruit 'silent nociceptors' in an area of primary hyperalgesia, typified by increased sensitivity to mechanical, heat, and chemical stimuli. A secondary hyperalgesia in nearby undamaged areas is thought to be due to central spinal mechanisms [review, Millan, 1999].

Sensitizing substances released during acute inflammation include: 5-HT, histamine—mast cells; prosta-glandins (PG)—fibroblasts, Schwann cells; cytokines, $H_+$, nitric oxide (NO)—macrophages; ATP, $H_+$—damaged cells; 5-HT—platelets; ATP, NO—blood vessels; bradykinin, other kinins—blood; PG, neuropeptide Y, ATP—sympathetic terminals. There also is a neurogenic component of inflammation due to the release of bioactive substances from peripheral primary afferent terminals. Substance P (SP) and calcitonin generelated peptide (CGRP) are released from stimulated terminals or via axon reflexes (collateral fibers) further sensitizing surrounding afferent terminals and tissues. These algogenic substances influence primary afferents to increase $Ca_{2+}$ and $Na_+$ permeability, decrease $K_+$ permeability, increase intracellular $Ca_{2+}$ concentration, NO and PG production, and adenylate cyclase and phospholipase C activities [Millan, 1999]. The peripheral primary terminal, therefore, is acutely sensitized producing primary hyperalgesia.

Glutamate also is involved in neurogenic inflammation. As stated earlier, a number of stimuli evoke glutamate release from nerve trunks, skin, joints, and dental pulp [Bledsoe, et al., 1980, 1989; Jackson et al., 1993; deGroot et al., 2000; Lawand et al., 2000]. Local release or administration of glutamate and EAA agonists sensitize peripheral afferents and produce acute nociceptive reflexes/hyperalgesia that can be blocked by EAA antagonists [Ault and Hildebrand, 1993a, b; Jackson et al., 1995; Zhou et al., 1996; Davidson et al., 1997; Law and et al., 1997; Wang et al., 1997; Carlton et al., 1998; Ushida et al., 1999; Bhave et al., 2001]. Fibers of the Ab type also contain EAA receptors [Coggeshall and Carlton, 1997; Wood and Docherty, 1997] and may be involved in mechanical allodynia [Millan, 1999]. During acute inflammation, the number of glutamate-immunoreactive axons in peripheral nerve increases from 25% to 60% after several hours [Westlund et al., 1992]. This acute alteration in glutamate concentrations in peripheral primary afferents is due to local regulation of GT activity and glutamate production. The present invention shows that chronic alterations in glutamate concentrations, however, involves increased production of glutaminase in the neuronal cell bodies followed by increased amounts of glutaminase and glutamate in the peripheral nerve fibers.

Based on these studies, it is believed that increased glutamate production and release acting on elevated numbers of nerve terminals with glutamate receptors would maintain sensitization of peripheral afferents and exacerbate the process of chronic pain from the periphery. It has been shown herein that inhibition of GT via a one-time application of a GT enzyme inhibitor into the chronically inflamed field reduces nociceptive responses, such as mechanical allodynia and thermal hyperalgesia, and elevated glutamate levels during chronic inflammation for several days. Several classes of inhibitors acting at binding sites for glutamine and glutamate or at regulatory sites on glutaminase appear to be extremely effective in reducing pain responses.

In summary, it has been shown that glutamate metabolism is altered for weeks in rat primary sensory neurons during chronic inflammation. Elevated levels of glutamate and glutaminase (GT), its synthetic enzyme, occur in the neuronal cell bodies of dorsal root ganglia (DRG) followed by increases in the peripheral afferents of skin and joints. Chronic increase in production and release of glutamate can stimulate glutamate receptors on sensory afferents to produce hyperalgesia and allodynia. Therefore, elevated peripheral levels of glutamate cause exaggerated nociceptive responses during chronic inflammation. Recent studies have demonstrated that zeta-crystallin:quinone oxidoreductase (ZC) is a stabilizer of GT mRNA to increase GT levels. Also, nerve growth factor (NGF) has been shown to act as a retrograde signal from the site of inflammation to induce chronic alterations in sensory neurons. Therefore, ZC and NGF are responsible for altering GT levels in primary sensory neurons during chronic inflammation. The following conclusions can be made from the research presented herein:

(1) inhibition of GT reduces nociceptive responses and elevated glutamate levels during chronic inflammation. Inhibition of GT will be produced with a GT inhibitor at the DRG, sciatic nerve or in the inflamed paw during chronic inflammation.

(2) GT production in DRG neurons during chronic inflammation is regulated by ZC. ZC is a stabilizer of GT mRNA, allowing increased GT translation during times of cellular stress. An effective amount of a ZC inhibitor can be administered to the DRG to disrupt GT mRNA stabilization and reduce nociceptive responses during the development of chronic inflammation.

(3) glutamate metabolism in primary sensory neurons can be modified by NGF. NGF has been implicated in chronic alterations of DRG neurons. Administration of NGF to naive rats and NGF neutralization in chronic inflammation should have a similar effect as a ZC inhibitor on nociceptive behavior and glutamate metabolism in primary sensory neurons.

DETAILED DESCRIPTION OF FIGS. 17-24

In addition to the glutaminase inhibitors described herein above, the present invention also includes compounds that inhibit, either directly or indirectly, the synthesis of a substrate that is converted to a neurotransmitter. For example, glutaminase converts glutamine to the neurotransmitter glutamate, and therefore inhibitors of enzymes which are directly or indirectly involved in the synthesis of glutamine, such as but not limited to, pyruvate carboxylase, glutamate dehydrogenase, glutamine synthetase, and various known enzymes of the tricarboxylic acid (TCA) and glutamine cycles, also fall within the scope of the present invention.

Within the central nervous system (CNS), astrocytes contain several glial-specific enzymes related to the tricarboxylic acid (TCA) and glutamine cycles. For example, pyruvate carboxylase (PC), an anaplerotic enzyme, converts pyruvate to oxaloacetate for entry into the TCA cycle. Glutamate dehydrogenase (GDH) serves as a link between the TCA and glutamine cycles by reversibly converting 2-oxoglutarate into glutamate. Glutamine synthetase (GS) is one of two integral enzymes of the glutamine cycle and converts glutamate into glutamine. In the peripheral nervous system (PNS), several studies indicate that satellite cells of the dorsal root ganglia (DRG) and Schwann cells of peripheral nerves might fulfill similar roles as those of CNS astrocytes. Using $[1-^{14}C]$-pyruvate or $NaH^{14}CO_3$ incubation of DRG's, glutamate and glutamine pools are labeled, but in a different manner than incubation with $[^{14}C]$-glucose. This difference may be partially attributable to PC and glial uptake properties. $[^{14}C]$-Acetate preferentially is taken up by satellite cells and rapidly found in the glutamine cycle, suggesting the presence of GDH. Moreover, GDH enzyme activity has been described in DRG, dorsal roots, and peripheral nerves, although lower than in CNS regions. In addition, the Schwann cells of the giant squid nerve have 10 times the amount of GDH enzyme activity compared to nerve fiber axoplasm. DRG, dorsal roots, and peripheral nerves contain glutamine levels comparable to glutamate concentrations due to the high amount of GS activity found in dorsal roots and peripheral nerves. GS is localized in satellite and Schwann cells based on uptake studies of radiolabeled glutamate. In these studies, glutamate quickly enters satellite and Schwann cells and rapidly is converted to glutamine. These results have been interpreted in light of the CNS glutamine cycle hypothesis where glutamine taken up by neurons is converted to glutamate via glutaminase and glutamate is taken up by astrocytes for conversion to glutamine via GS.

Despite the indication from these studies, few to no investigations have been performed to immunohistochemically localize these enzymes or glutamine in the dorsal root ganglia and peripheral nerves. The present study was performed to clarify the cellular location and distribution of these substances.

Several fixatives were used in the present study to determine optimal immunoreactivity. A 4% paraformaldehyde, 0.3% glutaraldehyde fixation was suitable for glutamine, GS, and PC immunoreactivity, but little staining occurred for GDH. A 4% glutaraldehyde, 0.2% picric acid fixation was useful for GDH as previously reported, but glutamine, GS, and PC had little to no immunostaining. The 70% picric acid, 0.2% paraformaldehyde fixation provided equal or better immunostaining for all four substances compared to the other two fixatives. All photomicrographs were taken from tissues preserved with this fixative.

When sections were incubated in antiserum and respective antigen, no or weak immunoreactivity was observed (FIGS. 17A and B). When the primary antisera were omitted, no or weak immunoreactivity was observed (FIG. 17C). Use of the immunoperoxidase reaction with the omission of the primary antiserum caused some satellite cells in the DRG to appear (data not shown). These cells appeared when the reaction was allowed to proceed for several minutes after stopping the regularly stained immunoperoxidase sections. These data are similar to a previous paper describing endogenous peroxidase activity in glial cells. This type of staining did not appear in control sections stopped at the same time as regularly stained sections.

Figure 18:
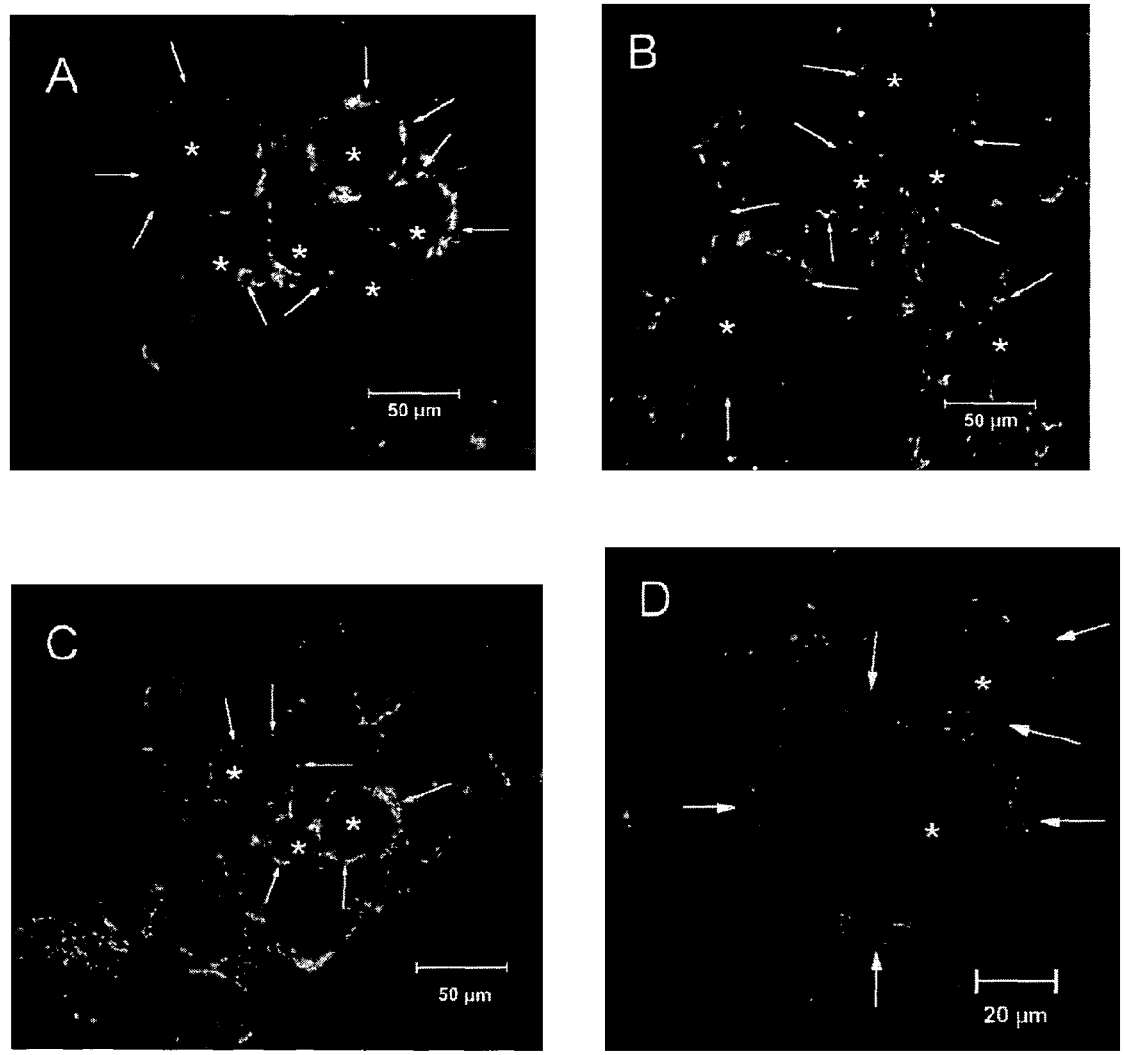
FIG. 18 are photomicrographs illustrating glutamine and enzyme immunoreactivity in DRG satellite cells. (A) Intensely labeled glutamineimmunoreactive satellite cells (arrows) surround the DRG cell bodies (*). (B) Satellite cells immunoreactive for glutamine synthetase surround DRG cell bodies (*). As with glutamine, GS immunoreactivity appears to have a cytoplasmic appearance. (C) Pyruvate carboxylase-immunoreactivity found in satellite cells (arrows) was punctuate in appearance. This section was adjacent to the absorption control shown in FIG. 17B. (D) Confocal micrograph of glutamate dehydrogenase immunoreactivity in satellite cells (arrows). GDH and PC immunoreactivities were punctuate in the cells and presumably are mitochondria (see detailed description herein below).
Figure 19:
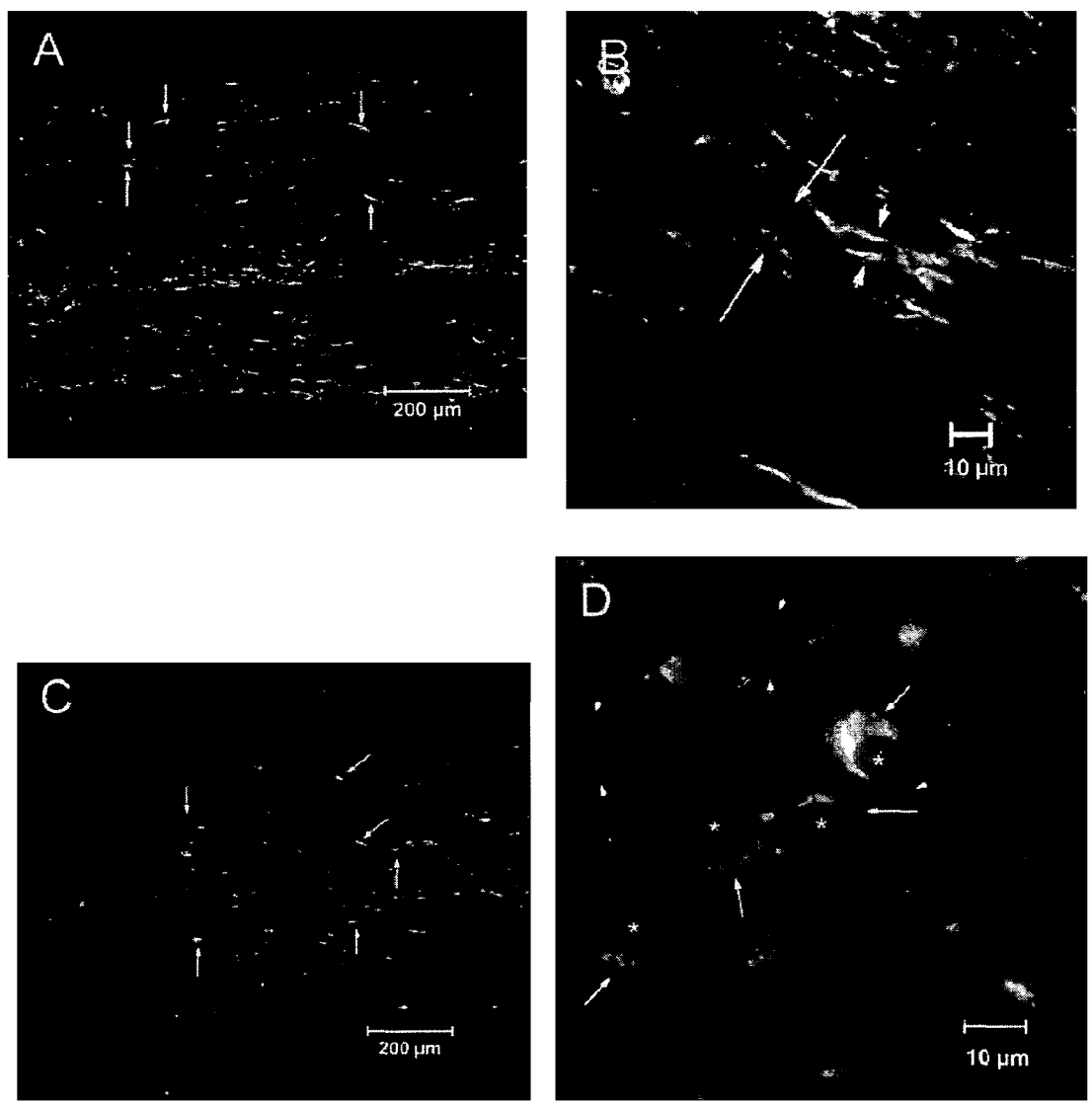
FIG. 19 are photomicrographs illustrating immunoreactivity in Schwann cells. (A) GLutamine immunoreactivity was found along the course of the sciatic nerve in long immunoreactive cellular processes. GLNimmunoreactive cell bodies (arrows) were apparent, also. This section was adjacent to the absorption control shown in FIG. 17A. (B) Confocal micrograph of glutamine synthetase immunoreactivity in Schwann cells. Arrows point to a node of Ranvier and arrowheads point to a Schwann cell body immunoreactive for GS. (C) Pyruvate carboxylase immunoreactivity occurred throughout the course of the sciatic nerve in long immunoreactive cellular processes and Schwann cell bodies (arrows). (D) Cross section of sciatic nerve with glutamate dehydrogenase immunoreactivity. GDH-immunoreactive Schwann cell bodies (arrows) wrap around axons (asterisks). Both GDH and PC immunoreactivities were observed as puncta (arrowheads).
Figure 20:
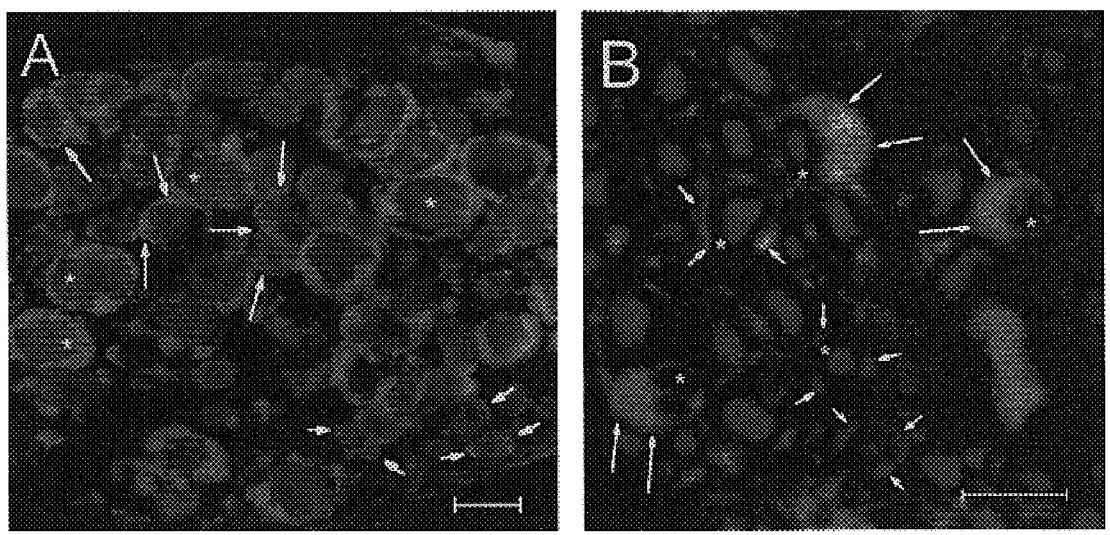
FIG. 20 are photomicrographs illustrating double immunofluorescence for glia and neurons. In (A), satellite cells (green) were stained for glutamine synthetase and neurons (red) for glutaminase in the DRG. GS appeared to stain all satellite cells. Glutaminase stained DRG neurons of all sizes. Small DRG neurons (<600 µm$^2$) were contacted by one to two satellite cells (small arrows), whereas medium (600-1200 µm$^2$) and large (asterisks, >1200 µm$^2$) DRG neurons were surrounded by three to seven cells (long arrows) in 20 µm thick sections. In (B), Schwann cells (green) were stained for GS and axons (red) for protein gene product 9.5 (PGP 9.5) in the sciatic nerve. With this confocal micrograph, GS staining was best observed in myelinating Schwann cells (arrows)

Similar results for all four substances were obtained with the immunoperoxidase and immunofluorescent techniques. For the present report, immunofluorescent photomicrographs were used to avoid any possible artifactual staining from immunoperoxidase staining as described above. In DRG and sciatic nerves, immunoreactive (IR) satellite (FIGS. 18 and 20) and Schwann cells (FIGS. 19 and 20) were observed for glutamine, GS, GDH, and PC. In DRG, most satellite cells appeared IR and surrounded all DRG neurons. In the sciatic nerve, many Schwann cells were IR and were apparent throughout the width and length of the nerve. Glutamine and GS appeared to stain the cytoplasm of the satellite and Schwann cells (FIGS. 18A,B and 19A,B), whereas GDH and PC immunoreactivity appeared as puncta within the satellite (FIGS. 18C and D) and Schwann cells (FIG. 19D). GDH and PC are localized to mitochondria, and a previous immunohistochemical study of GDH in the CNS demonstrated that the immunoreactive puncta are mitochondria. Some weak neuronal cell staining in the DRG was observed for glutamine, GDH, and PC, but axons in the sciatic nerve were not observed to be IR for any of the four substances.

In the sciatic nerve, IR Schwann cells were best observed around large diameter, myelinated axons (FIGS. 19B,D and 20B). Immunoreactivity was most intense in three areas of these Schwann cells: cell body (perinuclear) cytoplasm, nodes of Ranvier, and the rim of cytoplasm outside of the myelin (FIGS. 19B,D and 20B). The myelin sheath was not immunoreactive for any of the four substances (FIG. 20B).

As with CNS glia, the present invention demonstrates that DRG satellite and sciatic nerve Schwann cells contain specific enzymes related to the TCA and glutamine cycles. These results provide an anatomical confirmation and/or interpretation of several biochemical studies that proposed the localization of glutamine and related enzymes to satellite and Schwann cells (FIG. 21).

Pyruvate carboxylase is an anaplerotic enzyme that catalyzes the fixation of $CO_2$ to pyruvate to form oxaloacetate for entry into the TCA cycle [L. Hertz et al., 1999]. In the CNS, PC is important for the synthesis of glutamine and glutamate [W. C. Gamberino et al.1997; R. P. Shank et al.1985], and PC-immunoreactivity has been localized to astrocytes [M Cesar and B. Hamprecht, 1995; R. P. Shank et al., 1985]. The presence of PC in satellite cells may explain uptake and metabolism studies in sensory ganglia [J. L. Johnson, 1974; J. L. Johnson, 1976; P. Keen and P. J. Roberts, 1996; M. C. W. Minchin and P. M. Beart, 1975]. [$^{14}$C]-Glucose is taken up preferentially by DRG neurons and radiolabel is found in glutamate and alanine within minutes followed by a small amount of radiolabeled glutamine after 1 h [J. L. Johnson, 1976; M. C. W. Minchin and P. M. Beart, 1975]. When incubated in [2-$^{14}$C]-pyruvate or NaH $^{14}CO_3$, DRGs contain significant amounts of radiolabeled glutamine and glutamate at 15 and 60 min [J. L. Johnson, 1976; M. C. W. Minchin and P. M. Beart, 1975]. Radiolabeled glutamine and glutamate from [2-$^{14}$C]pyruvate [J. L. Johnson, 1976] could come from either PC or pyruvate dehydrogenase. Coupled with the present results, however, these studies indicate there is significant $CO_2$ fixation to pyruvate in satellite cells for oxaloacetate formation (FIG. 21). This anaplerotic action of PC could allow carbon to be drawn from the TCA cycle for conversion to glutamine and glutamate in the glutamine cycle.

Other work has indicated that pyruvate carboxylation also occurs in neurons [B. Hassell and A. Bråthe, 2000; C. J. Van den Berg, 1972]. Cerebellar granule cells intercultured in the absence of astrocytes and incubated in [1-$^{14}$C]pyruvate are capable of pyruvate carboxylation [B. Hassell and A. Bråthe, 2000]. In neuronal cultures grown in the absence of astrocytes, neurons may increase production of enzymes that are not expressed or expressed at low levels under normal conditions. Studies with striatal injections of radiolabeled pyruvate indicate that pyruvate carboxylation can occur in vivo in neurons [B. Hassell and A. Bråthe, 2000]. Following injection of [1-$^{14}$C]pyruvate, there was higher specific activity in glutamate than glutamine which was interpreted as a predominant neuronal carboxylation of pyruvate [B. Hassell and A. Bråthe, 2000]. In the present study, a weak PC IR in DRG neurons suggests a low level of PC expression in vivo in DRG neurons. The low amount of PC IR staining in the DRG neurons and the apparent large amount of pyruvate carboxylation in the rat striatal neurons may indicate heterogenous expression of PC in different neuronal areas. Alternatively, the rat PC gene has 19 coding exons and at least two alternate promoters to produce multiple PC transcripts [S. Jitrapakdee et al., 1996; S. Jitrapakdee et al., 1997]. The putative PC expressed by neurons [B. Hassell and A. Bråthe, 2000] may be a PC isoform with antigenic sites not recognized by the antisera used in the present study.

A link between the TCA and glutamine cycles has been observed in the DRG. [$^{14}$C]-Acetate is taken up preferentially by satellite cells [M. C. W. Minchin and P. M. Beart, 1975], possibly via a transport mechanism similar to CNS astrocytes [R. A. Waniewski and D. L. Martin, 1998]. Once inside satellite cells, [$^{14}$C]-label is incorporated rapidly in glutamate and glutamine [J. L. Johnson, 1974; P. Keen and P. J. Roberts, 1996; M. C. W. Minchin and P. M. Beart, 1975; P. J. Roberts and P. Keen, 1974]. This could be interpreted by conversion of 2-oxoglutarate into glutamate via one of two ways, aminotransferases (ATs) or GDH (FIG. 21). It is unlikely that aspartate ATs are responsible for this conversion, since both cytosolic and mitochondrial aspartate ATs are localized to DRG neurons [I. Inagaki et al., 1987]. Based on the current localization of intense GDH IR and previous enzymatic studies [L. T. Graham, Jr. and M. H. Aprison, 1969; J. L. Johnson, 1972], it is more likely that GDH in satellite and Schwann cells is responsible for most of the conversion of 2-oxoglutarate to glutamate for entry into the glutamine cycle.

As with PC, GDH appears to be enriched in glial cells, but neurons also have been implicated to have this enzyme. Neuronal GDH enzyme activity has been detected in CNS synaptosomes [C. Arce et al., 1990; N. Kuo et al., 1994; M. Yudkoff et al., 1991], although it is difficult to determine the amount of astrocytic contamination from such preparations. Immunohistochemical studies in CNS typically have localized GDH to astrocytes [T. Kaneko et al., 1987; T. Kaneko et al., 1988; J. E. Madl et al., 1988], but some studies have noted weak to light immunostaining in neurons [C. Aoki et al., 1987; F. Rothe et al., 1990; F. Rothe et al., 1994; R. J. Wenthold et al., 1987]. A study using in situ hybridization and immunohistochemistry for GDH has demonstrated that neurons can express GDH in varying amounts depending on the CNS location [A. Schmitt and P. Kugler, 1999]. Previous reports on the DRG have indicated that both satellite cells and neurons contain GDH. Using enzyme histochemistry, the cytoplasm of chicken DRG neuronal cell bodies during development and in vitro contained granular reaction product, whereas satellite and Schwann cells had light reaction product [Z. Kra-nicka, 1970].

Individually microdissected rabbit DRG neuronal cell bodies contained GDH activity in both the cytoplasm and nucleus [T. Kato and O. H. Lowry, 1973]. The presence of GDH activity in the nucleus may indicate an alternative role for GDH such as a mRNA-binding protein, e.g. cytochrome c oxidase transcript-binding protein (COLBP) [T. Preiss et al., 1993; T. Preiss et al., 1995]. Using in situ hybridization and immunohistochemistry, Schmitt and Kugler (1999) showed very low GDH staining in satellite cells of rat cervical DRGs. The current study demonstrated very weak GDH immunostaining in DRG neurons and strong immunostained satellite and Schwann cells. These disparate findings in the DRG are difficult to reconcile. In all other studies, fresh frozen tissue was used to determine histochemical [Z. Kra-nicka, 1970], biochemical [T. Kato and O. H. Lowry, 1973], or immunohistochemical [A. Schmitt and P. Kugler, 1999] GDH activity or staining, whereas the present study used perfusion fixed tissue. GDH may exist in multiple forms with different biophysical properties [S. W. Cho et al., 1995; S. W. Cho et al., 1996; A. D. Colon et al., 1986; J. Lee et al., 1995] and detection of these forms via diverse methods may give rise to the differences observed in the various DRG studies.

Earlier studies have localized GS immunoreactivity in satellite cells of the spiral ganglion, Schwann cells of the osseous spiral lamina, and glia of the enteric nervous system [M. Eybalin et al., 1996; K. R. Jessen and R. Mirsky, 1983; H. Kato et al., 1990]. GS immunoreactivities, however, in the cochlear nerve and peripheral nerves entering the enteric nervous system have been described as weak to absent [M. Eybalin et al., 1996; H. Kato et al., 1990]. The results presented herein indicate robust GS and glutamine immunoreactivities in Schwann and satellite cells and are complimentary to previous investigations of glutamine and glutamate metabolism in the PNS. Studies using radiolabeled glutamate indicate rapid entry into satellite and Schwann cells [I. R. Duce and P. Keen, 1983; P. Keen and P. J. Roberts, 1996; P. J. Roberts and P. Keen, 1996; P. J. Roberts and P. Keen, 1974; D. D. Wheeler and L. L. Boyarsky, 1968], possibly by one of the glutamate transporters described for CNS glia [N. C. Danbolt et al., 1998]. Once inside, glutamate rapidly is converted to glutamine [I. R. Duce and P. Keen, 1983; P. Keen and P. J. Roberts, 1974; P. J. Roberts and P. Keen, 1973; P. J. Roberts and P. Keen, 1974; D. D. Wheeler and L. L. Boyarsky, 1968] via GS [L. T. Graham, Jr. and M. H. Aprison, 1969; M. J. Politis and J. E. Miller, 1985]. Light glutamine IR was observed in DRG neuronal cell bodies and most likely is due to uptake of glutamine released from nearby GS and glutamine positive satellite cells. Biochemical studies of DRGs indicate that this glutamine would be transformed rapidly into glutamate [I. R. Duce and P. Keen, 1983; P. Keen and P. J. Roberts, 1996; P. J. Roberts and P. Keen, 1973; P. J. Roberts and P. Keen, 1974; D. D. Wheeler and L. L. Boyarsky, 1968]. Glutamine transfer in the PNS between glia and neurons might use similar glutamine transporters as in the CNS (SN1-glia; SAT/ATA-neurons) [S. Bröer and N. Brookes, 2001].

Often, the glutamine cycle is described as a phenomenon occurring at the synaptic terminal and astrocytic process for production and degradation of glutamate as a neurotransmitter [G. J. Siegel et al., 1999]. Based on the current study and other reports, the uptake of glutamine and conversion to glutamate for eventual synaptic use may also occur in the cell bodies and axons of DRG neurons [J. L. Johnson, 1974; J. L. Johnson, 1974; P. J. Roberts and P. Keen, 1973; P. J. Roberts, 1974]. In addition, glutamine is the branch point substrate for multiple metabolic paths [A. J. L. Cooper, 1988] (FIG. 21) and the localization of glutamine-related enzymes in satellite cells surrounding neuronal cell bodies and Schwann cells associated with axons denotes a larger role than neurotransmitter regulation [P. R. Laming, 1998; S. R. Robinson et al., 1998]. In the CNS, GS is important for shuttling carbon in the form of glutamine from astrocytes to be used in the neuronal TCA cycle [D. L. Martin and R. A. Waniewski, 1996]. Alternatively, GDH can convert glutamate to 2-oxoglutarate for release and neuronal energy use, along with related metabolites, malate, pyruvate, and lactate [G. C. Leo et al., 1993; D. L. Martin and R. A. Waniewski, 1996; L. Pellerin et al., 1998; R. P. Shank and D. J. Bennett, 1993; N. Westergaard et al., 1994]. In addition, glutamine and glutamate are used as amino acids in most proteins and glutamine is a primary source for purine biosynthesis [A. J. L. Cooper, 1988]. Glutamine phosphoribosylpyrophosphate amidotransferase (GPATase; EC 2.4.2.14) represents the first and key regulatory enzyme for de novo purine synthesis [S. Li et al., 1999; H. Zalkin and J. L. Smith, 1998]. Glutamine concentrations and GPATase activity limit the rate of de novo purine synthesis [J. H. Kim et al., 1996; L. J. Messenger and H. Zalkin, 1979; J. L. Smith, 1998] and are linked closely to cellular activity, e.g., increased transcriptional-requirements and augmented ATP levels for elevated energy demands [J. Allsop and R. W. Watts, 1980; S. Beardsley et al., 1988; M. Itakura et al., 1986; J. L. Smith, 1998; T. Yamaoka et al., 1997; H. Zalkin and J. L. Smith, 1998]. This may explain the decrease in GS activity in the distal portion of transected peripheral nerve [M. J. Politis and J. E. Miller, 1985] where the Schwann cell's role as a neuronal (axonal) nutritive source would diminish with the degeneration of the distal axon. In cases of elevated neuronal activity, e.g., increased electrical activity or neuropeptide production with peripheral sensitization or regeneration, we postulate that glutamine-related enzyme metabolism would increase along with overall general satellite and Schwann cellular activity (e.g., Refs. [R. W. Leech, 1967; B. Stevens et al., 1998]).

To summarize the work shown in FIGS. 17-21, glutamine, GS, GDH, and PC are enriched in DRG satellite cells and peripheral nerve Schwann cells. Glutamine and related enzymes in these cells may facilitate glutamate production in DRG neurons for synaptic transmission in the spinal dorsal horn. Additionally, we hypothesize that glutamine and related enzymes in the PNS are required for appropriate neuronal cell body and axon function. Further studies examining glutamine-related metabolic flux and enzyme expression, concentration, and activity in different states, e.g. neuropathies or chronic sensitization, will help in understanding the various roles attributed to PNS glial cells.

As described hereinabove, the 'glutamine cycle' is a set of enzymes that are responsible for the production and degradation of the neurotransmitter glutamate in the central nervous system. The glial TCA cycle is intimately associated with the glutamine cycle. Enzymes associated with the 'glutamine cycle' are present in glial cells in the peripheral nervous system, including glutamine synthetase, glutamate dehydrogenase, and pyruvate carboxylase, and these glial enzymes are elevated after the induction of experimental arthritis in rats. This allows primary sensory neurons to increase glutamate production in their cell bodies and peripheral nerve fibers. The neuronal cell bodies and nerve terminals, therefore, have increased amounts of glutamate. The 'glutamine cycle' had not been adequately described in the peripheral nervous system until the present invention, so these enzyme have not previously been considered as possible therapeutic targets for pain relief via peripheral inhibition.

In FIGS. 22A and 22B, the hindpaw responses of rats to pressure and thermal sensitivity were determined several days prior to the start of the experiment. On Day 0, two groups were formed: 1. Control group with saline injection into the hindpaw; 2. Inflammation group with injection of complete Freund's adjuvant into hindpaw. At Day 3, a glutamine synthetase inhibitor, methionine sulfoximine (MSO), was injected into half of the rats with inflammation. The other rats received a saline injection at Day 3. Rats were tested for 4 days (pressure) or 6 days (thermal) following glutamine synthetase inhibition. Prior to inflammation, rats responded to ~70 gms of pressure and at ~9 sec for thermal stimulation. Following inflammation, pressure responses dropped to ~10 gms and thermal responses dropped to ~3 sec. After glutamine synthetase inhibition, pressure responses increased over several days up to ~50 gms. Thermal responses increased to near normal levels by day 6 through day 9. This type of pain relief was effective after a one-time administration of inhibitor.

In FIG. 23, rats were implanted with intrathecal (i.t.) cannulae to the lumbosacral spinal cord and sensory ganglia. The hindpaw responses of rats to pressure sensitivity were determined several days prior to the start of the experiment. On Day 0, rats were injected with saline injection into the hindpaw or with injection of complete Freund's adjuvant into hindpaw. Prior to the initiation of inflammation, a glutamine synthetase inhibitor, methionine sulfoximine (MSO), glutaminase inhibitor, 6-diazo-5-oxo-L-norleucine (DON), or glial TCA cycle inhibitor, fluoroacetate (FA), was injected intrathecally into some of the rats with inflammation. The other rats received a saline intratheca injection. Rats were tested for 4 days following initiation of inflammation. Prior to inflammation, rats responded to ~70 gms of pressure. Following inflammation, pressure responses dropped to ~10 gms, whereas rats with intrathecal inhibitors were able to maintain near normal pressure responses for several days.

FIG. 24 illustrates that satellite (glial) cells in the dorsal root ganglia (DRG) increase 'glutamine cycle' enzymes and products during chronic inflammation. Inflammation was induced with intraplantar CFA in the right hindpaw. In normal DRG's, glutamine synthetase (A; GS) and glutamine (C; the product of GS) immunoreactivity is located in satellite cells surrounding DRG neuronal cell bodies. After 3 days of inflammation, increased immunoreactivity for GS and glutamine is observed in most satellite cells.

In summary, the present invention provides pain relief (thermal and mechanical) for several days by way of 'glutamine cycle' or glial TCA cycle inhibition. While two examples of such inhibitors have been used herein, namely MSO and FA, it is to be understood that other inhibitors of the 'glutamine cycle' and the glial TCA cycle known to those of ordinary skill in the art also fall within the scope of the present invention. For example, other pyruvate carboxylase inhibitors that may be used in accordance with the present invention include, but are not limited to, phenyl acetic acid (PM) [Farfari et al., 2000; Bahl et al., 1997], phenylacetyl Coenzyme-A [Bahl et al, 1997], phenylacetyl Co-A ester, oxamate [Martin-Requero et al., 1986; Attwood et al, 1992], and combinations and derivatives thereof. Examples of glutamine synthetase inhibitors that may be used in accordance with the present invention include, but are not limited to, methionine-S-sulfoximine (MSO) [Sellinger, 1967; Ronzio et al, 1969], phosphinothricin (PPT) [Fushiya et al, 1988; Gill et al, 2001], 4-N-hydroxy-L-2,4-diaminobutyric acid (NH-DABA) [Fushiya et al, 1988], Delta-hydroxylysine [Dranoff et al, 1985], and combinations and derivatives thereof. Examples of glutamate dehydrogenase inhibitors that may be used in accordance with the present invention include, but are not limited to, bromofuroate [Matsuno et al, 1986; Vorhaben et al, 1977], Palmitoyl-Coenzyme-A (Palmitoyl-Co-A) [Fang et al, 2002; Lai et al, 1993], vanadium compounds (including, but not limited to, orthovanadate, vanadyl sulphate, vanadyl acetylacetonate, and combinations thereof) [Kiersztan et al, 1998], glutarate, 2-oxoglutarate (α-ketoglutarate) [Caughey et al, 1957], estrogen and estrogen analogues [Pons et al, 1978], pyridine-2,6-dicarboxylic acid [Broeder et al, 1994], and derivatives thereof as well as combinations thereof, such as, but not limited to, 2-oxoglutarate and vanadyl sulphate [Kiersztan et al, 1998]. Examples of glial cell TCA cycle inhibitors that may be used in accordance with the present invention include, but are not limited to, fluoroacetate [Swanson et al, 1994; Hulsmann et al, 2003], fluorocitrate [Swanson et al, 1994; Hulsmann et al, 2003], and combinations and derivatives thereof.

Thus it should be apparent that there has been provided in accordance with the present invention methods for alleviating pain and compositions having sustained pain-relieving properties that fully satisfy the objectives and advantages set forth above. Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

MATERIALS AND METHODS

For the experiments described in FIGS. 1-16, adult Sprague Dawley male rats, 200-300 g, were used. One set of normal rats was used to evaluate the effects of fixation on glutaminase immunohistochemical staining and for determining antisera dilutions. For all other rats, at day 0, a limited arthritis was induced in the right hindpaw by the intraplantar subcutaneous injection of 75-150 μl of complete Freund's adjuvant (CFA; *Mycobacterium butyricum;* Sigma) emulsified in saline (1:1). Controls were naive rats that received no injection or rats that received intraplantar injection of saline (75 μl). For peripheral glutaminase inhibition studies, the inflamed hindpaws were injected with glutaminase inhibitors (25 μl) at day 3 of inflammation. Some rats with inflammation received saline injections (25 μl) into the inflamed hindpaw at day 3. Procedures in this study were conducted according to guidelines from the International Association for the Study of Pain [Zimmerman, 1983] and the National Institutes of Health publication #80-23 and were approved by the University of Oklahoma Health Sciences Institutional Animal Care and Use Committee. Efforts were made to minimize the number of animals used for this study.

The $L_4$DRG was examined for the following reason. The tibial nerve, a branch of the sciatic nerve, innervates the majority of the plantar surface of the rat hindpaw [Swett and Woolf, 1985]. Approximately, 99% of the tibial DRG neuronal perikarya of rats are located in the $L_4$-$L_5$ DRG's, and the $L_4$ DRG contains more than twice the number than $L_5$ [Swett et al, 1991].

Two to three days prior to and for the days following CFA injection, rats were tested for pressure sensitivity with von Frey hairs (Semmes-Weinstein monofilaments; Stoelting, Inc.). Rats were allowed to acclimate for five to ten minutes in a plastic box (25×25×25 cm) with 6 mm holes spaced every 6 mm [Pitcher et al, 1999a,b]. Monofilaments calibrated for specific forces were inserted through the holes underneath the box to probe the plantar surface of the hindpaw, 5 times in 3-4 sec intervals in different places on the plantar surface. Filaments with light force were used first, followed by filaments of increasing force. A filament was slowly applied perpendicularly to the plantar surface until bending of the filament occurred. If the paw did not retract three out of five times, the next larger filament was used. The threshold force was defined as the filament (force) that caused the foot retraction without bending the monofilament three out of five times. Using a conversion table for the filaments, thresholds were reported as gram force.

Thermal latencies for the footpad plantar surface were determined with the Hargreaves' model (Ugo Basile, Italy). Rats were placed on an elevated glass plate (3 mm) in clear plastic boxes with air holes in the lids and allowed to acclimate for 10 minutes. Radiant heat was applied to the plantar surface of the hindpaw and the withdrawal latency recorded. A second test was followed after 5-10 minutes. All behavioral testing occurred at 21-22° C. with indirect lighting in the testing room. Differences between groups for pressure thresholds and thermal latencies were determined with a Student's t test (p<0.05 for significance) using InStat biological statistics program (GraphPad Software, Inc., San Diego).

For immunohistochemical localization of GT, rats at 3, 7, and 10 days (n=6 CFA/time pt; n=4 control/time pt; n=3 additional controls) were anesthetized with sodium pentobarbital (90 mg/kg) and transcardially perfused with fixative: 0.2% paraformaldehyde (PFA), 70% picric acid (PA) in 0.1M phosphate buffer, pH 7.4 [Miller et al, 1993, 2002]. Right and left $L_4$DRG's and hindpaws were removed and placed overnight in fixative at 4° C.; the PFA concentration was increased to 2% for post-fixation [Miller et al, 1993, 2002]. Additional control rats (n=3) were perfused transcardially with 4% PFA in 0.1M Sorenson's phosphate buffer, pH 7.4. DRG's were removed and placed in fixative overnight at 4° C. All tissues were transferred to 20% sucrose in 0.1M Sorenson's phosphate buffer, pH 7.4 for 24-96 hr. at 4° C. The tissue was frozen, sectioned at 20 µm in a cryostat, thaw mounted onto gelatin coated slides, and dried for 1 hr. at 37° C. Sections were washed three times for 10 min. in phosphate buffered saline (PBS) and incubated in 10% normal goat serum, 10% normal horse serum, 10% fetal bovine serum, 2% BSA, and 1% polyvinylpyrolidone in PBS with 0.3% Triton (PBS-T).

To evaluate the effects of fixation on GT immunoreactivity (IR), DRG sections from the first set of control rats (n=3 PA—PFA fixation; n=3 PFA fixation) were examined. Sections were incubated in rabbit anti-glutaminase (1:1000; gift from Dr. N. Curthoys, Colorado St. Univ., Ft. Collins, Colo.), mouse anti-glutaminase (IgM MAb 120, 1:500-5 mg/ml; gift from Dr. T. Kaneko, Kyoto Univ., Kyoto, Japan), or mouse anti-glutamate (1:3000; gift from Dr. J. Madl, Colo. St. Univ., Ft. Collins, Colo.) in PBS-T. The tissue was washed three times in PBS and incubated in biotinylated goat anti-rabbit IgG or biotinylated goat anti-mouse IgM secondary antibody (5 µg/ml; Vector) in PBST for 1 hr. Some tissue sections were washed two times in PBS following secondary antibody incubation, washed in sodium carbonate buffered saline (SCBS), pH 8.5, incubated in fluorescein-avidin (1.5 mg/ml; Vector) in SCBS for 1 hr., and washed three times in PBS. Coverslips were apposed with Vectashield mounting media (Vector) to retard fading of immunofluorescence. Other sections were washed three times in PBS following secondary antibody, incubated in avidin-biotin-peroxidase (Vector), and washed three times in Trisbuffered saline, pH 7.6. Sections were incubated in diaminobenzidine (DAB) solution (0.5 mg/ml DAB, 0.003% $H_2O_2$ in Tris-saline) for 1-5 minutes. Sections were dehydrated in an ascending series of ethanols, cleared in xylenes, and coverslips were apposed with Pro-Texx (Baxter Diagnostics).

A series of dilutions (1:200-1:6000) of the rabbit anti-glutaminase antiserum was used to determine an optimal dilution (1:3000) for evaluating alterations in immunohistochemical staining intensity. Also, a series of dilutions of the biotinylated goat anti-rabbit IgG secondary antiserum (1-15 µg/ml) was used to determine an optimal dilution (3 µg/ml) for this study. Tissue sections for the CFA inflammation study were incubated overnight at 4° C. in rabbit antiglutaminase (1:3000) in PBS-T and processed for immunofluorescence as described above. Immunofluorescent and immunoperoxidase sections were observed with an Olympus Provis AX70 microscope and digital images were obtained with a SPOT™ CCD camera (Diagnostic Instruments).

DRG's were evaluated qualitatively for 3, 7 and 10 day groups, and the 7 day group was chosen for quantitative densitometric analysis. Immunofluorescent images from 7 day DRG's were captured using the CCD camera and saved as uncompressed TIFF files. Exposures were adjusted and pre-set by using experimental (CFA) images for baseline exposure. The glutaminase-immunoreactive DRG images were analyzed using the SCION Image program (Scion Co., Frederick, Md.). Individual DRG neurons were circumscribed, and the area, pixel number, and intensity were recorded. The data were recorded as intensity divided by the area of the cell. Neuronal cell bodies in the DRG were distributed into the following three sizes for analysis: 100-600 $\mu m^2$ (small), 600-1200 $\mu m^2$ (medium), and >1200 $\mu m^2$ (large) [Willis and Coggeshall, 1991]. Differences in the intensity per area were analyzed with ANOVA followed by a Student-Newman-Keuls post hoc test (p<0.05 for significance) using InStat biological statistics program (GraphPad Software, Inc.).

For GT enzyme assays, rats from the 7 day time point (n=6 CFA; n=4 control) were anesthetized (sodium pentobarbital, 90 mg/kg) and decapitated. Right and left $L_4$ DRG's were removed quickly, placed in embedding molds with—1 mounting media (Lipshaw), and frozen on dry ice. Individual DRG's were sectioned at −20° C. on a cryostat at 30 µm. Sections were placed in aluminum racks for lyophilization, and samples were stored under vacuum at −20° C. The embedding media was removed from around the lyophilized DRG sections using a Wild Heerbrugg type 181300 dissecting microscope, and DRG sections were weighed using quartz-fiber balances.

Enzyme assays for GT were performed according to the method of Curthoys and Lowry (1973). Five to six randomly selected sections of right and left DRG from rats with CFA and from control rats were placed individually in a 40:1 volume of reaction mixture containing: 20 mM glutamine, 100 mM $K_2HPO_4$, 0.6 mM EDTA, 0.01% Triton-X 100, 0.01% BSA in 50 mM TRIS, pH 8.65, for 45 minutes at 37° C. The reaction was stopped by adding 20 µl of 0.7 N HCl and placing the samples at 4° C. A volume of 1 ml of indicator buffer containing 300 µMADP, 360 µMNAD, 50 µg/ml glutamate dehydrogenase (GDH, rat liver, Boehringer Mannheim, Indianapolis, Ind.) in 50 mM TRIS, pH 8.5 was added for 20 minutes at room temperature. In this reaction, glutamate produced by GT is converted to 2-oxoglutarate via GDH with the formation of NADH. Reduction of $NAD^+$ was measured using a fluorometer (Farrand Inc.) with an excitation wavelength of 365 nm and emission at 340 nm. Quantitation of NADH production was accomplished by reacting multiple concentrations of glutamate standards in the indication reaction. The GT activity from each DRG section was ascertained and a mean activity for each DRG was determined. Differences in GT activity from the left and right $L_4$ DRG's of CFA rats and $L_4$ DRG's from control rats were analyzed with ANOVA followed by a Student-Newman-Keuls post hoc test (p<0.05 for significance) using InStat biological statistics program (GraphPad Software, Inc.).

For the experiments described in FIGS. 17-24, experiments were carried out with approval from the University of Oklahoma Health Sciences Center Institutional Animal Care and Use Committee and in accordance with guidelines from the National Institutes of Health publication #80-23. Efforts were made to minimize the number of animals used for this study. Male Sprague-Dawley rats (n=19) were anesthetized with sodium pentobarbital (90 g/kg) and transcardially perfused with fixative. Three fixatives were used at pH 7.4: (1) 4% paraformaldehyde, 0.3% glutaraldehyde in 0.1 M Sorenson's phosphate buffer; (2) 4% glutaraldehyde, 0.2% picric acid in 0.1 M Sorenson's phosphate buffer [J. E. Madi, et al., 1988]; (3) 0.2% photoparaformaldehyde, 70% picric acid in 0.1 M phosphate buffer [K. E. Miller, et al., 1993]. Lumbar DRGs and sciatic nerves from the mid-thigh were removed and placed in fixative at 4° C. overnight. The paraformaldehyde concentration of fixative #3 was increased to 2% for post-fixation [K. E. Miller, 1993]. Tissues were transferred to 20% sucrose in 0.1 M Sorenson's phosphate buffer, pH 7.4, for 24-96 h. The tissue was frozen, sectioned at 20 μm in a cryostat, thaw mounted onto gelatin-coated slides, and dried for 1 h at 37° C. Sections were washed three times for 10 min in phosphate buffered saline (PBS) and incubated in 10% normal goat serum, 1°% normal horse serum, 10% fetal bovine serum, 2% BSA, and 1% polyvinylpyrolidone in PBS with 0.$^3$% Triton (PBS-Triton). Sections were incubated overnight at 4° C. in: rabbit anti-glutamine (1:1000; Chemicon International, Temecula, Calif., USA); mouse anti-glutamine synthetase (1:1000; G45020; Transduction Laboratories, Lexington, Ky., USA); mouse anti-glutamate dehydrogenase (1:10,000; J. Madl, Colorado St. Univ., Ft. Collins, Colo., USA); rabbit anti-pyruvate carboxylase (1:100; J. Wallace, Univ. Adelaide, Adelaide, SA, Australia); mouse anti-pyruvate carboxylase (1:300; B. Pfeiffer, Physiol.-Chem. Inst. Univ. Tubingen, Tubingen, Germany). The tissue was washed three times in PBS and incubated in biotinylated secondary antibody (3 mg/ml; Vector), either goat anti-rabbit IgG or horse anti-mouse IgG, for 1 hr. For immunoperoxidase staining, sections were washed three times in PBS, incubated 1 hr. in avidin-biotin-peroxidase (Vector), washed two times in PBS, washed in Tris buffered saline (TBS), pH 7.6, and reacted in 0.5 mg/ml diaminobenzidine, 0.03% $H_2O_2$ in TBS for 1-4 min. The reaction was stopped by washing the tissue three times in PBS. Sections were dehydrated in an ascending series of ethanols, cleared in xylenes, and coverslips apposed with Pro-Texx permanent mounting media (Baxter). For immunofluorescence, sections were washed two times in PBS following secondary antibody incubation, washed in sodium carbonate buffered saline, pH 8.5, incubated in fluorescein-avidin (1.5 mg/ml; Vector) for 1 hr., and washed three times in PBS. Coverslips were apposed with Vectashield mounting media (Vector) to retard fading of immunofluorescence.

The DRGs and sciatic nerves from four rats were used for double immunofluorescence. Sections were incubated overnight in mouse anti-GS with rabbit anti-glutaminase (GT, 1:1000, N. Curthoys, Colorado St. Univ.) or rabbit anti-protein gene product 9.5 (PGP-9.5, 1:500, Chemicon). To detect rabbit anti-GT or anti-PGP 9.5, Cy3-labeled donkey anti-rabbit IgG (1:1000, Jackson Laboratories, West Grove, Pa., USA) was incubated with the biotinylated horse anti-mouse IgG. The remainder of the immunofluorescence protocol was the same as described above.

Immunoperoxidase stained sections were observed and photographed in brightfield or differential interference contrast with an OlympusProvis AX70 microscope. Immunofluorescent sections were observed and photographed with epifluorescence microscopy using an Olympus Provis AX70 microscope or with confocal microscopy using a Leica TCS NT confocal microscope (OUHSC/Warren Foundation Flow and Image Cytometry Laboratory).

In addition to previous characterizations of these antisera [M. Cesar, et al. 1995; J. E. Madl, et al., 1988; M. Rohde, et al., 1991], the following controls were performed for the present study. For absorption controls, antisera for enzymes were incubated overnight in their respective antigen, 50 μg protein (Sigma) /ml diluted serum. For glutamine, antiserum was incubated in 1 mM glutamine and 1 mM polyglutamine /ml diluted serum. Antisera were incubated on tissue sections and processed at the same time as regularly immunostained sections. Omitting the primary antisera followed by normal immunohistochemical protocol performed a second control.

REFERENCES

The following references, to the extent that they provide exemplary procedural or other details supplementary to those set forth herein, are specifically incorporated herein by reference in their entirety.

M. Ahmed, A. Bjurholm, M. Schultzberg, E. Theodorsson, and A. Kreicbergs, (1995), Increased levels of substance P and calcitonin gene-related peptide in rat adjuvant arthritis. A combined immunohistochemical and radioimmunoassay analysis. Arthritis Rheum. 38:699-709.

A. A. al-Hamidi, A. S. Riskuwa, S. D. Ali, (1997), Inhibition of camel lens zeta-crystallin/NADPH:quinone oxidoreductase activity by chloranilic acid. Biochem. Mol. Biol. Int. 41:415-421.

J. Allsop and R. W. Watts, (1980), Activities of amidophosphoribosyltransferase and purine phosphoribosyltransferases in developing rat brain. Adv. Exp. Med. Biol. 122A:361-366.

C. Aoki, T. A. Milner, S. B. Berger, K. F. Sheu, J. P. Blass, and V. M. Pickel, (1987), Glial glutamate dehydrogenase: ultrastructural localization and regional distribution in relation to the mitochondrial enzyme, cytochrome oxidase. J. Neurosci. Res. 18:305-318.

C. Arce, S. Canadas, M. J. Oset-Gasque, E. Castro, and M. P. Gonzalez, (1990), Glutamate dehydrogenase: some properties of the rat brain enzyme from different cellular compartments. Comp. Biochem. Physiol. C. 97:265-267.

Attwood P V, Graneri B D, Bicarbonate-dependent ATP cleavage catalysed by pyruvate carboxylase in the absence of pyruvate. Biochem J. 287 ( Pt 3):1011-7, 1992.

B. Ault and L. M. Hildebrand, (1993a), L-glutamate activates peripheral nociceptors. Agents Actions 39:C142-144.

B. Ault and L. M. Hildebrand, (1993b), Activation of nociceptive reflexes by peripheral kainate receptors. J. Pharmacol. Exp. Ther. 265:927-932.

Bahl J J, Matsuda M, DeFronzo R A, Bressler R, In vitro and in vivo suppression of gluconeogenesis by inhibition of pyruvate carboxylase. Biochem Pharmacol. 53(1):67-74, 1997.

G. Battaglia and A. Rustioni, (1988), Coexistence of glutamate and substance P in dorsal root ganglion neurons of the rat and monkey. J. Comp. Neurol. 277:302-312.

M. D. Bazzi, N. Rabbani, and A. S. Duhaiman, (2002), Sequential inactivation of zeta-crystallin by o-phthalaldehyde. Biochim Biophys. Acta 1597:67-73.

S. Beardsley, S. Kunjara, and A. L. Greenbaum, (1988), Enzymes of the pathway of purine synthesis in the rat mammary gland. Changes in the lactation cycle and the effects of diabetes. Biochem. J. 250:395-399.

J. M. Besson and G. Guilbaud, (1988), The Arthritic Rat as a Model of Chronic Pain? Elsevier, Amsterdam.

J. M. Besson,(1999), The neurobiology of pain. Lancet 353:1610-1615.

G. Bhave, F. Karim, S. M. Carlton, and R. W. Gereau 4th, (2001), Peripheral group I metabotropic glutamate receptors modulate nociception in mice. Nat Neurosci. 4:417-423.

S. C. Bledsoe, Jr., R. P. Bobbin, R. Thalmann, and I. Thalmann, (1980), Stimulus-induced release of endogenous amino acids from skins containing the lateral-line organ in *Xenopus laevis*. Exp. Brain Res. 40:97-101.

H. F. Bradford, H. K. Ward, and P. Foley, (1989), Glutaminase inhibition and the release of neurotransmitter glutamate from synaptosomes. Brain Res. 476:29-34.

Broeder J A, Smith C H, Moe A J, Glutamate oxidation by trophoblasts in vitro. Am J Physiol. 267(1 Pt 1):C189-94, 1994.

S. Bröer and N. Brookes, (2001), Transfer of glutamine between astrocytes and neurons. J Neurochem. 77:705-719.

G. Burnstock, (1996), A unifying purinergic hypothesis for the initiation of pain. Lancet 347:1604-1605.

L. Calzà, M. Pozza, M. Zanni, C. U. Manzini, E. Manzini, and T. Hökfelt, (1998), Peptide plasticity in primary sensory neurons and spinal cord during adjuvant-induced arthritis in the rat: An immunocytochemical and in situ hybridization study. Neuroscience 82:575-589.

A. A. Cameron, J. D. Leah, and P. J. Snow, (1986), The electrophysiological and morphological characteristics of feline dorsal root ganglion cells. Brain Res. 362:1-6.

J. N. Campbell, (1987), Peripheral neural mechanisms of nociception. In The Textbook of Pain, P. D. Wall, R. Meizack, Churchill-Livingstone.

C. B. Cangro, P. M. Sweetnam, J. H. Neale, W. G. Haser, and N. P. Curthoys, (1984), Selective localization of glutaminase in spinal and sensory nerve cells. A potential marker for glutamate neurotransmission. JAMA 251:797.

C. B. Cangro, P. M. Sweetnam, J. R. Wrathall, W. G. Haser, N. P. Curthoys, and J. H. Neale, (1985), Localization of elevated glutaminase immunoreactivity in small DRG neurons. Brain Res. 336:158-161.

S. M. Carlton, G. L. Hargett, and R. E. Coggeshall, (1995), Localization and activation of glutamate receptors in unmyelinated axons of rat glabrous skin. Neurosci. Lett. 197:25-28.

S. M. Carlton, S. Zhou, and R. E. Coggeshall, (1998), Evidence for the interaction of glutamate and NK1 receptors in the periphery. Brain Res. 790:160-169.

S. M. Carlton and R. E. Coggeshall, (1999), Inflammation-induced changes in peripheral glutamate receptor populations. Brain Res., 820:63-70.

Caughey W S, Smiley J D, Hellerman L, J. Biol. Chem 224:591-607, 1957.

M. Cesar and B. Hamprecht, (1995), Immunocytochemical examination of neural rat and mouse primary cultures using monoclonal antibodies raised against pyruvate carboxylase. J. Neurochem. 64:2312-2318.

S. W. Cho, J. Lee, S. Y. Choi, (1995), Two soluble forms of glutamate dehydrogenase isoproteins from bovine brain, Eur. J. Biochem. 233:340-346.

S. W. Cho, J. Y. Ahn, J. Lee, and S. Y. Choi, (1996), Identification of a peptide of the guanosine triphosphate binding site within brain glutamate dehydrogenase isoproteins using 8-azidoguanosine triphosphate. Biochemistry 35:13907-13913.

R. E. Coggeshall and S. M. Carlton, (1998), Ultrastructural analysis of NMDA, AMPA, and kainate receptors on unmyelinated and myelinated axons in the periphery. J. Comp. Neurol. 391:78-86.

A. D. Colon, A. Plaitakis, S. Berl, and D. D. Clarke, (1986), Purification and characterization of a soluble and a particulate glutamate dehydrogenase from rat brain. J. Neurochem. 46:1811-1819.

F. Conti and A. Minelli, (1994), Glutamate immunoreactivity in rat cerebral cortex is reversibly abolished by 6-diazo-5-oxo-L-norleucine (DON), an inhibitor of phosphate-activated glutaminase. J Histo Cytochem. 42:717-726.

A. J. L. Cooper, (1988), Glutamine synthetase, in: E. Kvamme (Ed.), Glutamine and Glutamate in Mammals. CRC Press, Boca Raton, pp. 7-31.

J. V. Cross, J. C. Deak, E. A. Rich, Y. Qian, M. Lewis, L. A. Parrott, K. Mochida, D. Gustafson, S. Vande Pol, and D. J. Templeton, (1999), Quinone reductase inhibitors block SAPK/JNK and NFkappaB pathways and potentiate apoptosis. J Biol Chem. 274:31150-31154.

N. P. Curthoys and O. H. Lowry, (1973), The distribution of glutaminase isoenzymes in the various structures of the nephron in normal, acidotic, and alkalotic rat kidney. J. Biol. Chem. 248:162-168.

N. P. Curthoys, T. Kuhlenschmidt, S. S. Godfrey, and R. F. Weiss, (1976), Phosphate-dependent glutaminase from rat kidney. Cause of increased activity in response to acidosis and identity with glutaminase from other tissues. Arch Biochem Biophys. 172:162-167.

N. P. Curthoys and M. Watford, (1995), Regulation of glutaminase activity and glutamine metabolism. Annu. Rev. Nutr. 15:133-159.

N. P. Curthoys and G. Gstraunthaler, (2001), Mechanism of increased renal gene expression during metabolic acidosis. Am J Physiol Renal Physiol. 281:F381-390.

N. C. Danbolt, F. A. Chaudhry, Y. Dehnes, K. P. Lehre, L. M. Levy, K. Ullensvang, and J. Storm-Mathisen, (1998), Properties and localization of glutamate tranporters. Prog. Brain Res. 116:23-43.

E. M. Davidson, R. E. Coggeshall, and S. M. Carlton, (1997), Peripheral NMDA and non-NMDA glutamate receptors contribute to nociceptive behaviors in the rat formalin test. Neuroreport 8:941-946.

S. De Biasi and A. Rustioni, (1988), Glutamate and substance P coexist in primary afferent terminals in the superficial laminae of spinal cord. Proc. Natl. Acad. Sci. U.S.A. 85:7820-7824.

J. deGroot, S. Zhou, and S. M. Carlton, (2000), Peripheral glutamate release in the hindpaw following low and high intensity sciatic stimulation. Neuroreport 11:497-502.

A. H. Dickenson, (1995), Central acute pain mechanisms. Ann. Med. 27:223-227.

L. F. Donaldson, A. J. Harmar, D. S. McQueen, and J. R. Seckl, (1992), Increased expression of preprotachykinin, calcitonin gene-related peptide, but not vasoactive intestinal peptide messenger RNA in dorsal root ganglia during the development of adjuvant monoarthritis in the rat. Brain Res. Mol. 16:143-149.

Dranoff G, Elion G B, Friedman H S, Campbell G L, Bigner D D, Influence of glutamine on the growth of human glioma and medulloblastoma in culture. Cancer Res. 45(9): 4077-81, 1985.

I. R. Duce and P. Keen, (1983), Selective uptake of [$_3$H] glutamine and [$_3$H]glutamate into neurons and satellite cells of dorsal root ganglia in vitro. Neuroscience 8:861-866.

M. Erecinska, M. M. Zaleska, D. Nelson, I. Nissim, and M. Yudkoff, (1990), Neuronal glutamine utilization: glutamine/glutamate homeostasis in synaptosomes. J. Neurochem. 54:2057-2069.

M. Eybalin, M. D. Norenberg, and N. Renard, (1996), Glutamine synthetase and glutamate metabolism in the guinea pig cochlea. Hear Res. 101:93-101.

Fang J, Hsu B Y, MacMullen C M, Poncz M, Smith T J, Stanley C A, Expression, purification and characterization of human glutamate dehydrogenase (GDH) allosteric regulatory mutations. Biochem J. 363(Pt 1):81-7, 2002.

Farfari S, Schulz V, Corkey B, Prentki M, Glucose-regulated anaplerosis and cataplerosis in pancreatic beta-cells:

possible implication of a pyruvate/citrate shuttle in insulin secretion. Diabetes 49(5):718-26, 2000.

D. Fell, (1997), Understanding the Control of Metabolism. In: K. Snell, (Series Ed.) Frontiers of Medicine Series. Portland Press, London and Miami, pp 101-193, 225-252.

F. Fonnum, (1991), Neurochemical studies on glutamate-mediated neurotransmission. in Excitatory Amino Acids, B S Meldrum, F Moroni, R P Simon, J H Woods, eds, pp 15-25, Raven Press, New York.

Fushiya S, Maeda K, Funayama T, Nozoe S, 4-N-hydroxy-L-2,4-diaminobutyric acid. A strong inhibitor of glutamine synthetase. J Med Chem. 31(2):480-3, 1988.

E. M. Fykse and F. Fonnum, (1996), Amino acid neurotransmission: dynamics of vesicular uptake. Neurochem Res. 21:1053-1060.

W. C. Gamberino, D. A. Berkich, C. J. Lynch, B. Xu, and K. F. LaNoue, (1997), Role of pyruvate carboxylase in facilitation of synthesis of glutamate and glutamine in cultured astrocytes. J. Neurochem. 69:2312-2325.

N. E. Garrett, B. L. Kidd, S. C. Cruwys, and D. R. Tomlinson, (1995), Changes in preprotachykinin mRNA expression and substance P levels in dorsal root ganglia of monoarthritic rats: comparison with changes in synovial substance P levels. Brain Res. 675:203-207.

M. G. Garry, K. E. Miller, and V. S. Seybold, (1989), Lumbar dorsal root ganglia of the cat: a quantitative sudy of peptide immunoreactivity and cell size. J. Comp. Neurol. 284:36-47.

P. G. Genever, S. J. Maxfield, G. D. Kennovin, J. Maltman, C. J. Bowgen, M. J. Raxworthy, and T. M Skerry, (1999), Evidence for a novel glutamate-mediated signaling pathway in keratinocytes. J. Invest. Dermatol. 112:337-342.

Gill H S, Eisenberg D, The crystal structure of phosphinothricin in the active site of glutamine synthetase illuminates the mechanism of enzymatic inhibition. Biochemistry. 40(7): 1903-12, 2001.

H. J. Gould 3rd, J. D. England, Z. P. Liu, and S. R. Levinson, (1998), Rapid sodium channel augmentation in response to inflammation induced by complete Freund's adjuvant. Brain Res. 802:69-74.

L. T. Graham, Jr and M. H. Aprison, (1969), Distribution of some enzymes associated with the metabolism of glutamate, aspartate, gammaaminobutyrate and glutamine in cat spinal cord. J. Neurochem. 16:559-566.

G. Gstraunthaler, T. Holcomb, E. Feifel, W. Liu, N. Spitaler, and N. P. Curthoys, (2000), Differential expression and acid-base regulation of glutaminase mRNAs in LLC-PK(1)-FBPase(+) cells. Am. J. Physiol. Renal Physiol. 278:F227-237.

U. Hanesch, U. Pfrommer, B. D. Grubb, B. Heppelmann, and H. G. Schaible, (1993), The proportion of CGRP-immunoreactive and SP-mRNA containing dorsal root ganglion cells is increased by a unilateral inflammation of the ankle joint of the rat. Regul. Pept. 46:202-203.

U. Hanesch, F. Blecher, R. U. Stiller, P. C. Emson, B. Heppelmann, and H. G. Schaible, (1995), The effect of unilateral inflammation at the rat=s ankle joint on the expression of preprotachykinin-A mRNA and preprosomatostatin mRNA in dorsal root ganglion cells—a study using non-radioactive in situ hybridization. Brain Res. 700:279-284.

W. R. Hansen, N. Barsic-Tress, L. Taylor, and N. P. Curthoys, (1996), The 3'-nontranslated region of rat renal glutaminase mRNA contains a pHresponsive stability element. Am. J. Physiol. 271:F126-131.

K. Hargreaves, R. Dubner, F. Brown, C. Flores, and J. Joris, (1988), A new and sensitive method for measuring thermal nociception in cutaneous hyperalgesia. Pain 32:77-88.

A. A. Harper and S. N. Lawson, (1985), Conduction velocity is related to morphological cell type in rat dorsal root ganglion neurons. J. Physiol. 359:31-46.

B. Hassel and A. Bråthe, (2000), Neuronal pyruvate carboxylation supports formation of transmitter glumate. J. Neurosci. Res. 20:1342-1347.

L. Hertz, R. Dringen, A. Schousboe, and S. R. Robinson, (1999), Astrocytes: glutamate producers for neurons. J. Neurosci. Res. 57:417-432.

T. Holcomb, L. Taylor, J. Trohkimoinen, and N. P Curthoys, (2000), Isolation, characterization and expression of a human brain mitochondrial glutaminase cDNA. Brain Res. Mol. Brain Res. 76:56-63.

P. M. Hollander and L. Ernster, (1975), Studies on the reaction mechanism of DT diaphorase. Action of dead-end inhibitors and effects of phospholipids. Arch. Biochem. Biophys. 169:560-567.

S. Hosoda, W. Nakamura, K. Hayashi, (1974), Properties and reaction mechanism of DT diaphorase from rat liver. J. Biol. Chem. 249:6416-6423.

Hulsmann S, Straub H, Richter D W, Speckmann E J, Blockade of astrocyte metabolism causes delayed excitation as revealed by voltage-sensitive dyes in mouse brainstem slices.

Exp Brain Res. 150(1):117-21, 2003.

M. J. Iadarola, J. Douglass, O. Civelli, and J. R. Naranjo, (1988), Differential activation of spinal cord dynorphin and enkephalin neurons during hyperalgesia: evidence using cDNA hybridization. Brain Res. 455:205-212.

I. Inagaki, Y. Kamisaki, H. Kiyama, Y. Horio, M. Tohyama, and H. Wada, (1987), Immunocytochemical localizations of cytosolic and mitochondrial glutomic oxaloacetic transaminase isozymes in rat primary sensory neurons as a marker for the glutamate neuronal system. Brain Res. 402:197-200.

M. Itakura, N. Maeda, M. Tsuchiya, and K. Yamashita, (1986), Increased rate of de novo purine synthesis and its mechanism in regenerating rat liver. Am. J. Physiol. 251: G585-590.

D. L. Jackson, L. M. Aanonsen, J. D. Richardson, H. Geier, and K. M. Hargreaves, (1993), An evaluation of the effects of excitatory amino acids in bovine dental pulp. Proc. Soc. Neurosci. 19:996.

D. L. Jackson, C. B. Graff, J. D. Richardson, and K. M. Hargreaves, (1995), Glutamate participates in the peripheral modulation of thermal hyperalgesia in rats. Eur. J. Pharmacol. 284:321-325.

A. K. Jaiswal, (2000), Characterization and partial purification of microsomal NAD(P)H:quinone oxidoreductases. Arch. Biochem. Biophys. 375:62-68.

K. R. Jessen and R. Mirsky, (1983), Astrocyte-like glia in the peripheral nervous system: an immunohistochemical study of enteric glia. J. Neurosci. 3:2206-2218.

S. Jitrapakdee, M. E. Walker, and J. C. Wallace, (1996), Identification of novel alternatively spliced pyruvate carboxylase mRNAs with divergent 5'-untranslated regions which are expressed in a tissue-specific manner. Biochem. Biophus. Res. Commun. 223:695-700.

S. Jitrapakdee, G. W. Booker, A. I. Cassady, and J. C. Wallace, (1997), The rate pyruvate carboxylase gene structure. Alternate promoters generate multiple transcripts with the 5'-end heterogeneity. J. Biol. Chem. 272:20522-25030.

J. L. Johnson, (1972), An analysis of the activities of 3 key enzymes concerned with the interconversion of a-ketoglutarate and glutamate: correlations with free glutamate levels in 20 specific regions of the nervous system. Brain Res. 45:205-215.

J. L. Johnson, (1974), An analysis of the compartmentation and proximodistal convection of the glutamate-glutamine system in the dorsal sensory neuron: comparison with the motoneuron and cerebral cortex. Brain Res. 67:489-502.

J. L. Johnson, (1974), Glutamine in the dorsal sensory neuron. Brain Res. 69:366-369.

J. L. Johnson, (1976), A comparative analysis of compartmentation of metabolism in the dorsal root ganglion and ventral spinal cord gray using [U-$_{14}$C] glucose, [2-$_{14}$C] glucose, [6-$_{14}$C]glucose, [3,4-$_{14}$C] glucose, NaH$_{14}$CO$_3$, and [2-$_{14}$C] pyruvate, Brain Res. 101:523-532.

T. Kaneko, H. Akiyama, and N. Mizuno, (1987), Immunohistochemical demonstration of glutamate dehydrogenase in astrocytes. Neurosci. Lett. 77:171-175.

T. Kaneko, R. Shigemoto, and N. Mizuno, (1988), Metabolism of glutamate and ammonia in astrocyte: an immunocytochemical study. Brain Res. 457:160-164.

T. Kaneko, A. Hanazawa, and N. Mizuno, (1992), Enhancement of glutaminase-like immunoreactivity in rat brain by an irreversible inhibitor of the enzyme. Brain Res. Bull 28:897-907.

H. Kato, T. Yamamoto, H. Yamamoto, R. Ohi, N. So, and Y. Iwasaki, (1990), Immunocytochemical characterization of supporting cells in the enteric nervous system in Hirschsprung's disease. J. Pediatr. Surg. 25:514-519.

T. Kato and O. H. Lowry, (1973), Distribution of enzymes between nucleus and cytoplasm of single nerve cell bodies. J. Biol. Chem. 248:2044-2048.

P. Keen and P. J. Roberts, (1974), Uptake and compartmentation of glutamic acid in sensory ganglia. Br. J. Pharmacol. 51:136P.

Kiersztan A, Jarzyna R, Bryla J, Inhibitory effect of vanadium compounds on glutamate dehydrogenase activity in mitochondria and hepatocytes isolated from rabbit liver. Pharmacol. Toxicol. 82:167-172, 1998.

J. H. Kim, J. M. Krahn, D. R. Tomchick, J. L. Smith, and H. Zalkin, (1996), Structure and function of the glutamine phosphoriboslypyrophosphate amidotransferase glutomine site and communication with the phosphoribosylpyrophosphate site. J. Biol. Chem. 271:15549-15557.

M. Koltzenburg, D. L. Bennett, D. L. Shelton, and S. B. McMahon, (1999), Neutralization of endogenous NGF prevents the sensitization of nociceptors supplying inflamed skin. Eur J Neurosci. 11: 1698-1704.

Z. Kraśnicka, (1970), Morphology and histochemistry of neurons of the dorsal root ganglia in tissue culture and in embryonal development. Pol. Med. J. 9:1258-1297.

N. Kuo, M. Michalik, and M. Erecinska, (1994), Inhibition of glutamate dehydrogenase in brain mitochondria and synaptosomes by $Mg_{2+}$ and polymines: a possible cause for its low in vivo activity. J. Neurochem. 63:751-757.

E. Kvamme and I. A. Torgner, (1975), Regulatory effects of fatty acyl-coenzyme A derivatives on phosphate-activated pig brain and kidney glutaminase in vitro. Biochem J. 149:83-91.

E. Kvamme and B. E. Olsen, (1979), Evidence for two species of mammalian phosphateactivated glutaminase having different regulatory properties. FEBS Lett. 107:33-36.

E. Kvamme and K. Lenda, (1982), Regulation of glutaminase by exogenous glutamate, ammonia and 2-oxoglutarate in synaptosomal enriched preparation from rat brain. Neurochem. Res. 7:667-78.

E. Kvamme, G. Svenneby, and I. A. Torgner, (1983), Calcium stimulation of glutamine hydrolysis in synaptosomes from rat brain. Neurochem. Res. 8:25-38.

E. Kvamme, I. A. Torgner, and B. Roberg, (1991), Evidence indicating that pig renal phosphate-activated glutaminase has a functionally predominant external localization in the inner mitochondrial membrane. J. Biol. Chem. 266: 13185-13192.

E. Kvamme, (1998), Synthesis of glutamate and its regulation. Prog. Brain Res. 116:73-85.

Lai J C, Liang B B, Jarvi E J, Cooper A J, Lu D R, Differential effects of fatty acyl coenzyme A derivatives on citrate synthase and glutamate dehydrogenase. Res Commun Chem Pathol Pharmacol. 82(3):331-8, 1993.

P. R. Laming, (1998), Changing concepts on the role of glia, in: P. R. Laming, E. Syková, A. Reichenbach, G. I Hatton, H. Bauer (Eds.), Glial Cells. Their role in Behaviour. Cambridge University Press, Cambridge, pp. 1-21.

O. F. Laterza, W. R. Hansen, L. Taylor, and N. P. Curthoys, (1997), Identification of an mRNA-binding protein and the specific elements that may mediate the pH-responsive induction of renal glutaminase mRNA. J. Biol. Chem. 272:22481-22488.

O. F. Laterza and N. P. Curthoys, (2000), Specificity and functional analysis of the pH-responsive element within renal glutaminase mRNA. Am. J. Physiol. Renal Physiol. 278: F970-977.

N. B. Law, W. D. Willis, and K. N. Westlund, (1997), Excitatory amino acid receptor involvement in peripheral nociceptive transmission in rats. Eur. J. Pharmacol. 324:169-177.

N. B. Law, T. McNearney, and K. N. Westlund, (2000), Amino acid release into the knee joint: key role in nociception and inflammation. Pain 86:69-74.

J. Lee, S. W. Kim, and S. W. Cho, (1995), A novel glutamate dehydrogenase from bovine brain: purification and characterization. Biochem. Mol. Biol. Int. 36:1087-1096.

R. W. Leech, (1967), Changes in satellite cells of rat dorsal root ganglia during central chromatolysis. An electron microscopic study. Neurology 17:349-358.

G. C. Leo, B. F. Driscoll. R. P. Shank, and E. Kaufman, (1993), Analysis of [1-$^{13}$C] D-glucose metabolism in cultured astrocytes and neurons using nuclear magnetic resonance spectroscopy. Dev. Neurosci. 15:282-288.

S. Li, J. L. Smith, and H. Zalkin, (1999), Mutational analysis of Bacillus subtilis glutamine phosphoribosylpyrophosphate amidotransferase propeptide processing. J. Bacteriol. 181:1403-1408.

O. H. Lowry and J. V. Passonneau, (1972), in: A Flexible System of Enzymatic Analysis, 1st Edition, Academic Press, London, pp 220-260.

J. E. Madl, J. R. Clements, A. J. Beitz, R. J. Wenthold, and A. A. Larson, (1988), Immunocytochemical localization of glutamate dehydrogenase in mitochondria of the cerebellum: an ultrastructural study using a monoclonal antibody. Brain Res. 452:396-402.

M. Malcangio, N. E. Garrett, and D. R. Tomlinson, (1997), Nerve growth factor treatment increases stimulus-evoked release of sensory neuropeptides in the rat spinal cord. Eur J Neurosci 9:1101-1104.

L. Marlier, P. Poulat, N. Rajaofetra, and A. Privat, (1991), Modifications of serotonin, substance P and calcitonin gene-related peptide-like immunoreactivities in the dorsal horn of the spinal cord of arthritic rats: a quantitative immunocytochemical study. Exp. Brain Res. 83:482-490.

D. L. Martin and R. A. Waniewski, (1996), Precursor synthesis and neurotransmitter uptake by astrocytes as targets of neurotoxicants, in: M. Aschner, H. K. Kimelberg (Eds.), The Role of Glia in Neurotoxicity. CRC Press, Boca Raton, pp. 335-357.

Martin-Requero A, Ayuso M S, Parrilla R, Rate-limiting steps for hepatic gluconeogenesis. Mechanism of oxamate inhibition of mitochondrial pyruvate metabolism. J Biol Chem. 261(30):13973-8, 1986.

Matsuno T, Satoh T, Suzuki H, Prominent glutamine oxidation activity in mitochondria of avian transplantable hepatoma induced by MC-29 virus. J Cell Physiol. 128(3): 397-401, 1986.

D. B. McDougal Jr., M. J. C. Yu, P. D. Gorin, and E. M. Johnson Jr., (1981), Transported enzymes in sciatic nerve and sensory ganglia of rats exposed to maternal antibodies against nerve growth factor. J. Neurochem. 6:1847-1852.

A. Merighi, J. M. Polak, and D. T Theodosis, (1191), Ultrastructural visualization of glutamate and aspartate immunoreactivities in the rat dorsal horn, with special reference to the co-localization of glutamate, substance P, and calcitonin gene-related peptide. Neuroscience 160:113-116.

L. J. Messenger and H. Zalkin, (1979), Glutamine phosphoribosylpyrophosphate amidotransferase from *Escherichia coli*. Purification and properties. J. Biol. Chem. 254: 3382-3392.

M. J. Millan, (1999), The induction of pain: An integrative review. Prog. Neurobiol. 57:1-164.

K. E. Miller, V. D. Douglas, and T. Kaneko, (1993), Glutaminase immunoreactive neurons in the rat dorsal root ganglion contain calcitonin generelated peptide (CGRP). Neurosci. Lett. 160:113-116.

K. E. Miller, R. M. Kriebel, M. J. Chandler, C. D. Ross, and R. D. Foreman, (1999a), Glutamate- and glutaminase-immunoreactive nerve fibers in rat skin following peripheral inflammation. Proc. Soc. Neurosci. 25:685.

K. E. Miller, E. Akesson, and A. Seiger, (1999b), Nerve growth factor-induced stimulation of dorsal root ganglion/spinal cord co-grafts in oculo: enhanced survival and growth of CGRPimmunoreactive sensory neurons. Cell Tissue Res. 298:243-253.

K. E. Miller, S. R. Caire, R. W. Dennis, M. J. Chandler, R. D. Foreman, and R. M. Kriebel, (2001), Effects of Nerve Growth Factor (NGF) on Glutamate Metabolism in Rat Primary Sensory Neurons. Proc. Soc. Neurosci.

K. E. Miller, B. A. Richards, and R. M. Kriebel, (2002a), Glutamine-, glutamine synthetase-, glutamate dehydrogenase- and pyruvate carboxylase-immunoreactivities in the rat dorsal root ganglion and peripheral nerve. Brain Res. 945: 202-211.

K. E. Miller, B. A. Richards, S. Hopkins, R. M. Kriebel, and R. D. Foreman, (2002b), Increases in glutamate- and glutaminase-immunoreactivity in rat primary afferent peripheral terminals following inflammation. Neuroscience submitted.

M. C. W. Minchin and P. M. Beart, (1975), Compartmentation of amino acid metabolism in the rat dorsal root ganglion; a metabolic and autoradiographic study. Brain Res. 83:437-449.

H. Mulder, Y. Zhang, N. Danielsen, and F. Sundler, (1997), Islet amyloid polypeptide and calcitonin gene-related peptide expression are upregulated in lumbar dorsal root ganglia after unilateral adjuvant-induced inflammation in the rat paw. Brain Res. Mol. Brain Res. 50:127-135.

H. Mulder, H. Jongsma, Y. Zhang, S. Gebre-Medhin, F. Sundler, and N. Danielsen, (1999), Pituitary adenylate cyclase-activating polypeptide and islet amyloid polypeptide in primary sensory neurons: functional implications from plasticity in expression on nerve injury and inflammation. Mol. Neurobiol. 19:229-253.

R. L. Nahin and M. R. Byers, (1994), Adjuvant-induced inflammation of rat paw is associated with altered calcitonin gene-related peptide immunoreactivity within cell bodies and peripheral endings of primary afferent neurons. J. Comp. Neurol. 349:475-485.

R. S. Nicholas, J. Winter, P. Wren, R. Bergmann, and C. J. Woolf, (1999), Peripheral inflammation increases the capsaicin sensitivity of dorsal root ganglion neurons in a nerve growth factor-dependent manner. Neuroscience 91:1425-1433.

K. Noguchi, Y. Morita, H. Kiyama, K. Ono, and M. Tohyama, (1988), A noxious stimulus induces the preprotachykinin-A gene expression in the rat dorsal root ganglion: a quantitative study using in situ hybridization histochemistry. Molec. Brain Res. 4:31-35.

L. Pellerin, G. Pellegri, P. G. Bittar, Y. Charnay, C. Bouras, J. L. Martin, N. Stella, and P. J. Magistretti, (1998), Evidence supporting the existence of an activity-dependent astrocyte-neuron lactate shuttle. Dev. Neurosci. 20:291-299.

G. M. Pitcher, J. Ritchie, and J. L Henry, (1997), Paw withdrawal threshold in the von Frey hair test is influenced by the surface on which the rat stands. J. Neurosci. Methods 87:185-193.

G. M. Pitcher, J. Ritchie, and J. L. Henry, (1999), Nerve constriction in the rat: model of neuropathic, surgical and central pain. Pain 83:37-46.

S. Pockett, (1995), Spinal cord synaptic plasticity and chronic pain. Anesth. Analg. 80:173-179.

M. J. Politis and J. E. Miller, (1985), Post-traumatic alterations in glutamine synthetase activity in peripheral and central nervous nerves. Brain Res. 359:183-186.

Pons M, Michel F, Descomps B, Crastes de Paulet A, Structural requirements for maximal inhibitory allosteric effect of estrogens and estrogen analogues on glutamate dehydrogenase. Eur J Biochem. 84(1):257-66, 1978.

L. D. Porter, H. Ibrahim, L. Taylor, and N. P. Curthoys, (2002), Complexity and species variation of the kidney-type glutaminase gene. Physiol Genomics 9:157-166.

T. Preiss, A. G. Hall, and R. N. Lightowlers, (1993), Identification of bovine glutamate dehydrogenase as an RNA-binding protein. J. Biol. Chem. 268:24523-24526.

T. Preiss, A. E. Sang, Z. M. Chrzanowska-Lightowlers, and R. N. Lightowlers, (1995), The mRNA-binding protein COLBP is glutamate dehydrogenase. FEBS Lett. 367:291-296.

N. Rabbani and A. S. Duhaiman, (1998), Inhibition of camel lens zetacrystallin/NADPH:quinone oxidoreductase by pyridoxal-5'-phosphate. Biochem. Biophys. Acta 1388: 175-180.

A. Reinert, A. Kaske, and S. Mense, (1998), Inflammation-induced increase in the density of neuropeptide-immunoreactive nerve endings in rat skeletal muscle. Exp. Brain Res. 121:174-180.

P. J. Roberts and P. Keen, (1973), Uptake of [$^{14}$C]glutamate into dorsal and ventral roots of spinal nerves of the rat. Brain Res. 57:234-238.

P. J. Roberts and P. Keen, (1974), [$^{14}$C]Glutamate uptake and compartmentation in glia of rat dorsal sensory ganglion. J. Neurochem. 23:201-209.

P. J. Roberts, (1974), Amino acid release from isolated rat dorsal root ganglia. Brain Res. 74:327-332.

S. R. Robinson, A. Schousboe, R. Dringen, P. Magistretti, J. Coles, and L. Hertz, (1998), Metabolic trafficking between neurons and glia, in: P. R. Laming, E. Syková, A. Reichenbach, G. I. Hatton, H. Bauer (Eds.), Glial Cells. Their Role in Behavior. Cambridge University Press, Cambridge, pp. 83-106.

M. Rohde, F. Lim, J. C. Wallace, (1991), Electron microscopic localization of pyruvate carboxylase in rat liver and

*Saccharomyces cerevisiae* by immunogold procedures. Arch. Biochem. Biophys. 290:197-201.

Ronzio R A, Rowe W B, Meister A, Studies on the mechanism of inhibition of glutamine synthetase by methionine sulfoximine. Biochemistry 8(3): 1066-75, 1969.

F. Rothe, G. Wolf, and G. Schunzel, (1990), Immunohistochemical demonstration of glutamate dehydrogenase in the postnatally developing rat hippocampal formation and cerebellar cortex: comparasion to activity staining. Neuroscience 39:419-429.

F. Rothe, M. Brosz, and J. Storm-Mathisen, (1994), Quantitative ultrastructural localization of glutamate dehydrogenase in the rat cerebellar cortex. Neuroscience 62:1133-1146.

C. N. Sang, M. P. Hostetter, R. H. Gracely, A. S. Chappell, D. D. Schoepp, G. Lee, S. Whitcup, R. Caruso, and M. B. Max, (1988), AMPA/kainate antagonist LY293558 reduces capsaicin-evoked hyperalgesia but not pain in normal skin in humans. Anesthesiology 89:1060-1067.

L. P. Schelonka, D. Siegel, M. W. Wilson, A. Meininger, and D. Ross, (2000), Immunohistochemical localization of NQO1 in epithelial dysplasia and neoplasia and in donor eyes. Invest. Ophthalmol. Vis. Sci. 41:1617-1622.

A. Schmitt and P. Kugler, (1999), Cellular and regional expression of glutamate dehydrogenase in the rat nervous system: non-radioactive in situ hybridization and comparative immunocytochemistry. Neuroscience 92:293-308.

S. P. Schneider and E. R. Perl, (1988), Comparison of primary afferent and glutamate excitation of neurons in the mammalian spinal dorsal horn. J. Neurosci. 8:2062-2073.

Sellinger O Z, Inactivation of cerebral glutamine synthetase by DL-methionine-DL-sulfoximine. Biochim Biophys Acta. 132(2):514-6, 1967.

V. S. Seybold, M. T. Galeazza, M. G. Garry, and K. M. Hargreaves, (1995), Plasticity of calcitonin gene related peptide neurotransmission in the spinal cord during peripheral inflammation. Can. J. Physiol. Pharmacol. 73:1007-1014.

R. P. Shank, G. S. Bennett, S. O. Freytag, and G. L. Campbell, (1985), Pyruvate carboxylase: an astrocyte-specific enzyme implicated in the replenishment of amino acid neurotransmitter pools. Brain Res. 329:364-367.

R. P. Shank and D. J. Bennett, (1993), 2-Oxoglutarate transport: a potential mechanism for regulating glutamate and tricarboxylic acid cycle intermediates in neurons. Neurochem. Res. 18:410.

R. A. Shapiro, V. M. Clark, and N. P. Curthoys, (1978), Covalent interaction of L-2-amino-4-oxo-5-chloropentanoic acid with rat renal phosphate-dependent glutaminase. Evidence for a specific glutamate binding site and of subunit heterogeneity. J. Biol. Chem. 253:7086-7090.

R. A. Shapiro, V. M. Clark, and N. P. Curthoys, (1979), Inactivation of rat renal phosphate-dependent glutaminase with 6-diazo-5-oxo-L-norleucine. Evidence for interaction at the glutamine binding site. J. Biol. Chem. 254:2835-2838.

D. Siegel and D. Ross, (2000), Immunodetection of NAD(P)H:quinone oxido-reductase 1 (NQO1) in human tissues. Free Radic Biol. Med. 29:246-253.

G. J. Siegel, B. W. Agranoff, R. W. Albers, S. K. Fisher, and M. D. Uhler, (1999), (Eds.), Basic Neurochemistry. Molecular, Cellular and Medical Aspects, 6$^{th}$ Edition, Lippincott-Raven. Philadelphia, pp. 1183.

S. R. Skilling, D. H. Smullin, A. J. Beitz, and A. A. Larson, (1988), Extracellular amino acid concentrations in dorsal spinal cord of freely moving rats following veratridine and nociceptive stimulation. J. Neurochem. 51:127-132.

K. A. Sluka, K. N. Westlund, Y. C. Sun, P. M. Dougherty, L. S. Sorkin, and W. D. Willis, (1992), Neural changes in acute arthritis in monkeys. III. Changes in substance P. calcitonin gene-related peptide and glutamate in the dorsal horn of the spinal cord. Brain Res. Rev. 17:29-38.

K. A. Sluka and K. N. Westlund, (1993), Spinal cord amino acid release and content in an arthritis model: the effects of pretreatment with non-NMDA, NMDA, and NK1 receptor antagonists. Brain Res. 627:89-103.

G. D. Smith, A. J. Harmar, D. S McQueen, and J. R. Seckl, (1992), Increase in substance P and CGRP, but not somatostatin content of innervating dorsal root ganglia in adjuvant monoarthritis in the rat. Neurosci. Lett. 137:257-260.

J. L. Smith, (1998), Glutamine PRPP amidotransferase: snapshots of an enzyme in action. Curr. Opin. Struct. Biol. 8:686-694.

L. S. Sorkin, K. N. Westlund, K. A. Sluka, P. M. Dougherty, and W. D. Willis, (1992), Neural changes in acute arthritis in monkeys. IV. Time course of amino acid release into the lumbar dorsal horn. Brain Res. Rev. 17:39-50.

B. Stevens, S. Tanner, and R. D. Fields, (1998), Control of myelination by specific patterns of neural impulses. J. Neurosci. 18:9303-9311.

I. Stoyanova, A. Dandov, N. Lazarov, and C. Chouchkov, (1998), GABA- and glutamate-immunoreactivity in sensory ganglia of cat: a quantitative analysis. Arch. Physiol. Biochem. 106:362-369.

Swanson R A, Graham S H, Fluorocitrate and fluoroacetate effects on astrocyte metabolism in vitro. Brain Res. 664(1-2):94-100, 1994.

J. E. Swett and C. J. Woolf, (1985), The somatotopic organization of primary afferent terminals in the superficial laminae of the dorsal horn of the rat spinal cord. J. Comp. Neurol. 231:66-77.

J. E. Swett, Y. Torigoe, V. Elie, C. Bourassa, and P. Miller, (1991), Sensory neurons of the rat sciatic nerve. Exp. Neurol. 114:82-103.

S. Tate, S. Benn, C. Hick, D. Trezise, V. John, R. J. Mannion, M. Costigan, C. Plumpton, D. Grose, Z. Gladwell, G. Kendall, K. Dale, C. Bountra, and C. J. Woolf, (1998), Two sodium channels contribute to the TTX-R sodium current in primary sensory neurons. Nat. Neurosci. 1:653-655.

A. Tang and N. P. Curthoys, (2001), Identification of zetacrystallin/NADPH:quinone reductase as a renal glutaminase mRNA pH response element-binding protein. J. Biol. Chem. 276:21375-21380.

J. Tong, R. A. Shapiro, and N. P. Curthoys, (1987), Changes in the levels of translatable glutaminase mRNA during onset and recovery from metabolic acidosis. Biochemistry 26:2773-2777.

L. Urban, S. W. N. Thompson, and A. Dray, (1994), Modulation of spinal excitability: co-operation between neurokinin and excitatory amino acid neurotransmitters. Trends Neurosci. 17:432-437.

T. Ushida, T. Tani, M. Kawasaki, O. Iwatsu, and H. Yamamoto, (1999), Peripheral administration of an N-methyl-D-aspartate receptor antagonist (MK-801) changes dorsal horn neuronal responses in rats. Neurosci Lett. 260:89-92.

C. J. Van den Berg, (1972), Metabolic compartments in mouse brain based on glucose and acetate metabolism, in: R. Balázs, J. E. Cremer (Eds.), Metabolic Compartmentation in the Brain. Wiley, New York, pp. 137-166.

Vorhaben J E, Campbell J W, Submitochondrial localization and function of enzymes of glutamine metabolism in avian liver. J Cell Biol. 73(2):300-10, 1977.

A. Wanaka, Y. Shiotani, H. Kiyama, T. Matsuyama, T. Kamada, S. Shiosaka, and M. Tohyama, (1987), Glutamate-like immunoreactive structures in primary sensory neurons in the rat detected by a specific antiserum against glutamate. Exp. Brain Res. 65:691-694.

R. A. Waniewski and D. L. Martin, (1998), Preferential utilization of acetate by astrocytes in attributable to transport. J. Neurosci. 18:5225-5233.

H. Wang, R. J. Liu, R. X. Zhang, and J. T Qiao, (1997), Peripheral NMDA receptors contribute to activation of nociceptors: a c-fos expression study in rats. Neurosci. Lett. 221: 101-104.

Y. Wang, K. Santa-Cruz, C. DeCarli, and J. A. Johnson, (2000), NAD(P)H:quinone oxidoreductase activity is increased in hippocampal pyramidal neurons of patients with Alzheimer's disease. Neurobiol Aging 21:525-531.

D. Weinreich and R. Hammerschlag, (1975), Nerve impulse-enhanced release of amino acids from non-synaptic regions of peripheral and central nerve trunks of bullfrog. Brain Res. 84:137-142.

R. J. Wenthold, R. A. Altschuler, K. K. Skaggs, and K. A. Reeks, (1987), Immunocytochemical characterization of glutamate dehydrogenase in the cerebellum of the rat. J. Neurochem. 48:636-643.

N. Westergaard, U. Sonnewald, and A. Schousboe, (1994), Release of α-keto-glutarate, malate and succinate from culturaed astrocytes: possible role in amino acid neurotransmitter homeostasis. Neurosci. Lett. 176:105-109.

K. N. Westlund, Y. C. Sun, K. A. Sluka, P. M. Dougherty, L. S. Sorkin, and W. D. Willis, (1992), Neural changes in acute arthritis in monkeys. II. Increased glutamate immunoreactivity in the medial articular nerve. Brain Res. Rev. 17:15-27.

D. D. Wheeler and L. L. Boyarsky, (1968), Influx of glutamic acid in peripheral nerve—characteristics in influx. J. Neurochem. 15:1019-1031.

W. D. Willis and R. E. Coggeshall, (1991), Dorsal root ganglion cells and their processes. In: Sensory Mechanisms of the Spinal Cord. Plenum Press, New York and London, pp. 47-48.

M. W. Wilson, L. P. Schelonka, D. Siegel, A. Meininger, and D. Ross, (2001), Immunohistochemical localization of NAD(P)H:quinone oxidoreductase in conjunctival melanomas and primary acquired melanosis. Curr. Eye Res. 22:348-352.

S. L. Winski, M. Faig, M. A. Bianchet, D. Siegel, E. Swann, K. Fung, M. W. Duncan, C. J. Moody, L. M. Amzel, and D. Ross, (2001), Characterization of a mechanism-based inhibitor of NAD(P)H:quinone oxidoreductase 1 by biochemical, X-ray crystallographic, and mass spectrometric approaches. Biochemistry 40:15135-15142.

J. N. Wood and R. Docherty, (1997), Chemical activators of sensory neurons. Ann. Rev. Physiol. 59:457-482.

C. J. Woolf, (1996), Phenotypic modification of primary sensory neurons: the role of nerve growth factor in the production of persistent pain. Philos. Trans. R. Soc. Lond. B. Biol. Sci. 351:441-448.

T. Yamaoka, M. Kondo, S. Honda, H. Iwahana, M. Moritani, S. Ii, K. Yoshimoto, and M. Itakura, (1997), Amidophosphoribosyltransferase limits the rate of cell growth-linked de novo purine biosynthesis in the presence of constant capacity of salvage purine biosynthesis. J. Biol. Chem. 272:17719-17725.

L. C. Yang, M. Marsala, and T. L. Yaksh, (1996), Characterization of spinal amino acids, cirtrulline and PGE2 release after carrageenan/kaolin-induced knee joint inflammation: a chronic microdialysis study. Pain 67:345-354.

M. Yudkoff, I. Nissim, D. Nelson, Z. P. Lin, and M. Erecinska, (1991), Glutamate dehydrogenase reaction as a source of glutamic acid in synaptosomes. J. Neurochem. 57:153-160.

H. Zalkin and J. L. Smith, (1998), Enzymes utilizing glutamine as an amide donor. Adv. Enzymol. 72:87-144.

M. Zimmerman, (1983), Ethical guidelines for investigations of experimental pain in conscious animals. Pain 16:109-110.

X. Zhang, Z. O. Xu, T. J. Shi, M. Landry, K. Holmberg, G. Ju, Y. G. Tong, L. Bao, X. P. Cheng, Z. Wiesenfeld-Hallin, A. Lozano, J. Dostrovsky, and T. Hokfelt, (1998), Regulation of expression of galanin and galanin receptors in dorsal root ganglia and spinal cord after axotomy and inflammation. Ann. N. Y. Acad. Sci. 863:402-413.

S. Zhou, L. Bonasera, and S. M. Carlton, (1996), Peripheral administration of NMDA, AMPA or KA results in pain behaviors in rats. Neuroreport 7:895-900.

What is claimed is:

1. A method for alleviating chronic pain in a subject, the method comprising the steps of:

administering an effective amount of at least one inhibitor of neurotransmitter synthesis to a subject suffering from chronic pain at a peripheral nervous system inflammation site, wherein the at least one inhibitor of neurotransmitter synthesis is selected from the group consisting of an inhibitor of glutamine synthetase enzyme activity, an inhibitor of glutamate dehydrogenase enzyme activity, an inhibitor of pyruvate carboxylase enzyme activity, a glutamine cycle inhibitor, a glial cell tricarboxylic acid cycle inhibitor, and combinations thereof; and wherein the administration of the effective amount of at least one inhibitor of neurotransmitter synthesis results in inhibition in synthesis of at least one neurotransmitter in the peripheral nervous system of the subject at the peripheral nervous system inflammation site, thereby resulting in a reduction in glutamate stimulation of peripheral sensory nerve fibers, whereby a reduction in nociceptive responses at the peripheral nervous system inflammation site is observed without any resulting acute pain behavior.

2. The method of claim 1, wherein the subject is a human.

3. The method of claim 1, wherein the step of administering an effective amount of at least one inhibitor of neurotransmitter synthesis to a subject suffering from chronic pain at a peripheral nervous system inflammation site is further defined as locally administering an effective amount of at least one inhibitor of neurotransmitter synthesis to a subject suffering from chronic pain at a peripheral nervous system inflammation site.

4. The method of claim 1, wherein the step of administering an effective amount of at least one inhibitor of neurotransmitter synthesis to a subject suffering from chronic pain at a peripheral nervous system inflammation site is further defined as injecting an effective amount of at least one inhibitor of neurotransmitter synthesis to a subject suffering from chronic pain at a peripheral nervous system inflammation site.

5. The method of claim 1, wherein the step of administering an effective amount of at least one inhibitor of neurotransmitter synthesis to a subject suffering from chronic pain at a peripheral nervous system inflammation site is further defined as topically applying an effective amount of at least one inhibitor of neurotransmitter synthesis to a subject suffering from chronic pain at a peripheral nervous system inflammation site.

6. The method of claim 1, wherein the step of administering an effective amount of at least one inhibitor of neurotransmitter synthesis to a subject suffering from chronic pain at a peripheral nervous system inflammation site is further defined as orally administering an effective amount of at least one inhibitor of neurotransmitter synthesis to a subject suffering from chronic pain at a peripheral nervous system inflammation site.

7. The method of claim 1, wherein the administration of the effective amount of at least one inhibitor of neurotransmitter synthesis results in a reduction in nociceptive responses at the peripheral nervous system inflammation site for at least two days without any resulting acute pain behavior.

8. The method of claim 1 wherein, in the step of administering an effective amount of at least one inhibitor of neurotransmitter synthesis, the at least one inhibitor of neurotransmitter synthesis is an inhibitor of glutamine synthetase enzyme activity selected from the group consisting of methionine-S-sulfoximine (MSO), phosphinothricin (PPT), 4-N-hydroxy-L-2,4-diaminobutyric acid (NH-DABA), Delta-hydroxylysine, and combinations thereof.

9. The method of claim 1 wherein, in the step of administering an effective amount of at least one inhibitor of neurotransmitter synthesis, the at least one inhibitor of neurotransmitter synthesis is an inhibitor of glutamate dehydrogenase enzyme activity selected from the group consisting of bromofuroate, Palmitoyl-Coenzyme-A (Palmitoyl-Co-A), orthovanadate, vanadyl sulphate, vanadyl acetylacetonate, glutarate, 2-oxoglutarate ($\alpha$-ketoglutarate), estrogen, estrogen analogues, pyridine-2,6-dicarboxylic acid, and combinations thereof.

10. The method of claim 1 wherein, in the step of administering an effective amount of at least one inhibitor of neurotransmitter synthesis, the at least one inhibitor of neurotransmitter synthesis is an inhibitor of pyruvate carboxylase enzyme activity selected from the group consisting of phenyl acetic acid (PAA), phenylacetyl Coenzyme-A, phenylacetyl Co-A ester, oxamate, and combinations thereof.

11. The method of claim 1 wherein, in the step of administering an effective amount of at least one inhibitor of neurotransmitter synthesis, the at least one inhibitor of neurotransmitter synthesis is a glial cell tricarboxylic acid cycle inhibitor selected from the group consisting of fluoroacetate, fluorocitrate, and combinations thereof.

12. The method of claim 6, wherein the effective amount of at least one inhibitor of neurotransmitter synthesis is in the form of a prodrug.

13. The method of claim 6, wherein the effective amount of at least one inhibitor of neurotransmitter synthesis demonstrates substantially no penetration across the central nervous system blood brain barrier.

14. A method for alleviating acute and chronic pain in a subject, the method comprising the steps of:
  administering an effective amount of at least one inhibitor of neurotransmitter synthesis to a subject suffering from acute and chronic pain at a peripheral nervous system inflammation site, wherein the at least one inhibitor of neurotransmitter synthesis is selected from the group consisting of an inhibitor of glutamine synthetase enzyme activity, an inhibitor of glutamate dehydrogenase enzyme activity, an inhibitor of pyruvate carboxylase enzyme activity, a glutamine cycle inhibitor, a glial cell tricarboxylic acid cycle inhibitor, and combinations thereof;
  administering an effective amount of at least one compound having analgesic effects to the subject at the peripheral nervous system inflammation site; and
  wherein the administration of the effective amount of at least one inhibitor of neurotransmitter synthesis results in inhibition of at least one neurotransmitter in the peripheral nervous system of the subject at the peripheral nervous system inflammation site, thereby resulting in a reduction in glutamate stimulation of peripheral sensory nerve fibers, and the administration of the effective amount of at least one compound having analgesic effects results in a decrease in nociceptive responses at the peripheral nervous system inflammation site without any resulting acute pain behavior.

15. The method of claim 14 wherein, in the step of administering an effective amount of at least one compound having analgesic effects, the at least one compound having analgesic effects is a glutamate antagonist or an inhibitor of glutamate binding to glutamate receptors on peripheral sensory nerves.

16. The method of claim 14, wherein the administration of the effective amount of at least one inhibitor of neurotransmitter synthesis and the administration of the effective amount of at least one compound having analgesic effects results in a decrease in nociceptive responses at the peripheral nervous system inflammation site that last for a period of at least two days without any resulting acute pain behavior.

17. The method of claim 14 wherein, in the step of administering an effective amount of at least one inhibitor of neurotransmitter synthesis, the at least one inhibitor of neurotransmitter synthesis is an inhibitor of glutamine synthetase enzyme activity selected from the group consisting of methionine-S-sulfoximine (MSO), phosphinothricin (PPT), 4-N-hydroxy-L-2,4-diaminobutyric acid (NH-DABA), Delta-hydroxylysine, and combinations thereof.

18. The method of claim 14 wherein, in the step of administering an effective amount of at least one inhibitor of neurotransmitter synthesis, the at least one inhibitor of neurotransmitter synthesis is an inhibitor of glutamate dehydrogenase enzyme activity selected from the group consisting of bromofuroate, Palmitoyl-Coenzyme-A (Palmitoyl-Co-A), orthovanadate, vanadyl sulphate, vanadyl acetylacetonate, glutarate, 2-oxoglutarate ($\alpha$-ketoglutarate), estrogen, estrogen analogues, pyridine-2,6-dicarboxylic acid, and combinations thereof.

19. The method of claim 14 wherein, in the step of administering an effective amount of at least one inhibitor of neurotransmitter synthesis, the at least one inhibitor of neurotransmitter synthesis is an inhibitor of pyruvate carboxylase enzyme activity selected from the group consisting of phenyl acetic acid (PAA), phenylacetyl Coenzyme-A, phenylacetyl Co-A ester, oxamate, and combinations thereof.

20. The method of claim 14 wherein, in the step of administering an effective amount of at least one inhibitor of neurotransmitter synthesis, the at least one inhibitor of neurotransmitter synthesis is a glial cell tricarboxylic acid cycle inhibitor selected from the group consisting of fluoroacetate, fluorocitrate, and combinations thereof.

* * * * *

UNITED STATES PATENT AND TRADEMARK OFFICE
CERTIFICATE OF CORRECTION

PATENT NO.          : 7,504,231 B2
APPLICATION NO.  : 10/660093
DATED                  : March 17, 2009
INVENTOR(S)         : Kenneth E. Miller It is certified that error appears in the above-identified patent and that said Letters Patent is hereby corrected as shown below:

In the Specification:

Column 5, line 60: Delete "©" and replace with -- @ --.

Column 25, line 42: Delete "(PM)" and replace with -- (PAA) --.

Signed and Sealed this

Fifth Day of May, 2009

JOHN DOLL
*Acting Director of the United States Patent and Trademark Office*